US011230699B2

(12) United States Patent
Lee et al.

(10) Patent No.: US 11,230,699 B2
(45) Date of Patent: *Jan. 25, 2022

(54) CHIMERIC ANTIGEN RECEPTOR-MODIFIED NK-92 CELLS TARGETING EGFR SUPER-FAMILY RECEPTORS

(71) Applicant: NANTKWEST, INC., Culver City, CA (US)

(72) Inventors: John H. Lee, Culver City, CA (US); Laurent H. Boissel, Culver City, CA (US); Hans G. Klingemann, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/775,111

(22) Filed: Jan. 28, 2020

(65) Prior Publication Data

US 2021/0230547 A1 Jul. 29, 2021

(51) Int. Cl.
*A61K 48/00* (2006.01)
*C07H 21/04* (2006.01)
*C12N 5/0783* (2010.01)
*C07K 16/32* (2006.01)
*C07K 14/735* (2006.01)
*C07K 14/55* (2006.01)
*C07K 14/54* (2006.01)
*C07K 14/71* (2006.01)
*A61K 35/17* (2015.01)
*A61P 35/00* (2006.01)
*A61K 45/06* (2006.01)
*C07K 16/28* (2006.01)
*C12N 15/00* (2006.01)

(52) U.S. Cl.
CPC ............ *C12N 5/0646* (2013.01); *A61K 35/17* (2013.01); *A61K 45/06* (2013.01); *A61P 35/00* (2018.01); *C07K 14/5434* (2013.01); *C07K 14/5443* (2013.01); *C07K 14/55* (2013.01); *C07K 14/70535* (2013.01); *C07K 14/71* (2013.01); *C07K 16/2863* (2013.01); *C07K 16/32* (2013.01); *C07K 2317/24* (2013.01); *C07K 2317/53* (2013.01); *C07K 2317/622* (2013.01); *C07K 2317/732* (2013.01); *C07K 2319/02* (2013.01); *C07K 2319/03* (2013.01); *C07K 2319/30* (2013.01); *C07K 2319/33* (2013.01)

(58) Field of Classification Search
CPC ............................. C12N 5/0646; C07K 16/32; C07K 14/70535; C07K 14/55; C07K 14/5443; C07K 14/5434; C07K 14/71; A61K 35/17

See application file for complete search history.

(56) References Cited

U.S. PATENT DOCUMENTS

| 6,034,072 | A | 3/2000 | Ralston et al. |
| 7,098,008 | B2 | 8/2006 | Park et al. |
| 7,618,817 | B2 | 11/2009 | Campbell |
| 8,034,332 | B2 | 10/2011 | Klingemann |
| 8,067,227 | B2 * | 11/2011 | Wahler ............... C07K 14/5434 435/320.1 |
| 8,313,943 | B2 | 11/2012 | Campbell |
| 8,987,417 | B2 * | 3/2015 | Zwaagstra ......... A61K 47/6881 530/350 |
| 9,061,059 | B2 | 6/2015 | Chakraborty et al. |
| 9,150,636 | B2 | 10/2015 | Campbell |
| 9,181,322 | B2 | 11/2015 | Campbell |
| 9,266,938 | B2 | 2/2016 | Ast et al. |
| 10,138,462 | B2 | 11/2018 | Klingemann |
| 10,456,420 | B2 | 10/2019 | Lee et al. |
| 10,960,024 | B2 | 3/2021 | Klingemann et al. |
| 2002/0068044 | A1 | 6/2002 | Klingemann |
| 2003/0105292 | A1 | 6/2003 | Liaw et al. |
| 2003/0167531 | A1 | 9/2003 | Russell et al. |
| 2004/0052770 | A1 | 3/2004 | Klingemann |
| 2008/0247990 | A1 | 10/2008 | Campbell |
| 2013/0040386 | A1 | 2/2013 | Campbell |
| 2013/0189268 | A1 | 7/2013 | Du et al. |
| 2013/0280285 | A1 | 10/2013 | Schonfeld et al. |

(Continued)

FOREIGN PATENT DOCUMENTS

| WO | 98/49268 A1 | 11/1998 |
| WO | 99/024566 A1 | 5/1999 |

(Continued)

OTHER PUBLICATIONS

Abate-Daga et al., "CAR models: next -generation CAR modifications for enhanced T-cell function", Oncolytics (2016) pp. 1-7.
ATCC N K-92 product, Credible leads to incredible; pp. 1-6; downloaded Dec. 5, 2019.
Konstantinidis et al., "Targeting IL-2 to the endoplasmic reticulum confines autocrine growth stimulation to NK-92 cells" Experimental Hematology 33 (2005) 159-164.
International Search Report and Written opinion received for PCT Application Serial No. PCT/US19/44655, dated Dec. 4, 2019, 17 pages.

(Continued)

*Primary Examiner* — Quang Nguyen
(74) *Attorney, Agent, or Firm* — Martin Fessenmaier; Umberg Zipser LLP

(57) ABSTRACT

Provided are genetically modified NK cells expressing a chimeric antigen receptor targeting an EGFR superfamily receptor. The CAR can comprise an intracellular domain of FcεRIγ and further recombinant proteins expressed by the genetically modified NK cells are CD16, autocrine growth stimulating cytokines, and optionally one of IL-12, a TGF-beta trap, or a homing receptor. Also described are methods for treating a patient having or suspected of having a disease that is treatable with NK-92 cells, such as cancer, comprising administering to the patient the genetically modified NK cells.

27 Claims, 30 Drawing Sheets

Specification includes a Sequence Listing.

(56) References Cited

U.S. PATENT DOCUMENTS

| | | | |
|---|---|---|---|
| 2014/0099714 A1 | 4/2014 | Klingemann | |
| 2014/0242701 A1 | 8/2014 | Shiku et al. | |
| 2014/0255363 A1* | 9/2014 | Metelitsa | A61K 31/4545 424/93.21 |
| 2014/0274909 A1 | 9/2014 | Orentas et al. | |
| 2014/0322183 A1 | 10/2014 | Milone et al. | |
| 2018/0044424 A1 | 2/2018 | June et al. | |
| 2018/0057795 A1 | 3/2018 | Childs et al. | |
| 2018/0133296 A1* | 5/2018 | Barrett | C07K 16/2803 |
| 2018/0155439 A1 | 6/2018 | Galipeau et al. | |
| 2018/0163176 A1 | 6/2018 | Lee | |
| 2018/0187149 A1 | 7/2018 | Ma et al. | |
| 2018/0207295 A1 | 7/2018 | Fotin-Mleczek et al. | |
| 2018/0258397 A1 | 9/2018 | Klingemann et al. | |
| 2020/0023010 A1 | 1/2020 | Dilillo et al. | |
| 2020/0038441 A1 | 2/2020 | Klingemann et al. | |
| 2020/0093863 A1 | 3/2020 | Klingemann et al. | |

FOREIGN PATENT DOCUMENTS

| | | | |
|---|---|---|---|
| WO | 90/20460 A1 | 4/2000 | |
| WO | 03/008583 A2 | 1/2003 | |
| WO | 03/035837 A2 | 5/2003 | |
| WO | 03/084570 A1 | 10/2003 | |
| WO | 03/101485 A1 | 12/2003 | |
| WO | 2008/157367 A1 | 12/2008 | |
| WO | 2014/039523 A1 | 3/2014 | |
| WO | 2014/099671 A1 | 6/2014 | |
| WO | 2016/176639 A1 | 11/2016 | |
| WO | 2016/201304 A1 | 12/2016 | |
| WO | 2017/123548 A1 | 7/2017 | |
| WO | 2017/214569 A1 | 12/2017 | |
| WO | 2018/076391 A1 | 5/2018 | |
| WO | WO-2019089813 A1 * | 5/2019 | A61K 39/0011 |
| WO | 2019/152513 A1 | 8/2019 | |
| WO | 2019/226521 A1 | 11/2019 | |
| WO | 2019/226708 A1 | 11/2019 | |
| WO | WO 2019/226708 * | 11/2019 | |
| WO | 2020/010110 A1 | 1/2020 | |
| WO | 2020/028656 A1 | 2/2020 | |

OTHER PUBLICATIONS

GenBank MH107787, "Mammalian expression vector pEXPR50, complete sequence", Apr. 11, 2018, https://www.ncbi.nlm.nih.gov/nuccore/MH107787.1/, 3 pages.

Non-Final Office Action received for U.S. Appl. No. 16/529,029 dated Dec. 11, 2019, 26 pages.

Swarts et al., "Tumor Microenvironment Complexity: Emerging Roles in Cancer Therapy", Cancer Research, Mar. 13, 2012, vol. 72, pp. 2473-2480.

Herberman et al., "Natural Killer Cells: Their Role in Defenses Against Disease", Science, Oct. 2, 1981, vol. 214, pp. 24-30.

Smith et al., "Comparison of Biosequences", Advances in applied mathematics 2, 1981, pp. 482-489.

Needleman et al., "A General Method Applicable to the Search for Similarities in the Amino Acid Sequence of Two Proteins", J. Mol. Biol., 1970, vol. 48, pp. 443-453.

Pearson et al., "Improved tools for biological sequence comparison", Biochemistry, Proc. Natl. Acad. Sci. USA, Apr. 1988, vol. 85, pp. 2444-2448.

Altschul et al., "Gapped Blast and PSI-BLAST: A new generation of protein database search programs", Nucleic Acids Research, 1997, vol. 25, No. 17, pp. 3389-3402.

Altschul et al., "Basic Local Alignment Tool", J. Mol. Biol., 1990, vol. 215, pp. 403-410.

Henikoff et al., "Amino acid substitution matrices from protein blocks", Biochemistry, Proc. Natl. Acad. Sci. USA, Nov. 1992, vol. 89, pp. 10915-10919.

Gong et al., "Characterization of a human cell line (NK-92) with phenotypical and functional characteristics of activated natural killer cells", Leukemia, Apr. 1994, vol. 8, No. 4, pp. 652-658.

Maki et al., "Factors Regulating the Cytotoxic Activity of the Human Natural Killer Cell Line, NK-92", Journal of hematotherapy & Stem Cell Research, 2001, vol. 10, pp. 369-383.

Suck et al., "NK 92: an 'off the shelf therapeutic' for adoptive natural killer cell based cancer immunotherapy", Cancer Immunol Immunotherapy, Nov. 11, 2015, vol. 65, No. 4, pp. 485-492.

Klingemann et al., "Purging of malignant cells from blood after short ex vivo incubation with NK-92 cells", Blood, 1996, vol. 87, No. 11, pp. 4913-4914.

Yan et al., "Antileukemia activity of a natural killer cell line against human leukaemia's", Clinical Cancer Research, Nov. 1998, vol. 4, No. 11, pp. 2859-2868.

Swift et al., "Natural killer cell lines preferentially kill clonogenic multiple myeloma cells and decrease myeloma engraftment in a bioluminescent xenograft mouse model", Haematologica, Cell Therapy and Immunotherapy, 2012, vol. 97, No. 7, pp. 1020-1028.

Tam et al., "Immunotherapy of Malignant Melanoma in a SCID Mouse Model Using the Highly Cytotoxic Natural Killer Cell Line NK-92", Journal of Hematotherapy, 1999, vol. 8, pp. 281-290.

Konstantinidis et al., "Targeting IL-2 to the endoplasmic reticulum confines autocrine growth stimulation to NK-92 cells", Experimental Hematology, 2005, vol. 33. No. 2, pp. 159-164.

Zwaagstra et al., "Engineering and Therapeutic Application of Single-Chain Bivalent TGF-β Family Traps", Mol. Canc. THer. 2012, vol. 11(7), pp. 1477-1487.

Batzer et al., "Enhanced evolutionary PCR using oligonucleotides with inosine at the 3'-terminus", Nucleic Acids Research, 1991, vol. 19, No. 18, 1 page.

Ohtsuka et al., "An Alternative Approach to Deoxyoligonucleotides as Hybridization Probes by Insertion of Deoxyinosine at Ambiguous Codon Positions", The Journal of Biological Chemistry, Mar. 10, 1985, vol. 260, No. 5, pp. 2605-2608.

Rossolini et al., Use of deoxyinosine-containing primers vs Degenerate primers for polymerase chain reaction based on Ambiguous sequence information, Molecular and Cellular Probes, 1994, vol. 8, pp. 91-98.

Yazawa K, Fisher W E, Brunicardi F C: Current Progress in Suicide gene therapy for cancer. World J. Surg. Jul. 2002; 26(7): 783-9.

Wang et al., "Augmented anti-tumor activity of NK-92 cells expressing chimeric receptors of TGF-betaR II and NKG2D", Cancer Immunol Immunother, 2017, vol. 66, No. 4, 12 pages.

Yang et al., "Blocking transforming growth factor-beta signaling pathway augments antitumor effect of adoptive NK-92 cell therapy", International Immunopharmacology, 2013, vol. 17, pp. 198-204.

Final Office Action received for U.S. Appl. No. 16/529,029 dated Feb. 20, 2020, 21 pages.

Non-Final Office Action received for U.S. Appl. No. 16/707,807 dated Feb. 14, 2020, 23 pages.

Clark et al., "Inferring nonneutral evolution from human-chimp-mouse orthologous gene trios", Science, 2003, vol. 302, pp. 1960-1963.

Somanchi et al., "Engineering lymph node homing of ex vivo-expanded human natural killer cells via trogocytosis of the chemokine receptor CCR7", Blood, 2012, vol. 119, No. 22, 5164-5172.

Non-Final Office Action received for U.S. Appl. No. 16/708,082 dated Feb. 18, 2020, 16 pages.

Haynes et al., "Redirecting Mouse CTL Against Colon Carcinoma: Superior Signaling Efficacy of Single-Chain Variable Domain Chimeras Containing TCR-ζ vs FcεRI-γ", The Journal of Immunology, 2001, vol. 166, No. 1, pp. 182-187.

Cartellieri et al., "Chimeric antigen receptor-engineered T cells for immunotherapy of cancer", Journal of Biomedicine and Biotechnology, vol. 10, pp. 1-13.

Bollino et al., "Chimeric antigen receptor-engineered natural killer and natural killer T cells for cancer immunotherapy", Transl. Res., Sep. 2017, vol. 187, 21 pages.

Bruhns et al., "Specificity and affinity of human Fcgamma receptors and their polymorphic variants for human IgG subclasses", Blood, vol. 113, No. 16, pp. 3716-3725.

Garcia-Sanchez et al., "Cytosine deaminase adenoviral vector and 5-fluorocytosine selectively reduce breast cancer cells 1 million-

(56) References Cited

OTHER PUBLICATIONS fold when they contaminate hematopoietic cells: a potential purging method for autologous transplantation", Blood, vol. 92, No. 2, 1998, pp. 672-682.

Touati et al., "A suicide gene therapy combining the improvement of cyclophosphamide tumor cytotoxicity and the development of an anti-tumor immune response", Current Gene Therapy, 2014, vol. 14, pp. 236-246.

Di Stasi et al., "Inducible apoptosis as a safety switch for adoptive cell therapy", N Engl J Med., Nov. 3, 2011, vol. 365, No. 18, pp. 1673-1683.

Morgan Richard A, "Live and Let Die: A New Suicide Gene Therapy Moves to the Clinic", Molecular therapy, Jan. 2012, vol. 20, No. 1, pp. 11-13.

Jochems et al., "An NK cell line (haN K) expressing high levels of granzyme and engineered to express the high affinity CD16 allele", Oncotarget 2016;7:86359-86373.

Randolph Gwendalyn J, "Dendritic cell migration to lymph nodes: cytokines, chemokines, and lipid mediators", Seminars in Immunology, 2001, vol. 13, pp. 267-274.

Denman et al., "Membrane-Bound IL-21 Promotes Sustained Ex Vivo Proliferation of Human Natural Killer Cells", Plos One, Jan. 2012, vol. 7, No. 1, e30264, pp. 1-12.

Ngo et al., "Computational Complexity, Protein Structure Prediction, and the Levinthal Paradox", The Protein Folding Problem and Tertiary Structure Prediction, 1994, 433-495.

Rudinger J., "Characteristics of the amino acids as components of a peptide hormone sequene", Peptide Hormones, 1976, 8 pages.

Rudikoff et al., "Single amino acid substitution altering antigen-binding specificity" Proc. Natl Acad. Sci., 1982, vol. 79, pp. 1979-1983.

Coleman et al., "Effects of amino acid sequence changes on antibody-antigen interactions", Research in Immunology, 1994, vol. 145, pp. 33-36.

Almagro et al., "Humanization of antibodies", Frontiers in Bioscience, 2008, vol. 13, No. 5, pp. 1619-1633.

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue", The Journal of Cell Biology, 1990, vol. 111, pp. 2129-2138.

Notice of Allowance received for U.S. Appl. No. 16/707,807 dated Jul. 16, 2021, 27 pages.

Notice of Allowance received for U.S. Appl. No. 16/708,082 dated May 21, 2021, 18 pages.

\* cited by examiner

SEQUENCE LISTING

<160> NUMBER OF SEQ ID NOS: 43

<210> SEQ ID NO 1
<211> LENGTH: 41
<212> TYPE: PRT
<213> ORGANISM: Artificial Sequence

```
<220> FEATURE:
<223> OTHER INFORMATION: FC-epsilon-RI-gamma cytoplasmic domain

<400> SEQUENCE: 1

Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40

<210> SEQ ID NO 2
<211> LENGTH: 123
<212> TYPE: DNA
<213> ORGANISM: Artificial Sequence
<220> FEATURE:
<223> OTHER INFORMATION: FC-epsilon-RI-gamma cytoplasmic domain

<400> SEQUENCE: 2
ctgaagatcc aggtccgaaa ggccgccatc accagctacg agaagtctga tggcgtgtac      60
accggcctga gcaccagaaa ccaggaaacc tacgagacac tgaagcacga agccccc       120 cag                                                                  123

<210> SEQ ID NO 3
<211> LENGTH: 54
<212> TYPE: PRT
<213> ORGANISM: Artificial Sequence
<220> FEATURE:
<223> OTHER INFORMATION: CD8 hinge

<400> SEQUENCE: 3

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Phe Trp
        35                  40                  45

Val Leu Val Val Val Gly
    50

<210> SEQ ID NO 4
<211> LENGTH: 20
<212> TYPE: PRT
<213> ORGANISM: Artificial Sequence
<220> FEATURE:
<223> OTHER INFORMATION: CD28 transmembrane domain

<400> SEQUENCE: 4

Gly Val Leu Ala Cys Tyr Ser Leu Leu Val Thr Val Ala Phe Ile Ile
1               5                   10                  15

Phe Trp Val Arg
            20

<210> SEQ ID NO 5
<211> LENGTH: 41
<212> TYPE: PRT
<213> ORGANISM: Artificial Sequence
<220> FEATURE:
<223> OTHER INFORMATION: CD28 signaling domain

<400> SEQUENCE: 5

Arg Ser Lys Arg Ser Arg Leu Leu His Ser Asp Tyr Met Asn Met Thr
```

```
1               5                   10                  15
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 6
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 6

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 7
<211> LENGTH: 113
<212> TYPE: PRT
<213> ORGANISM: Artificial Sequence
<220> FEATURE:
<223> OTHER INFORMATION: CD3 zeta signaling domain

<400> SEQUENCE: 7

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 8
<211> LENGTH: 339
<212> TYPE: DNA
<213> ORGANISM: Artificial Sequence
<220> FEATURE:
<223> OTHER INFORMATION: CD3 zeta

<400> SEQUENCE: 8

```
gtgaagttta gcagatctgc cgacgcccct gcctaccagc agggacagaa tcagctgtac      60
aacgagctga acctgggcag acgggaagag tacgacgtgc tggataagag aagaggcaga     120
gatcccgaga tgggcggcaa gccccagaga agaaagaatc cccaggaagg cctgtataac     180
gaactgcaga agacaagat ggccgaggcc tacagcgaga tcggcatgaa gggcgagaga      240
agaagaggca agggccacga tggactgtac cagggactga gcacagccac caaggatacc     300
```
tacgatgccc tgcacatgca ggccctgcct ccaagataa                339

<210> SEQ ID NO 9
<211> LENGTH: 153
<212> TYPE: PRT
<213> ORGANISM: Artificial Sequence
<220> FEATURE:
<223> OTHER INFORMATION: Human IL2

<400> SEQUENCE: 9

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 10
<211> LENGTH: 160
<212> TYPE: PRT
<213> ORGANISM: Artificial Sequence
<220> FEATURE:
<223> OTHER INFORMATION: Human er-IL2

<400> SEQUENCE: 10

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140
```

Cys Gln Ser Ile Ile Ser Thr Leu Thr Gly Ser Glu Lys Asp Glu Leu
145                 150                 155                 160

<210> SEQ ID NO 11
<211> LENGTH: 254
<212> TYPE: PRT
<213> ORGANISM: Artificial Sequence
<220> FEATURE:
<223> OTHER INFORMATION: FCgamma/CD16

<400> SEQUENCE: 11

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 12
<211> LENGTH: 765
<212> TYPE: DNA
<213> ORGANISM: Artificial Sequence
<220> FEATURE:
<223> OTHER INFORMATION: FCgamma/CD16 nt

<400> SEQUENCE: 12
atgtggcagc tgctgctgcc tacagctctc ctgctgctgg tgtccgccgg catgagaacc      60
gaggatctgc ctaaggccgt ggtgttcctg aacccccagt ggtacagagt gctggaaaag     120
gacagcgtga ccctgaagtg ccagggcgcc tacagcccg aggacaatag cacccagtgg     180
ttccacaacg agagcctgat cagcagccag gccagcagct acttcatcga cgccgccacc     240

| | |
|---|---|
| gtggacgaca gcggcgagta tagatgccag accaacctga gcaccctgag cgacccccgtg | 300 |
| cagctggaag tgcacatcgg atggctgctg ctgcaggccc ccagatgggt gttcaaagaa | 360 |
| gaggacccca tccacctgag atgccactct tggaagaaca ccgccctgca caaagtgacc | 420 |
| tacctgcaga acggcaaggg cagaaagtac ttccaccaca cagcgactt ctacatcccc | 480 |
| aaggccaccc tgaaggactc cggctcctac ttctgcagag gcctcgtggg cagcaagaac | 540 |
| gtgtccagcg agacagtgaa catcaccatc acccaggggcc tggccgtgtc taccatcagc | 600 |
| agcttttcc cacccggcta ccaggtgtcc ttctgcctcg tgatggtgct gctgttcgcc | 660 |
| gtggacaccg gcctgtactt cagcgtgaaa acaaacatca gaagcagcac ccgggactgg | 720 |
| aaggaccaca gttcaagtg gcggaaggac ccccaggaca gtga | 765 |

<210> SEQ ID NO 13
<211> LENGTH: 1125
<212> TYPE: DNA
<213> ORGANISM: Artificial Sequence
<220> FEATURE:
<223> OTHER INFORMATION: CCR7

<400> SEQUENCE: 13

| | |
|---|---|
| gccaccatga aaagcgtgct ggtggtggct ctccttgtca ttttccaggt atgcctgtgt | 60 |
| caagatgagg tcacggacga ttacatcgga gacaacacca cagtggacta cactttgttc | 120 |
| gagtctttgt gctccaagaa ggacgtgcgg aactttaaag cctggttcct ccctatcatg | 180 |
| tactccatca tttgtttcgt gggcctactg ggcaatgggc tggtcgtgtt gacctatatc | 240 |
| tatttcaaga ggctcaagac catgaccgat acctacctgc tcaacctggc ggtggcagac | 300 |
| atcctcttcc tctgacccct tccccttctgg gcctacagcg cggccaagtc ctgggtcttc | 360 |
| ggtgtccact tttgcaagct catctttgcc atctacaaga tgagcttctt cagtggcatg | 420 |
| ctcctacttc tttgcatcag cattgaccgc tacgtggcca tcgtccaggc tgtctcagct | 480 |
| caccgccacc gtgcccgcgt ccttctcatc agcaagctgt cctgtgtggg catctggata | 540 |
| ctagccacag tgctctccat cccagagctc ctgtacagtg acctccagag gagcagcagt | 600 |
| gagcaagcga tgcgatgctc tctcatcaca gagcatgtgg aggcctttat caccatccag | 660 |
| gtggcccaga tggtgatcgg ctttctggtc cccctgctgg ccatgagctt ctgttacctt | 720 |
| gtcatcatcc gcaccctgct ccaggcacgc aactttgagc gcaacaaggc catcaaggtg | 780 |
| atcatcgctg tggtcgtggt cttcatagtc ttccagctgc cctacaatgg ggtggtcctg | 840 |
| gcccagacgt tggccaactt caacatcacc agtagcacct gtgagctcag taagcaactc | 900 |
| aacatcgcct acgacgtcac ctacagcctg gcctgcgtcc gctgctgcgt caacccttc | 960 |
| ttgtacgcct tcatcggcgt caagttccgc aacgatctct tcaagctctt caaggacctg | 1020 |
| ggctgcctca gccaggagca gctccggcag tggtcttcct gtcggcacat ccggcgctcc | 1080 |
| tccatgagtg tggaggccga gaccaccacc accttctccc catag | 1125 |

<210> SEQ ID NO 14
<211> LENGTH: 297
<212> TYPE: DNA
<213> ORGANISM: Artificial Sequence
<220> FEATURE:
<223> OTHER INFORMATION: CCL19

<400> SEQUENCE: 14

| | |
|---|---|
| atggccctgc tactggcct cagcctgctg gttctctgga cttccccagc cccaactctg | 60 |

```
agtggcacca atgatgctga agactgctgc ctgtctgtga cccagaaacc catccctggg    120
tacatcgtga ggaacttcca ctaccttctc atcaaggatg ctgcagggt gcctgctgta    180 gtgttcacca cactgagggg ccgccagctc tgtgcacccc cagaccagcc ctgggtagaa    240
cgcatcatcc agagactgca gaggacctca gccaagatga agcgccgcag cagttaa      297

<210> SEQ ID NO 15
<211> LENGTH: 405
<212> TYPE: DNA
<213> ORGANISM: Artificial Sequence
<220> FEATURE:
<223> OTHER INFORMATION: CCL21

<400> SEQUENCE: 15
atggctcagt cactggctct gagcctcctt atcctggttc tggcctttgg catccccagg     60
acccaaggca gtgatggagg ggctcaggac tgttgcctca agtacagcca aaggaagatt    120
cccgccaagg ttgtccgcag ctaccggaag caggaaccaa gcttaggctg ctccatccca    180
gctatcctgt tcttgccccg caagcgctct caggcagagc tatgtgcaga cccaaaggag    240
ctctgggtgc agcagctgat gcagcatctg acaagacac catccccaca gaaaccagcc    300
cagggctgca ggaaggacag gggggcctcc aagactggca gaaaggaaa gggctccaaa    360 ggctgcaaga ggactgagcg gtcacagacc cctaaagggc catag                    405

<210> SEQ ID NO 16
<211> LENGTH: 1083
<212> TYPE: DNA
<213> ORGANISM: Artificial Sequence
<220> FEATURE:
<223> OTHER INFORMATION: CXCR2 nt

<400> SEQUENCE: 16
atggaagatt ttaacatgga gagtgacagc tttgaagatt tctggaaagg tgaagatctt     60
agtaattaca gttacagctc taccctgccc ccttttctac tagatgccgc ccatgtgaa    120 ccagaatccc tggaaatcaa caagtatttt gtggtcatta tctatgccct ggtattcctg    180
ctgagcctgc tgggaaactc cctcgtgatg ctggtcatct atacagcag gtcggccgc     240 tccgtcactg atgtctacct gctgaaccta gccttggccg acctactctt tgccctgacc    300
ttgcccatct gggccgcctc caaggtgaat ggctggattt ttggcacatt cctgtgcaag    360
gtggtctcac tcctgaagga agtcaacttc tatagtggca tcctgctact ggcctgcatc    420
agtgtggacc gttacctggc cattgtccat gccacgcgca cactgaccca gaagcgctac    480
ttggtcaaat tcatatgtct cagcatctgg ggtctgtcct tgctcctggc cctgcctgtc    540
ttacttttcc gaaggaccgt ctactcatcc aatgttagcc cagcctgcta tgaggacatg    600
ggcaacaata tcagcaaactg gcggatgctg ttacggatcc tgccccagtc ctttggcttc    660
atcgtgccac tgctgatcat gctgttctgc tacggattca ccctgcgtac gctgtttaag    720
gcccacatgg ggcagaagca ccgggccatg cgggtcatct ttgctgtcgt cctcatcttc    780
ctgctctgct ggctgcccta caacctggtc ctgctggcag acaccctcat gaggacccag    840
gtgatccagg agacctgtga gcgccgcaat acatcgacc gggctctgga tgccaccgag    900
attctgggca tccttcacag ctgcctcaac cccctcatct acgccttcat ggccagaag    960 tttcgccatg gactcctcaa gattctagct atacatggct tgatcagcaa ggactccctg   1020
cccaaagaca gcaggcctc ctttgttggc tcttcttcag gcacacttc cactactctc   1080 taa                                                                  1083
```

<210> SEQ ID NO 17
<211> LENGTH: 360
<212> TYPE: PRT
<213> ORGANISM: Artificial Sequence
<220> FEATURE:
<223> OTHER INFORMATION: CXCR2 aa

<400> SEQUENCE: 17

```
Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360
```

<210> SEQ ID NO 18
<211> LENGTH: 336
<212> TYPE: DNA
<213> ORGANISM: Artificial Sequence
<220> FEATURE:
<223> OTHER INFORMATION: CXCL4 nt

<400> SEQUENCE: 18

```
atgtccctgc tcccacgccg cgcccctccg gtcagcatga ggctcctggc ggccgcgctg      60
ctcctgctgc tgctggcgct gtacaccgcg cgtgtggacg gtccaaatg caagtgctcc     120
cggaagggac ccaagatccg ctacagcgac gtgaagaagc tggaaatgaa gccaaagtac    180
ccgcactgcg aggagaagat ggttatcatc accaccaaga gcgtgtccag gtaccgaggt    240
caggagcact gcctgcaccc caagctgcag agcaccaagc gcttcatcaa gtggtacaac    300
gcctggaacg agaagcgcag ggtctacgaa gaatag                              336
```

<210> SEQ ID NO 19
<211> LENGTH: 111
<212> TYPE: PRT
<213> ORGANISM: Artificial Sequence
<220> FEATURE:
<223> OTHER INFORMATION: CXCL4 aa

<400> SEQUENCE: 19

```
Met Ser Leu Leu Pro Arg Arg Ala Pro Pro Val Ser Met Arg Leu Leu
1               5                   10                  15

Ala Ala Ala Leu Leu Leu Leu Leu Ala Leu Tyr Thr Ala Arg Val
            20                  25                  30

Asp Gly Ser Lys Cys Lys Cys Ser Arg Lys Gly Pro Lys Ile Arg Tyr
        35                  40                  45

Ser Asp Val Lys Lys Leu Glu Met Lys Pro Lys Tyr Pro His Cys Glu
    50                  55                  60

Glu Lys Met Val Ile Ile Thr Thr Lys Ser Val Ser Arg Tyr Arg Gly
65                  70                  75                  80

Gln Glu His Cys Leu His Pro Lys Leu Gln Ser Thr Lys Arg Phe Ile
                85                  90                  95

Lys Trp Tyr Asn Ala Trp Asn Glu Lys Arg Arg Val Tyr Glu Glu
            100                 105                 110
```

<210> SEQ ID NO 20
<211> LENGTH: 1119
<212> TYPE: DNA
<213> ORGANISM: Artificial Sequence
<220> FEATURE:
<223> OTHER INFORMATION: CD62L nt

<400> SEQUENCE: 20

```
atgatatttc catggaaatg tcagagcacc cagagggact tatggaacat cttcaagttg      60
tgggggtgga caatgctctg ttgtgatttc ctggcacatc atggaaccga ctgctggact    120
taccattatt ctgaaaaacc catgaactgg caaagggcta agattctg ccgagacaat      180
tacacagatt tagttgccat acaaaacaag gcggaaattg agtatctgga aagactctg    240
cctttcagtc gttcttacta ctggatagga atccggaaga taggaggaat atggacgtgg    300
gtgggaacca caaatctct tactgaagaa gcagagaact ggggagatgg tgagcccaac    360
aacaagaaga caaggagga ctgcgtggag atctatatca agagaaacaa agatgcaggc    420
aaatggaacg atgacgcctg ccacaaacta aaggcagccc tctgttacac agcttcttgc    480
```

-continued

```
cagccctggt catgcagtgg ccatggagaa tgtgtagaaa tcatcaataa ttacacctgc    540
aactgtgatg tggggtacta tgggccccag tgtcagtttg tgattcagtg tgagcctttg    600
gaggccccag agctgggtac catggactgt actcacccct tgggaaactt cagcttcagc    660
tcacagtgtg ccttcagctg ctctgaagga acaaacttaa ctgggattga agaaaccacc    720
tgtggaccat ttggaaactg gtcatctcca gaaccaacct gtcaagtgat tcagtgtgag    780
cctctatcag caccagattt ggggatcatg aactgtagcc atcccctggc cagcttcagc    840
tttacctctg catgtacctt catctgctca gaaggaactg agttaattgg gaagaagaaa    900
accatttgtg aatcatctgg aatctggtca atcctagtc caatatgtca aaaattggac     960
aaaagtttct caatgattaa ggagggtgat tataaccccc tcttcattcc agtggcagtc   1020
atggttactg cattctctgg gttggcattt atcatttggc tggcaaggag attaaaaaaa   1080
ggcaagaaat ccaagagaag tatgaatgac ccatattaa                          1119
```

<210> SEQ ID NO 21
<211> LENGTH: 372
<212> TYPE: PRT
<213> ORGANISM: Artificial Sequence
<220> FEATURE:
<223> OTHER INFORMATION: CD62L aa

<400> SEQUENCE: 21

```
Met Ile Phe Pro Trp Lys Cys Gln Ser Thr Gln Arg Asp Leu Trp Asn
 1               5                  10                  15

Ile Phe Lys Leu Trp Gly Trp Thr Met Leu Cys Cys Asp Phe Leu Ala
            20                  25                  30

His His Gly Thr Asp Cys Trp Thr Tyr His Tyr Ser Glu Lys Pro Met
        35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Asn Lys Glu Asp Cys
        115                 120                 125

Val Glu Ile Tyr Ile Lys Arg Asn Lys Asp Ala Gly Lys Trp Asn Asp
    130                 135                 140

Asp Ala Cys His Lys Leu Lys Ala Ala Leu Cys Tyr Thr Ala Ser Cys
145                 150                 155                 160

Gln Pro Trp Ser Cys Ser Gly His Gly Glu Cys Val Glu Ile Ile Asn
                165                 170                 175

Asn Tyr Thr Cys Asn Cys Asp Val Gly Tyr Tyr Gly Pro Gln Cys Gln
            180                 185                 190

Phe Val Ile Gln Cys Glu Pro Leu Glu Ala Pro Glu Leu Gly Thr Met
        195                 200                 205

Asp Cys Thr His Pro Leu Gly Asn Phe Ser Phe Ser Ser Gln Cys Ala
    210                 215                 220

Phe Ser Cys Ser Glu Gly Thr Asn Leu Thr Gly Ile Glu Glu Thr Thr
225                 230                 235                 240

Cys Gly Pro Phe Gly Asn Trp Ser Ser Pro Glu Pro Thr Cys Gln Val
```

```
                    245                 250                 255
Ile Gln Cys Glu Pro Leu Ser Ala Pro Asp Leu Gly Ile Met Asn Cys
            260                 265                 270

Ser His Pro Leu Ala Ser Phe Ser Phe Thr Ser Ala Cys Thr Phe Ile
        275                 280                 285

Cys Ser Glu Gly Thr Glu Leu Ile Gly Lys Lys Thr Ile Cys Glu
        290                 295                 300

Ser Ser Gly Ile Trp Ser Asn Pro Ser Pro Ile Cys Gln Lys Leu Asp
305                 310                 315                 320

Lys Ser Phe Ser Met Ile Lys Glu Gly Asp Tyr Asn Pro Leu Phe Ile
                325                 330                 335

Pro Val Ala Val Met Val Thr Ala Phe Ser Gly Leu Ala Phe Ile Ile
            340                 345                 350

Trp Leu Ala Arg Arg Leu Lys Lys Gly Lys Lys Ser Lys Arg Ser Met
            355                 360                 365

Asn Asp Pro Tyr
    370

<210> SEQ ID NO 22
<211> LENGTH: 300
<212> TYPE: DNA
<213> ORGANISM: Artificial Sequence
<220> FEATURE:
<223> OTHER INFORMATION: IL8 nt

<400> SEQUENCE: 22
atgacttcca agctggccgt ggctctcttg gcagccttcc tgatttctgc agctctgtgt     60
gaaggtgcag ttttgccaag gagtgctaaa gaacttagat gtcagtgcat aaagacatac    120
tccaaacctt tccaccccaa atttatcaaa gaactgagag tgattgagag tggaccacac    180
tgcgccaaca cagaaattat tgtaaagctt tctgatggaa gagagctctg tctggacccc    240
aaggaaaact gggtgcagag ggttgtggag aagtttttga gagggctga  gaattcataa    300

<210> SEQ ID NO 23
<211> LENGTH: 99
<212> TYPE: PRT
<213> ORGANISM: Artificial Sequence
<220> FEATURE:
<223> OTHER INFORMATION: IL8 aa

<400> SEQUENCE: 23

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 24
<211> LENGTH: 324
```

<212> TYPE: DNA
<213> ORGANISM: Artificial Sequence
<220> FEATURE:
<223> OTHER INFORMATION: CXCL1 nt

<400> SEQUENCE: 24

| | | | | | |
|---|---|---|---|---|---|
| atggcccgcg | ctgctctctc | cgccgccccc | agcaatcccc | ggctcctgcg | agtggcactg | 60 |
| ctgctcctgc | tcctggtagc | cgctggccgg | cgcgcagcag | gagcgtccgt | ggccactgaa | 120 |
| ctgcgctgcc | agtgcttgca | gaccctgcag | ggaattcacc | ccaagaacat | ccaaagtgtg | 180 |
| aacgtgaagt | cccccggacc | ccactgcgcc | caaaccgaag | tcatagccac | actcaagaat | 240 |
| gggcggaaag | cttgcctcaa | tcctgcatcc | cccatagtta | agaaaatcat | cgaaaagatg | 300 |
| ctgaacagtg | acaaatccaa | ctga | | | | 324 |

<210> SEQ ID NO 25
<211> LENGTH: 107
<212> TYPE: PRT
<213> ORGANISM: Artificial Sequence
<220> FEATURE:
<223> OTHER INFORMATION: CXCL1 aa

<400> SEQUENCE: 25

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 26
<211> LENGTH: 762
<212> TYPE: DNA
<213> ORGANISM: Artificial Sequence
<220> FEATURE:
<223> OTHER INFORMATION: IL-12 p35 nt

<400> SEQUENCE: 26

| | | | | | |
|---|---|---|---|---|---|
| atgtggcccc | ctgggtcagc | ctcccagcca | ccgccctcac | ctgccgcggc | cacaggtctg | 60 |
| catccagcgg | ctcgccctgt | gtccctgcag | tgccggctca | gcatgtgtcc | agcgcgcagc | 120 |
| ctcctccttg | tggctaccct | ggtcctcctg | gaccacctca | gtttggccag | aaacctcccc | 180 |
| gtggccactc | cagacccagg | aatgttccca | tgccttcacc | actcccaaaa | cctgctgagg | 240 |
| gccgtcagca | acatgctcca | gaaggccaga | caaactctag | aattttaccc | ttgcacttct | 300 |
| gaagagattg | atcatgaaga | tatcacaaaa | gataaaacca | gcacagtgga | ggcctgttta | 360 |
| ccattggaat | taccaagaa | tgagagttgc | ctaaattcca | gagagacctc | tttcataact | 420 |
| aatgggagtt | gcctggcctc | cagaaagacc | tcttttatga | tggccctgtg | ccttagtagt | 480 |
| atttatgaag | acttgaagat | gtaccaggtg | gagttcaaga | ccatgaatgc | aaagcttctg | 540 |
| atggatccta | agaggcagat | ctttctagat | caaaacatgc | tggcagttat | tgatgagctg | 600 |

```
atgcaggccc tgaatttcaa cagtgagact gtgccacaaa atcctccct tgaagaaccg      660 gatttttata aaactaaaat caagctctgc atacttcttc atgctttcag aattcgggca    720
gtgactattg atagagtgat gagctatctg aatgcttcct aa                        762
```

<210> SEQ ID NO 27
<211> LENGTH: 253
<212> TYPE: PRT
<213> ORGANISM: Artificial Sequence
<220> FEATURE:
<223> OTHER INFORMATION: IL-12 p35 aa

<400> SEQUENCE: 27

```
Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

<210> SEQ ID NO 28
<211> LENGTH: 987
<212> TYPE: DNA
<213> ORGANISM: Artificial Sequence
<220> FEATURE:
<223> OTHER INFORMATION: IL-12 p40 nt

<400> SEQUENCE: 28

```
atgtgtcacc agcagttggt catctcttgg ttttccctgg tttttctggc atctcccctc     60
gtggccatat gggaactgaa gaaagatgtt tatgtcgtag aattggattg gtatccggat    120
```

```
gcccctggag aaatggtggt cctcacctgt gacaccctg aagaagatgg tatcacctgg      180
accttggacc agagcagtga ggtcttaggc tctggcaaaa ccctgaccat ccaagtcaaa      240
gagtttggag atgctggcca gtacacctgt cacaaaggag gcgaggttct aagccattcg      300
ctcctgctgc ttcacaaaaa ggaagatgga atttggtcca ctgatatttt aaaggaccag      360
aaagaaccca aaaataagac ctttctaaga tgcgaggcca agaattattc tggacgtttc      420
acctgctggt ggctgacgac aatcagtact gatttgacat tcagtgtcaa agcagcaga      480 ggctcttctg accccaagg ggtgacgtgc ggagctgcta cactctctgc agagagagtc      540
agagggacaa acaaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca aacctgaccc acccaagaac      720
ttgcagctga agccattaaa gaattctcgg caggtggagg tcagctggga gtaccctgac      780
acctggagta ctccacattc ctacttctcc ctgacattct gcgttcaggt ccagggcaag      840
agcaagagag aaaagaaaga tagagtcttc acgacaagaa cctcagccac ggtcatctgc      900
cgcaaaaatg ccagcattag cgtgcgggcc caggaccgct actatagctc atcttggagc      960
gaatgggcat ctgtgccctg cagttag                                          987
```

```
<210> SEQ ID NO 29
<211> LENGTH: 328
<212> TYPE: PRT
<213> ORGANISM: Artificial Sequence
<220> FEATURE:
<223> OTHER INFORMATION: IL-12 p40 aa

<400> SEQUENCE: 29
```

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
                275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 30
<211> LENGTH: 1233
<212> TYPE: DNA
<213> ORGANISM: Artificial Sequence
<220> FEATURE:
<223> OTHER INFORMATION: HER2 CAR (Fce)

<400> SEQUENCE: 30

```
atggactgga tctggcggat tctgtttctc gtgggagctg ccacaggcgc tcattctgct    60
cagcctgccg acatccagat gacccagagc cccagcagcc tgagcgccag cgtgggcgac   120
agagtgacca tcacctgcag agccagccag gacgtgaaca ccgccgtggc ctggtaccag   180
cagaagcccg gcaaggcccc caagctgctg atctacagcg ccagcttcct gtacagcggc   240
gtgcccagca gattcagcgg cagcagaagc ggcaccgact cacccctgac catcagcagc   300
ctgcagcccg aggacttcgc cacctactac tgccagcagc actacaccac cccccccacc   360
ttcggccagg gcaccaaggt ggagatcaag tcctcagggg gcgggggaag tggtggggc    420
ggcagcggcg gagggggctc aggaggaggc ggatcaggcg gatcagaggt gcagctggtg   480
gagagcggcg gcggcctggt gcagcccggc ggcagcctga ctgagctg cgccgccagc     540
ggcttcaaca tcaaggacac ctacatccac tgggtgagac aggcccccgg caagggcctg   600
gagtgggtgg ccagaatcta ccccaccaac ggctacacca gatacgccga cagcgtgaag   660
ggcagattca ccatcagcgc cgacaccagc aagaacaccg cctacctgca gatgaacagc   720
ctgagagccg aggacaccgc cgtgtactac tgcagcagat ggggcggcga cggcttctac   780
gccatggact actgggggca gggcaccctg gtgaccgtga gcagcgcggc cgcgctgagc   840
aacagcatca tgtacttcag ccacttcgtg cctgtgttcc tgcctgccaa gcctacaaca   900
acaccagccc ctagacctcc aaccctgcc ctacaattg cctctcagcc tctgtctctg    960
aggcccgaag cttgtagacc tgctgctggc ggagctgtgc acaccagagg actggatttc  1020
gcctgctttt gggtgctggt ggtcgtgggc ggagtgctgg cttgttattc tctgctggtc  1080
accgtggcct tcatcatctt ttgggtccga ctgaagatcc aggtccgaaa ggccgccatc  1140
accagctacg agaagtctga tggcgtgtac accggcctga gcaccagaaa ccaggaaacc  1200
tacgagacac tgaagcacga aagccccccc cag                                1233
```

<210> SEQ ID NO 31
<211> LENGTH: 536

```
<212> TYPE: PRT
<213> ORGANISM: Artificial Sequence
<220> FEATURE:
<223> OTHER INFORMATION: IL-12 single chain p40_p35 aa

<400> SEQUENCE: 31

Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Val Pro Gly Val Gly Val Pro Gly
                325                 330                 335

Val Gly Ala Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380
```

```
Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
            405                 410                 415

Arg Glu Thr Ser Phe Ile Thr Asn Gly Ser Cys Leu Ala Ser Arg Lys
        420                 425                 430

Thr Ser Phe Met Met Ala Leu Cys Leu Ser Ser Ile Tyr Glu Asp Ser
    435                 440                 445

Lys Met Tyr Gln Val Glu Phe Lys Thr Met Asn Ala Lys Leu Leu Met
450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
            485                 490                 495

Lys Ser Ser Leu Glu Glu Pro Asp Phe Tyr Lys Thr Lys Ile Lys Leu
        500                 505                 510

Cys Ile Leu Leu His Ala Phe Arg Ile Arg Ala Val Thr Ile Asp Arg
    515                 520                 525

Val Met Ser Tyr Leu Asn Ala Ser
530                 535

<210> SEQ ID NO 32
<211> LENGTH: 1611
<212> TYPE: DNA
<213> ORGANISM: Artificial Sequence
<220> FEATURE:
<223> OTHER INFORMATION: IL-12 single chain p40_p35 nt

<400> SEQUENCE: 32
atgggtcacc agcagttggt catctcttgg tttttccctgg ttttttctggc atctccsctc      60 gtggccatat gggaactgaa gaaagatgtt tatgtcgtag aattggattg gtatccggat     120
gcccctggag aaatggtggt cctcacctgt gacacccctg aagaagatgg tatcacctgg     180
accttggacc agagcagtga ggtcttaggc tctggcaaaa ccctgaccat ccaagtcaaa     240
gagtttggag atgctggcca gtacacctgt cacaaaggag cgaggttct aagccattcg      300 ctcctgctgc ttcacaaaaa ggaagatgga atttggtcca ctgatatttt aaaggaccag     360
aaagaaccca aaaataagac cttttctaaga tgcgaggcca agaattattc tggacgtttc     420
acctgctggt ggctgacgac aatcagtact gatttgacat tcagtgtcaa aagcagcaga     480
ggctcttctg acccccaagg ggtgacgtgc ggagctgcta cactctctgc agagagagtc     540
agaggggaca acaaggagta tgagtactca gtggagtgcc aggaggacag tgcctgccca     600
gctgctgagg agagtctgcc cattgaggtc atggtggatg ccgttcacaa gctcaagtat     660
gaaaactaca ccagcagctt cttcatcagg gacatcatca aacctgaccc acccaagaac     720
ttgcagctga agccattaaa gaattctcgg caggtggagg tcagctggga gtaccctgac     780
acctggagta ctccacattc ctacttctcc ctgacattct gcgttcaggt ccagggcaag     840
agcaagagag aaaagaaaga tagagtcttc acggacaaga cctcagccac ggtcatctgc     900
cgcaaaaatg ccagcattag cgtgcgggcc caggaccgct actatagctc atcttggagc     960
gaatgggcat ctgtgccctg cagtgttcct ggagtagggg tacctggggt gggcgccaga    1020
aacctccccg tggccactcc agacccagga atgttcccat gccttcacca ctcccaaaac    1080
ctgctgaggg ccgtcagcaa catgctccag aaggccagac aaaactctag attttaccct    1140
tgcacttctg aagagattga tcatgaagat atcacaaaag ataaaaccag cacagtggag    1200
```

```
gcctgtttac cattggaatt aaccaagaat gagagttgcc taaattccag agagacctct    1260
ttcataacta atgggagttg cctggcctcc agaaagacct cttttatgat ggccctgtgc    1320
cttagtagta tttatgaaga ctcgaagatg taccaggtgg agttcaagac catgaatgca    1380
aagcttctga tggatcctaa gaggcagatc tttctagatc aaaacatgct ggcagttatt    1440
gatgagctga tgcaggccct gaatttcaac agtgagactg tgccacaaaa atcctccctt    1500
gaagaaccgg atttttataa aactaaaatc aagctctgca tacttcttca tgctttcaga    1560
attcgggcag tgactattga tagagtgatg agctatctga atgcttccta a             1611
```

<210> SEQ ID NO 33
<211> LENGTH: 1215
<212> TYPE: DNA
<213> ORGANISM: Artificial Sequence
<220> FEATURE:
<223> OTHER INFORMATION: EGFR CAR (Fce)

<400> SEQUENCE: 33

```
atggactgga tctggcggat tctgtttctc gtgggagctg ccacaggcgc tcattctgct     60
cagcctgccg atattcttct tactcaatct cccgttattt tgtcagtatc ccaggtgag    120 cgagtcagct tctcttgtcg agcgtcacaa tccattggca ccaacataca ttggtaccaa    180
cagcgcacca acgggtctcc ccggctcttg attaagtacg catcagaaag tatttctggg    240
atacccagta ggttctcagg agcgggagt ggcactgact ttaccctgtc cataaacagc    300
gttgagtctg aggacatcgc ggactactat tgtcagcaga acaacaattg gccgaccacg    360
tttggtgcgg gaacaaaact tgaactcaaa ggcggcggag aagcggagg cggaggatct    420 ggggggcggag gctctggcgg aggggggatct caggtgcagc tcaaacagtc aggacctggc    480
ctcgttcagc caagccaatc actgagtata acgtgcacgg tgagcggctt tagcctgaca    540
aactatggtg tccactgggt ccgccaatct cctggaaaag gcttggagtg gctcggtgtt    600
atctggtccg gtggtaacac agactacaac acgccattca ccagtcgcct tagtattaac    660
aaggacaact ccaagtctca ggttttcttt aaaatgaact ctctgcagtc taatgatacc    720
gcaatttact actgtgcgag ggcactcacg tactatgact atgagttcgc gtattgggggc    780 caagggactc tcgttactgt ctcagcggcg gccgcgctga gcaacagcat catgtacttc    840
agccacttcg tgcctgtgtt cctgcctgcc aagcctacaa caacaccagc ccctagacct    900 ccaaccctg cccctacaat tgcctctcag cctctgtctc tgaggcccga agcttgtaga    960
cctgctgctg gcggagctgt gcacaccaga ggactggatt cgcctgcttt tgggtgctg    1020 gtggtcgtgg gcggagtgct ggcttgttat tctctgctgg tcaccgtggc cttcatcatc    1080
ttttgggtcc gactgaagat ccaggtccga aaggccgcca tcaccagcta cgagaagtct    1140
gatggcgtgt acaccggcct gagcaccaga aaccaggaaa cctacgagac actgaagcac    1200
gagaagcccc cccag                                                     1215
```

<210> SEQ ID NO 34
<211> LENGTH: 477
<212> TYPE: DNA
<213> ORGANISM: Artificial Sequence
<220> FEATURE:
<223> OTHER INFORMATION: TGF-beta receptor II extracellular domain nt

<400> SEQUENCE: 34

```
atgggtcggg ggctgctcag gggcctgtgg ccgctgcaca tcgtcctgtg gacgcgtatc     60
```

```
gccagcacga tcccaccgca cgttcagaag tcggttaata acgacatgat agtcactgac    120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga ggaaaaaaaa aaagcctggt gagactttct tcatgtgttc ctgtagctct    420
gatgagtgca atgacaacat catcttctca gaagaatata acaccagcaa tcctgac      477
```

<210> SEQ ID NO 35
<211> LENGTH: 159
<212> TYPE: PRT
<213> ORGANISM: Artificial Sequence
<220> FEATURE:
<223> OTHER INFORMATION: TGF-beta receptor II extracellular domain aa

<400> SEQUENCE: 35

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp
145                 150                 155
```

<210> SEQ ID NO 36
<211> LENGTH: 933
<212> TYPE: DNA
<213> ORGANISM: Artificial Sequence
<220> FEATURE:
<223> OTHER INFORMATION: TGF-beta trap nt

<400> SEQUENCE: 36

```
atgggtcggg gctgctcag gggcctgtgg ccgctgcaca tcgtcctgtg gacgcgtatc     60
gccagcacga tcccaccgca cgttcagaag tcggttaata acgacatgat agtcactgac    120
aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga ggaaaaaaaa aaagcctggt gagactttct tcatgtgttc ctgtagctct    420
gatgagtgca atgacaacat catcttctca gaagaatata acaccagcaa tcctgacgga    480
```

-continued

```
ggtggaggaa gtggaggagg tggaagtggt ggtggaggta gtacgatccc accgcacgtt    540
cagaagtcgg ttaataacga catgatagtc actgacaaca acggtgcagt caagtttcca    600
caactgtgta aattttgtga tgtgagattt tccacctgtg acaaccagaa atcctgcatg    660
agcaactgca gcatcacctc catctgtgag aagccacagg aagtctgtgt ggctgtatgg    720
agaaagaatg acgagaacat aacactagag acagtttgcc atgaccccaa gctcccctac    780
catgacttta ttctggaaga tgctgcttct ccaaagtgca ttatgaagga aaaaaaaaag    840
cctggtgaga ctttcttcat gtgttcctgt agctctgatg agtgcaatga caacatcatc    900
ttctcagaag aatataacac cagcaatcct gac                                 933

<210> SEQ ID NO 37
<211> LENGTH: 311
<212> TYPE: PRT
<213> ORGANISM: Artificial Sequence
<220> FEATURE:
<223> OTHER INFORMATION: TGF-beta trap aa

<400> SEQUENCE: 37

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Gly
145                 150                 155                 160

Gly Gly Gly Ser Gly Gly Gly Gly Ser Gly Gly Gly Gly Ser Thr Ile
                165                 170                 175

Pro Pro His Val Gln Lys Ser Val Asn Asn Asp Met Ile Val Thr Asp
            180                 185                 190

Asn Asn Gly Ala Val Lys Phe Pro Gln Leu Cys Lys Phe Cys Asp Val
        195                 200                 205

Arg Phe Ser Thr Cys Asp Asn Gln Lys Ser Cys Met Ser Asn Cys Ser
    210                 215                 220

Ile Thr Ser Ile Cys Glu Lys Pro Gln Glu Val Cys Val Ala Val Trp
225                 230                 235                 240

Arg Lys Asn Asp Glu Asn Ile Thr Leu Glu Thr Val Cys His Asp Pro
                245                 250                 255

Lys Leu Pro Tyr His Asp Phe Ile Leu Glu Asp Ala Ala Ser Pro Lys
            260                 265                 270

Cys Ile Met Lys Glu Lys Lys Lys Pro Gly Glu Thr Phe Phe Met Cys
```

```
            275                 280                 285
Ser Cys Ser Ser Asp Glu Cys Asn Asp Asn Ile Ile Phe Ser Glu Glu
            290                 295                 300

Tyr Asn Thr Ser Asn Pro Asp
305                 310

<210> SEQ ID NO 38
<211> LENGTH: 510
<212> TYPE: DNA
<213> ORGANISM: Artificial Sequence
<220> FEATURE:
<223> OTHER INFORMATION: erIL-15 nt

<400> SEQUENCE: 38
atgcgcatca gcaagcccca cctgcgcagc atcagcatcc agtgctacct gtgcctgctg     60
ctgaacagcc acttcctgac cgaggccggc atccacgtgt tcatcctggg ctgcttcagc    120
gccggcctgc ccaagaccga ggccaactgg gtgaacgtga tcagcgacct gaagaagatc    180
gaggacctga tccagagcat gcacatcgac gccaccctgt acaccgagag cgacgtgcac    240
cccagctgca aggtgaccgc catgaagtgc ttcctgctgg agctgcaggt gatcagcctg    300
gagagcggcg acgccagcat ccacgacacc gtggagaacc tgatcatcct ggccaacaac    360
agcctgagca gcaacggcaa cgtgaccgag agcggctgca aggagtgcga ggagctggag    420
gagaagaaca tcaaggagtt cctgcagagc ttcgtgcaca tcgtgcagat gttcatcaac    480
accagcggct ccgagaagga cgagctgtaa                                     510

<210> SEQ ID NO 39
<211> LENGTH: 169
<212> TYPE: PRT
<213> ORGANISM: Artificial Sequence
<220> FEATURE:
<223> OTHER INFORMATION: erIL-15 aa

<400> SEQUENCE: 39

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Ser Glu Lys Asp Glu Leu
                165
```

<210> SEQ ID NO 40
<211> LENGTH: 807
<212> TYPE: DNA
<213> ORGANISM: Artificial Sequence
<220> FEATURE:
<223> OTHER INFORMATION: Codon-optimized EGFR scFv - DNA sequence

<400> SEQUENCE: 40

```
atggactgga tctggcggat tctgtttctc gtgggagctg ccacaggcgc tcattctgct      60
cagcctgccg atattcttct tactcaatct cccgttattt tgtcagtatc cccaggtgag     120
cgagtcagct tctcttgtcg agcgtcacaa tccattggca ccaacataca ttggtaccaa     180
cagcgcacca acgggtctcc ccggctcttg attaagtacg catcagaaag tatttctggg     240
atacccagta ggttctcagg gagcgggagt ggcactgact ttaccctgtc cataaacagc     300
gttgagtctg aggacatcgc ggactactat tgtcagcaga caacaattg gccgaccacg      360
tttggtgcgg gaacaaaact tgaactcaaa ggcggcggag aagcggagg cggaggatct      420
ggggggcggag gctctggcgg aggggggatct caggtgcagc tcaaacagtc aggacctggc     480
ctcgttcagc caagccaatc actgagtata acgtgcacgg tgagcggctt agcctgaca      540
aactatggtg tccactgggt ccgccaatct cctggaaaag gcttggagtg gctcggtgtt     600
atctggtccg gtggtaacac agactacaac acgccattca ccagtcgcct tagtattaac     660
aaggacaact ccaagtctca ggttttcttt aaaatgaact ctctgcagtc taatgatacc     720
gcaatttact actgtgcgag ggcactcacg tactatgact atgagttcgc gtattggggc     780
caagggactc tcgttactgt ctcagcg                                          807
```

<210> SEQ ID NO 41
<211> LENGTH: 269
<212> TYPE: PRT
<213> ORGANISM: Artificial Sequence
<220> FEATURE:
<223> OTHER INFORMATION: EGFR scFv - Protein sequence

<400> SEQUENCE: 41

Met Asp Trp Ile Trp Arg Ile Leu Phe Leu Val Gly Ala Ala Thr Gly
1               5                   10                  15

Ala His Ser Ala Gln Pro Ala Asp Ile Leu Leu Thr Gln Ser Pro Val
            20                  25                  30

Ile Leu Ser Val Ser Pro Gly Glu Arg Val Ser Phe Ser Cys Arg Ala
        35                  40                  45

Ser Gln Ser Ile Gly Thr Asn Ile His Trp Tyr Gln Gln Arg Thr Asn
    50                  55                  60

Gly Ser Pro Arg Leu Leu Ile Lys Tyr Ala Ser Glu Ser Ile Ser Gly
65                  70                  75                  80

Ile Pro Ser Arg Phe Ser Gly Ser Gly Ser Gly Thr Asp Phe Thr Leu
                85                  90                  95

Ser Ile Asn Ser Val Glu Ser Glu Asp Ile Ala Asp Tyr Tyr Cys Gln
            100                 105                 110

Gln Asn Asn Asn Trp Pro Thr Thr Phe Gly Ala Gly Thr Lys Leu Glu
        115                 120                 125

Leu Lys Gly Gly Gly Gly Ser Gly Gly Gly Gly Ser Gly Gly Gly Gly
    130                 135                 140

Ser Gly Gly Gly Gly Ser Gln Val Gln Leu Lys Gln Ser Gly Pro Gly
145                 150                 155                 160

Leu Val Gln Pro Ser Gln Ser Leu Ser Ile Thr Cys Thr Val Ser Gly

```
                165                 170                 175
    Phe Ser Leu Thr Asn Tyr Gly Val His Trp Val Arg Gln Ser Pro Gly
                    180                 185                 190

Lys Gly Leu Glu Trp Leu Gly Val Ile Trp Ser Gly Gly Asn Thr Asp
                    195                 200                 205

Tyr Asn Thr Pro Phe Thr Ser Arg Leu Ser Ile Asn Lys Asp Asn Ser
            210                 215                 220

Lys Ser Gln Val Phe Phe Lys Met Asn Ser Leu Gln Ser Asn Asp Thr
    225                 230                 235                 240

Ala Ile Tyr Tyr Cys Ala Arg Ala Leu Thr Tyr Tyr Asp Tyr Glu Phe
                    245                 250                 255

Ala Tyr Trp Gly Gln Gly Thr Leu Val Thr Val Ser Ala
                260                 265

<210> SEQ ID NO 42
<211> LENGTH: 825
<212> TYPE: DNA
<213> ORGANISM: Artificial Sequence
<220> FEATURE:
<223> OTHER INFORMATION: Codon-optimized HER2/neu scFv - DNA sequence

<400> SEQUENCE: 42
atggactgga tctggcggat tctgtttctc gtgggagctg ccacaggcgc tcattctgct      60
cagcctgccg acatccagat gacccagagc cccagcagcc tgagcgccag cgtgggcgac     120
agagtgacca tcacctgcag agccagccag gacgtgaaca ccgccgtggc ctggtaccag     180
cagaagcccg gcaaggcccc caagctgctg atctacagcg ccagcttcct gtacagcggc     240
gtgcccagca gattcagcgg cagcagaagc ggcaccgact tcaccctgac catcagcagc     300
ctgcagcccg aggacttcgc cacctactac tgccagcagc actacaccac cccccccacc     360
ttcggccagg gcaccaaggt ggagatcaag tcctcagggg gcgggggaag tggtggggc      420 ggcagcggcg aggggggctc aggaggaggc ggatcaggcg atcagaggt gcagctggtg      480 gagagcggcg gcggcctggt gcagcccggc ggcagcctga ctgagctg cgccgccagc      540 ggcttcaaca tcaaggacac ctacatccac tgggtgagac aggcccccgg caagggcctg     600
gagtgggtgg ccagaatcta ccccaccaac ggctacacca atacgccga cagcgtgaag     660 ggcagattca ccatcagcgc cgacaccagc aagaacaccg cctacctgca gatgaacagc     720
ctgagagccg aggacaccgc cgtgtactac tgcagcagat ggggcggcga cggcttctac     780
gccatggact actggggcca gggcacccctg gtgaccgtga gcagc                    825

<210> SEQ ID NO 43
<211> LENGTH: 275
<212> TYPE: PRT
<213> ORGANISM: Artificial Sequence
<220> FEATURE:
<223> OTHER INFORMATION: HER2/neu scFv - Protein sequence

<400> SEQUENCE: 43

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
                20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60
```

```
Lys Ala Pro Lys Leu Leu Ile Tyr Ser Ala Ser Phe Leu Tyr Ser Gly
 65                  70                  75                  80

Val Pro Ser Arg Phe Ser Gly Ser Arg Ser Gly Thr Asp Phe Thr Leu
                 85                  90                  95

Thr Ile Ser Ser Leu Gln Pro Glu Asp Phe Ala Thr Tyr Tyr Cys Gln
                100                 105                 110

Gln His Tyr Thr Thr Pro Pro Thr Phe Gly Gln Gly Thr Lys Val Glu
                115                 120                 125

Ile Lys Ser Ser Gly Gly Gly Ser Gly Gly Gly Ser Gly Gly
130                 135                 140

Gly Gly Ser Gly Gly Gly Gly Ser Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
                180                 185                 190

Arg Gln Ala Pro Gly Lys Gly Leu Glu Trp Val Ala Arg Ile Tyr Pro
                195                 200                 205

Thr Asn Gly Tyr Thr Arg Tyr Ala Asp Ser Val Lys Gly Arg Phe Thr
                210                 215                 220

Ile Ser Ala Asp Thr Ser Lys Asn Thr Ala Tyr Leu Gln Met Asn Ser
225                 230                 235                 240

Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Leu Val Thr
                260                 265                 270

Val Ser Ser
275
```

CHIMERIC ANTIGEN RECEPTOR-MODIFIED NK-92 CELLS TARGETING EGFR SUPER-FAMILY RECEPTORS

SEQUENCE LISTING

The content of the ASCII text file of the sequence listing named Seq_listing_20200127_b_ST25, which is 61 kb in size was created on Jan. 27, 2020 and electronically submitted via EFS-Web along with the application is incorporated by reference in its entirety.

FIELD OF THE INVENTION

The field of the invention is genetically modified immune competent cells that express a chimeric antigen receptor (CAR), and particularly modified NK-92 cells expressing a CAR with an Fc epsilon receptor gamma (FcεRIγ) signaling domain targeting an EGFR superfamily receptor.

BACKGROUND OF THE INVENTION

Natural killer (NK) cells are cytotoxic lymphocytes that constitute a significant component of the innate immune system. In most cases, NK cells represent about 10-15% of circulating lymphocytes, and bind and kill targeted cells, including virus-infected cells and many malignant cells. NK cell killing is non-specific with regard to particular antigens and can occur without prior immune sensitization. Killing of targeted cells is typically mediated by cytolytic proteins, including perforin, granzymes, and granulysin.

Autologous NK cells have been used as therapeutic entities. To that end, NK cells are isolated from the peripheral blood lymphocyte fraction of whole blood, expanded in cell culture to obtain sufficient numbers of cells, and then re-infused into a subject. Autologous NK cells have shown in at least some cases moderate effectiveness in both ex vivo therapy and in vivo treatment. However, isolation and growth of autologous NK cell is time and cost intensive. Moreover, autologous NK cell therapy is further limited by the fact that not all NK cells are cytolytic.

At least some of these difficulties can be overcome by use of NK-92 cells, which are a cytolytic cancer cell line which was discovered in the blood of a subject suffering from a non-Hodgkins lymphoma and then immortalized in vitro (Gong et al., *Leukemia* 8:652-658 (1994)). While NK-92 cells are NK cell derivatives, NK-92 cells lack the major of inhibitory receptors that are otherwise displayed by normal NK cells, and retain the majority of the activating receptors. NK-92 cells do not, however, attack normal cells nor do they elicit an unacceptable immune rejection response in humans. Due to these desirable characteristics, NK-92 cells were characterized in detail and explored as therapeutic agent in the treatment of certain cancers as is described, for example, in WO 1998/049268 or US 2002/068044.

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Such tumor-specific antigens may serve as markers for tumor phenotype. Tumor-specific antigens include cancer/testis-specific antigen (e.g. MAGE, BAGE, GAGE, PRAME and NY-ESO-1), melanocyte differentiation antigens (e.g. tyrosinase, Melan-A/MART, gp100, TRP-1 and TRP-2), mutated or aberrantly expressed antigens (e.g. MUM-1, CDK4, beta-catenin, gp100-in4, p15 and N-acetylglucos-aminyltransferase V), and antigens that are expressed at higher levels in tumors (e.g., CD19 and CD20).

Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The first generation of CARs used in T-cells contained one cytoplasmic signaling domain. For example, one version of a first-generation CAR in T-cells included a signaling domain from the Fc epsilon receptor gamma (FcεRIγ) which contained one ITAM, while another version contained the signaling domain from CD3ζ which contained three ITAMs. In vivo and in vitro studies showed that the CD3ζ CAR T-cells were more efficient at tumor eradication than FcεRIγ CAR T-cells (e.g., Haynes, et al. 2001, *J. Immunology* 166:182-187; Cartellieri, et al. 2010, *J. Biomed and Biotech*, Vol. 2010, Article ID 956304). Additional studies then revealed that certain costimulatory signals were required for full activation and proliferation of such recombinant T-cells, and second and third generation CARs combined multiple signaling domains in to a single CAR to enhance efficacy of the recombinant CAR T-cells. Due to their less desirable philological effects in the tested T-cells, first generation CARs and the FcεRIγ signaling domains were largely discarded in favor of the new, more efficient CARs using CD3ζ in combination with one or more additional signaling domains (e.g., Hermanson and Kaufman 2015, *Frontiers in Immunol.*, Vol. 6, Article 195).

More recently, selected CARs have also been expressed in NK cells. For example, CAR-modified NK-92 cells have used first generation CARs with only a CD3ζ intracellular signaling domain. Several antigens have been targeted by these first generation CAR-NK cells, including CD19 and CD20 for B cell lymphoma, ErbB2 for breast, ovarian, and squamous cell carcinoma, GD2 for neuroblastoma, and CD138 for multiple myeloma. Second generation CAR-NK cells from the NK-92 line have also been created for several antigens, including EpCAM for multiple carcinomas HLA-A2 EBNA3 complex for Epstein-Barr virus, CS1 for multiple myeloma, and ErbB2 for HER2 positive epithelial cancers. The most common intracellular costimulatory domain used alongside CD3ζ in second generation NK-92 CARs is CD28. However, the potential effect of the CD28 domain is unclear since NK cells do not naturally express CD28. Additional second generation CARs have incorporated the 4-1BB intracellular signaling domain along with CD3ζ to improve NK cell persistence. Others compared functionality of different intracellular domains using an ErbB2 scFv fused with CD3ζ alone, CD28 and CD3ζ, or 4-1BB and CD3ζ tested against breast cancer cells. They found that both of the second generation constructs improved killing compared to the first generation CARs and the CD28 and CD3ζ had 65% target lysis, the 4-1BB and CD3ζ lysed 62%, and CD3ζ alone killed 51% of targets. 4-1BB and CD28 intracellular domains were also compared in a recent study using anti-CD19 CARs expressed on NK-92 cells for B cell malignances. Still others found that CD3ζ/4-1BB constructs were less effective than CD3ζ/CD28 in cell killing and cytokine production, highlighting differential effects of CD28 and 4-1BB costimulatory domains.

Third generation NK-92 CARs were constructed of an anti-CD5 scFv with CD3ζ, CD28, and 4-1BB intracellular signaling domains and demonstrated specific and potent anti-tumor activity against a variety of T-cell leukemia and lymphoma cell lines and primary tumor cells. Such cells were also able to inhibit disease progression in xenograft mouse models of T cell Acute lymphoblastic leukemia (ALL) cell lines as well as primary tumor cells (*Transl Res.* 2017 September; 187: 32-43). In further examples, WO 2016/201304 and WO 2018/076391 teach use of third generation CD3ζ CARs expressed in NK cells and NK-92 cells.

However, NK cells (and particularly NK-92 cells) are often difficult to genetically modify as evidenced by numerous failures to engineer NK-92 cells to express an Fc receptor. Such difficulties are further compounded where NK-92 cells are transfected with multiple recombinant genes or relatively large recombinant nucleic acid payload for heterologous expression. Additionally, NK-92 cells also exhibit a significant lack of predictability with respect to recombinant expression of exogenous proteins (e.g., CD16). On a functional level, while exhibiting in most cases targeted cytotoxicity, most if not all CAR NK-92 cells require a high effector to target cell ratio.

In addition, even where cytotoxic cells expressing a CAR are relatively effective in vitro, various suppressive or inhibitory factors associated with the tumor microenvironment in vivo may reduce or even abrogate cytotoxicity of such cells. Similarly, and despite the expression of a CAR, such modified cells may not always be effective in targeting the tumor microenvironment.

Therefore, even though numerous recombinant NK-92 cells are known in the art, all or almost all of them suffer from various difficulties. Consequently, there remains a need for CAR-expressing NK-92 cells that express a high-activity CAR in significant quantities, that can be readily cultivated in a simple and effective manner, and that have high cytotoxicity in a tumor microenvironment.

SUMMARY OF THE INVENTION

The inventors have discovered that natural killer (NK) cells, and particularly NK-92 cells, may be genetically modified to express a target-specific CAR and further recombinant proteins to increase CAR mediated cell killing, ADCC, and cytotoxicity in and/or homing to a tumor microenvironment. In addition, such recombinant cells also expressed cytokines for autocrine growth stimulation that advantageously assists in clonal selection of modified cells.

In one aspect of the inventive subject matter, the inventors contemplate a genetically modified NK cell (and especially an NK-92 cell) that expresses (i) a membrane bound recombinant chimeric antigen receptor (CAR) that comprises in a single polypeptide chain an extracellular binding domain, a hinge domain, a transmembrane domain, and a signaling domain, wherein the extracellular binding domain specifically binds to an EGFR superfamily receptor; (ii) a recombinant CD16; (iii) an autocrine growth stimulating cytokine; and (iv) optionally one of IL-12, a TGF-beta trap, or a homing receptor.

In some embodiments, the extracellular binding domain comprises a scFv, and/or the signaling domain comprises a FcεRIγ signaling domain. Most typically, the EGFR superfamily receptor is HER-2 or EGFR. In further contemplated aspects, the recombinant CD16 is a CD16158V mutant, and/or the autocrine growth stimulating cytokine is IL-2 or IL-15, which may additionally comprise an endoplasmic retention sequence. In still further contemplated embodiments, the IL-12 is a single chain IL-12 heterodimer, and the TGF-beta trap comprises a single chain dimer of the TGF-beta Receptor II ectodomain and is preferably secreted. Preferred homing receptors include cell adhesion molecules, selectins, integrins, a C—C chemokine receptor, or a C—X—C chemokine receptor. For example, suitable homing receptor include CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, DARC, and the receptor for CXCL14.

Viewed from a different perspective, genetically modified NK cells are contemplated that include a nucleic acid that encodes a (i) membrane bound recombinant chimeric antigen receptor (CAR) that comprises in a single polypeptide chain an extracellular binding domain, a hinge domain, a transmembrane domain, and a signaling domain, wherein the extracellular binding domain specifically binds to a EGFR superfamily receptor; (ii) a recombinant CD16; (iii) an autocrine growth stimulating cytokine; and (iv) optionally one of IL-12, a TGF-beta trap, or a homing receptor. With regard to the NK cell and the expressed proteins, the same considerations as noted above apply.

In another aspect of the inventive subject matter, the inventors also contemplate a method of treating cancer in a patient in need thereof in which the patient receives a therapeutically effective amount of the genetically modified NK cells presented herein, thereby treating the cancer. Where desired, contemplated methods may also include a step of administering at least one additional therapeutic entity selected from the group consisting of a viral cancer vaccine, a bacterial cancer vaccine, a yeast cancer vaccine, N-803, an antibody, a stem cell transplant, and a tumor targeted cytokine. For example, contemplated cancers include lung cancer, a breast cancer, a thyroid cancer, an esophageal cancer, a gastric cancer, a gastroesophageal cancer, or a head and neck cancer. Most typically, about $1 \times 10^8$ to about $1 \times 10^{11}$ cells per $m^2$ of body surface area of the patient are administered to the patient. Therefore, the inventors also contemplate use of a genetically modified NK cell in the treatment of cancer.

Various objects, features, aspects and advantages of the inventive subject matter will become more apparent from the following detailed description of preferred embodiments along with the accompanying drawing figures in which like numerals represent like components.

DETAILED DESCRIPTION OF THE INVENTION

The inventors have discovered that genetically modified NK cells can have significant general toxicity, target specific CAR-mediated cytotoxicity, and ADCC (antibody dependent cellular cytotoxicity), and that such genetically modified cells can be grown under autocrine growth stimulation that will also confer selective effect towards successfully transfected cells. In addition, contemplated cells may further express from a recombinant nucleic acid secreted IL-12 and/or a TGF-beta trap to reduce or eliminate an immune-suppressive environment. Additionally, or alternatively, contemplated cells may express from a recombinant nucleic acid a homing receptor. Therefore, modified cells may be generated by transfection with a tricistronic or quadracistronic nucleic acid.

It should be further appreciated that FcεRIγ-containing CARs have not been utilized in NK-92 cells, other NK cell lines, or endogenous NK cells as other signaling domains (e.g., CD3ζ) were deemed more efficient, especially when combined with additional signaling domains (in second and third generation CARs). Notably, the inventors have discovered that NK-92 cells expressing a first-generation CAR comprising an intracellular domain from FcεRIγ, which has only one ITAM domain, have equal or higher cytotoxic activity against cancer cells expressing the antigen recognized by the CAR than NK-92 cells expressing CARs with a CD3ζ signaling domain, which has three ITAM domains, even where these ITAM domains were combined with other signaling domains (i.e., second or third generation CARs). The inventors also made the unexpected finding that a CAR comprising an intracellular domain from FcεRIγ was expressed at higher levels on the surface of NK-92 cells than other CARs, especially those comprising the CD3ζ signaling domain. Cytotoxic effects can be even further enhanced by expression and secretion of IL-12, which reduces immune suppression in the tumor microenvironment (e.g., via exocrine stimulation of NK cells, modulation of MDSC, etc.), and/or by expression and secretion or presentation of a TGF-beta trap. Alternatively, or additionally, cytotoxic effects can also be enhanced by expression of one or more homing receptors to attract and/or retain NK cells in the tumor microenvironment.

Figure 1:
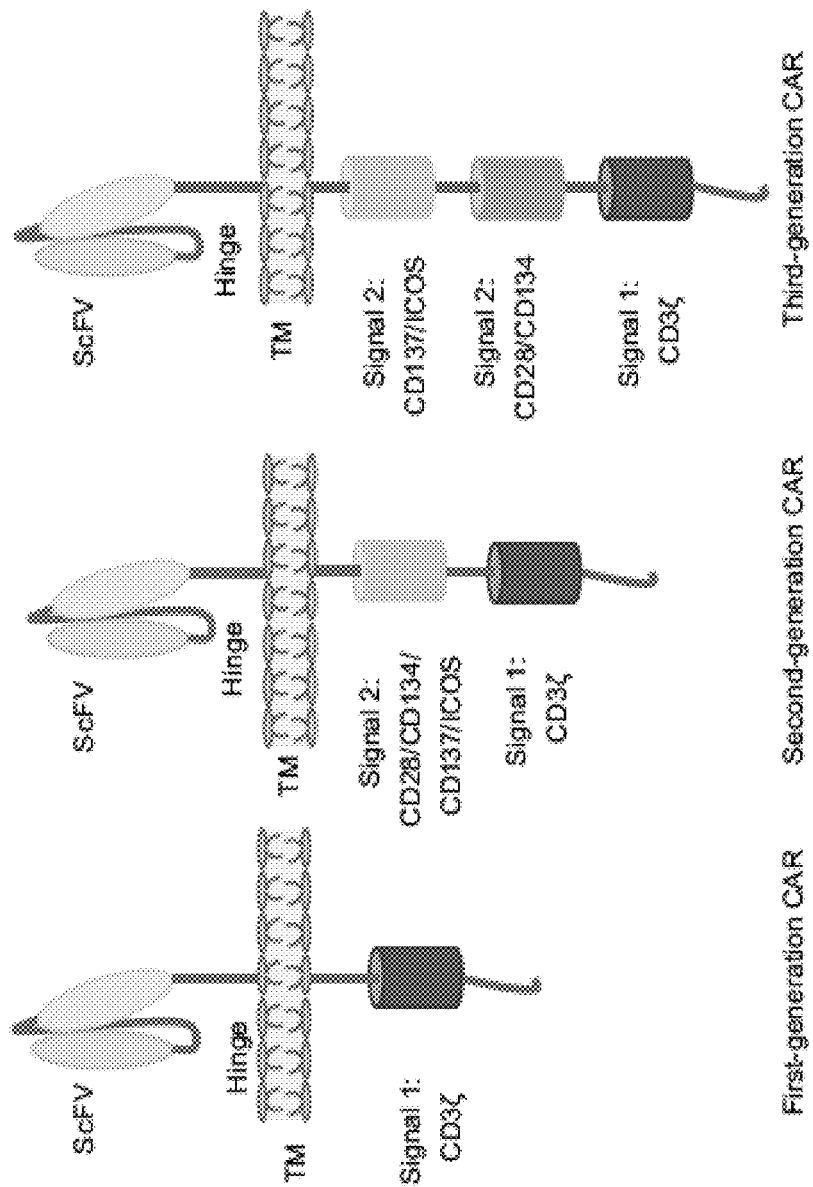
FIG. 1 is a schematic representation of exemplary CAR constructs. All CAR variants had an extracellular domain comprising an anti-EGFR superfamily receptor scFv region (e.g., αEGFR-scFv, αHER2-scFv), a hinge region from CD8 (CD8 hinge), and a transmembrane domain from CD28 (CD28 TM). The intracellular domains of the CD19CARs were varied as indicated.

Therefore, in some aspects of the inventive subject matter, a genetically modified NK-92 cell or NK cell line is engineered to express a chimeric antigen receptor (CAR) on a cell surface, and particularly a CAR that specifically binds to an EGFR superfamily receptor such as EGFR or HER2. Most typically, the CAR comprises an intracellular domain from the Fc epsilon receptor gamma (FcεRIγ). However, in further contemplated embodiments the CAR may also comprise a T cell receptor (TCR) CD3ζ zeta (CD3ζ) intracellular domain, alone or in combination with additional components as are known from $2^{nd}$ and $3^{rd}$ generation CAR constructs (e.g., CD28, CD134, CD137, and/or ICOS). As will be readily appreciated, the CAR may be transiently or stably expressed by the NK-92 cell from a recombinant DNA or RNA molecule. Exemplary CAR constructs suitable for use herein are shown in FIG. 1.

Consequently, in one aspect of the inventive subject matter, an NK cell, an NK-92 cell or NK/NK-92 cell line expresses a chimeric antigen receptor (CAR) on the surface of the NK-92 cell that comprises a cytoplasmic domain of FcεRIγ (e.g., having amino acid sequence of SEQ ID NO:1). Alternatively, or additionally, the CAR may also comprise a cytoplasmic domain of CD3ζ zeta (e.g., having amino acid sequence of SEQ ID NO:7, which may be encoded by a nucleic acid of SEQ ID NO:8 (codon optimized)). In another aspect, an NK or NK-92 cell line is contemplated that is transformed with a nucleic acid encoding a chimeric antigen receptor (CAR). For example, preferred nucleic acids encode a cytoplasmic domain of FcεRIγ (e.g., comprising or consisting of SEQ ID NO:2). As discussed in more detail below, the CAR may target a EGFR superfamily receptor such as EGFR or HER2.

In further contemplated embodiments, the NK, NK-92, or other NK cell is modified to express an autocrine growth stimulating cytokine or variant thereof. For example, suitable cytokines may be transiently or stably expressed by the recombinant cell, and the cytokine may include an endoplasmic retention signal. Most typically (but not necessarily) a retention signal will reduce the amount of secreted cytokine and as such may act as an endocrine growth stimulus without producing systemic effects otherwise encountered by the cytokine expression. Beneficially, the nucleic acid sequence encoding the autocrine growth stimulating cytokine or variant thereof is located on the same recombinant nucleic acid, typically as part of a tri- or quadracistronic configuration. Consequently, recombinant cells transfected with the tri- or quadracistronic nucleic acid can be readily selected and propagated by virtue of their independence from otherwise needed exogenous IL-2.

Additionally, it is generally preferred that the genetically modified NK cells will also express a recombinant CD16 or high-affinity variant thereof (e.g., $CD16^{158V}$) to impart to the cells target specific ADCC. Advantageously, such co-expression with the CAR is thought to further increase cytotoxicity against a tumor cell. In this context, it should be appreciated that unmodified NK cells typically do not express CD16 and exhibit only cytotoxicity as a part of the innate immune system.

More recently it has been discovered that efficacy of immune therapy may be reduced or even entirely abolished by various factors present in the tumor microenvironment. For example, immune suppressive factors include among other players certain cytokines (e.g., TGF-beta) and various suppressive cells (e.g., MDSC). Consequently, genetically modified NK cells may further express one or more recombinant proteins to counteract the immune suppressive factors. For example, and as is described in more detail below, the genetically modified NK cells may express a TGF-beta trap to reduce TGF-beta mediated effects in the tumor microenvironment and/or may express IL-12 to suppress MDSCs. Additionally, or alternatively, the genetically modified NK cells may also express one or more homing receptors to the tumor microenvironment (or other desired tissue) to so increase the number of therapeutic cells in the tumor microenvironment and thus enhance the therapeutic effect.

In another aspect of the inventive subject matter, the inventors also contemplate a method of treating cancer in a patient in need thereof that includes a step of administering to the patient a therapeutically effective amount of modified NK/NK-92 cells or an NK/NK-92 cell line engineered to express a chimeric antigen receptor (CAR) as described herein. Viewed form a different perspective, the inventors also contemplate a modified NK/NK-92 cell or a NK/NK-92 cell line that expresses a chimeric antigen receptor (CAR), preferably comprising a cytoplasmic domain of FcεRIγ, for use in treating a tumor in a subject. In some embodiments, the use comprises administering to the subject effective amounts of modified cells or the cell line described herein to treat the tumor. In yet other embodiments, an in vitro method for killing tumor cells is contemplated and may include a step of contacting a tumor cell with a modified NK-92 cell or NK-92 cell line described herein. In some embodiments, the modified NK-92 cell or NK-92 cell line expresses a CAR that binds to an antigen on the tumor cell. In some embodiments, the CAR preferably comprises an intracellular domain from the Fc epsilon receptor gamma (FcεRIγ). Alternatively, or additionally, the CAR comprises a T cell receptor (TCR) CD3ζ zeta (CD3ζ) intracellular domain.

With respect to suitable NK cells, it should be noted that all NK cells are deemed suitable for use herein and therefore include primary NK cells (preserved, expanded, and/or fresh cells), secondary NK cells that have been immortalized, autologous or heterologous NK cells (banked, preserved, fresh, etc.), and modified NK cells as described in more detail below. In some embodiments, it is preferred that the NK cells are NK-92 cells. The NK-92 cell line is a unique cell line that was discovered to proliferate in the presence of interleukin 2 (IL-2) (see e.g., Gong et al., *Leukemia* 8:652-658 (1994)). NK-92 cells are cancerous NK cells with broad anti-tumor cytotoxicity and predictable yield after expansion in suitable culture media. Advantageously, NK-92 cells have high cytolytic activity against a variety of cancers.

The original NK-92 cell line expressed the $CD56^{bright}$, CD2, CD7, CD11a, CD45, and CD54 surface markers and did not display the CD1, CD3, CD4, CD5, CD8, CD10, CD14, CD16, CD19, CD20, CD23, and CD34 markers. Growth of such NK-92 cells in culture is dependent upon the presence of interleukin 2 (e.g., rIL-2), with a dose as low as 1 IU/mL being sufficient to maintain proliferation. IL-7 and IL-12 do not support long-term growth, nor have various other cytokines tested, including IL-1α, IL-6, tumor necrosis factor α, interferon α, and interferon γ. Compared to primary NK cells, NK-92 typically have a high cytotoxicity even at relatively low effector:target (E:T) ratios, e.g. 1:1. Representative NK-92 cells are deposited with the American Type Culture Collection (ATCC), designation CRL-2407.

Therefore, suitable NK cells may have one or more modified KIR that are mutated such as to reduce or abolish interaction with MEW class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells (activated natural killer cells). Such cells may then be additionally genetically modified to a CAR as further described in more detail below.

In another aspect of the inventive subject matter, the genetically engineered NK cell may also be an NK-92 derivative that is modified to express the high-affinity Fcγ receptor (CD16). Sequences for high-affinity variants of the Fcγ receptor are well known in the art (see e.g., *Blood* 2009 113:3716-3725; or SEQ ID NO:11 (with V at amino acid position 158) and SEQ ID NO:12 (with codon for V at amino acid position 158)), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells. Such cells may then be additionally genetically modified to a CAR as further described in more detail below.

Therefore, NK cells suitable for use herein include NK-92 cells (which may be transfected with a tricistronic or quadracistronic construct encoding a CAR, a CD16 or variant thereof, and a cytokine or variant thereof, and optionally one of IL-12, a TGF-beta trap, and a homing receptor), a genetically modified NK cell or NK-92 cell that expresses a CD16 or variant thereof or a cytokine or variant thereof (which may be transfected with a nucleic acid encoding a CAR and a CD16 or variant thereof or a cytokine or variant thereof), and a genetically modified NK cell or NK-92 cell that expresses a CD16 or variant thereof and a cytokine or variant thereof (which may be transfected with a nucleic acid encoding a CAR). As noted before, any of the NK cells contemplated herein may express one of IL-12, a TGF-beta trap, and a homing receptor from the same or a different recombinant nucleic acid.

Genetic modification of the NK cells contemplated herein can be performed in numerous manners, and all known manners are deemed suitable for use hereon. Moreover, it should be recognized that NK cells can be transfected with DNA or RNA, and the particular choice of transfection will at least in part depend on the type of desired recombinant cell and transfection efficiency. For example, where it is desired that NK cells are stably transfected, linearized DNA may be introduced into the cells for integration into the genome. On the other hand, where transient transfection is desired, circular DNA or linear RNA (e.g., mRNA with polyA$^+$ tail) may be used.

Similarly, it should be appreciated that the manner of transfection will at least in part depend on the type of nucleic acid employed. Therefore, viral transfection, chemical transfection, mechanical transfection methods are all deemed suitable for use herein. For example, in one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In another embodiment, vectors will preferably allow for stable transfection of cells. In one embodiment, the vector allows incorporation of the transgene(s) into the genome of the cell. Preferably, such vectors have a positive selection marker and suitable positive selection markers include any genes that allow the cell to grow under conditions that would kill a cell not expressing the gene. Non-limiting examples include antibiotic resistance, e.g. geneticin (Neo gene from Tn5). Alternatively, or additionally, the vector is a plasmid vector. In one embodiment, the vector is a viral vector. As would be understood by one of skill in the art, any suitable vector can be used, and suitable vectors are well-known in the art.

In still other embodiments, the cells are transfected with mRNA encoding the protein of interest (e.g., the CAR). Transfection of mRNA results in transient expression of the protein or proteins. In one embodiment, transfection of mRNA into NK-92 cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration. In at least some embodiments as described in more detail below, NK cell transfection with mRNA resulted in unexpectedly consistent and strong expression of the CAR at a high faction of transfected cells. Moreover, such transfected cells also exhibited a high specific cytotoxicity at comparably low effector to target cell ratios.

With respect to contemplated CARs it is noted that the NK/NK-92 cells will be genetically modified to express the CAR as a membrane bound protein exposing a portion of the CAR on the cell surface while maintaining the signaling domain in the intracellular space. Most typically, the CAR will include at least the following elements (in order): an extracellular binding domain, a hinge domain, a transmembrane domain, and a signaling domain (preferably, but not necessarily a FcεRIγ domain).

In preferred embodiments, the cytoplasmic domain of the CAR comprises or consists of a signaling domain of FcεRIγ. For example, the FcεRIγ signaling domain comprises or consists of or consists essentially of the amino acid sequence of SEQ ID NO:1. In some embodiments, the FcεRIγ cytoplasmic domain is the sole signaling domain. However, it should be appreciated that additional elements may also be included, such as other signaling domains (e.g., CD28 signaling domain, CD3ζ signaling domain, 4-1BB signaling domain, etc.). These additional signaling domains may be positioned downstream of the FcεRIγ cytoplasmic domain and/or upstream of the FcεRIγ cytoplasmic domain.

In some embodiments, the FcεRIγ signaling domain comprises or consists of or consists essentially of an amino acid sequence having at least about 85%, 90%, 95%, 96%, 97%, 98%, or 99% sequence homology to the amino acid sequence of SEQ ID NO:1.

As noted above, in some embodiments, the cytoplasmic domain of the CAR comprises a signaling domain of CD3 zeta (CD3ζ). In one embodiment, the cytoplasmic domain of the CAR consists of a signaling domain of CD3 zeta. In one embodiment, the CD3 zeta signaling domain comprises or consists of or consists essentially of the amino acid sequence of SEQ ID NO:7. In some embodiments, the CD3 zeta signaling domain comprises or consists of or consists essentially of an amino acid sequence having at least about 85%, 90%, 95%, 96%, 97%, 98%, or 99% sequence homology to the amino acid sequence of SEQ ID NO:7.

The CAR may comprise any suitable transmembrane domain. In one aspect, the CAR comprises a transmembrane domain of CD28. In one embodiment, the CD28 transmembrane domain comprises or consists of or consists essentially of the amino acid sequence of SEQ ID NO:4. In one embodiment, the CD28 transmembrane domain comprises or consists of or consists essentially of an amino acid sequence having at least about 85%, 90%, 95%, 96%, 97%, 98%, or 99% sequence homology to the amino acid sequence of SEQ ID NO:4. In one embodiment, the transmembrane domain is selected from a CD28 transmembrane domain, 4-1BB transmembrane domain, or FcεRIγ transmembrane domain.

The CAR may comprise any suitable hinge region. In one aspect, the CAR comprises a hinge region of CD8. In one embodiment, the CD8 hinge region comprises or consists of or consists essentially of the amino acid sequence of SEQ ID NO:3. In one embodiment, the CD8 hinge region comprises or consists of or consists essentially of an amino acid sequence having at least about 85%, 90%, 95%, 96%, 97%, 98%, or 99% sequence homology to the amino acid sequence of SEQ ID NO:3.

Most typically, but not necessarily, the extracellular binding domain of the CAR will be a scFv or other natural or synthetic binding portion that specifically binds an antigen of interest such as an EGFR superfamily receptor (and particularly EGFR or HER2). Especially suitable binding portions include small antibody fragments with single, dual, or multiple target specificities, beta barrel domain binders, page display fusion proteins, etc. However, in other embodiments, suitable extracellular binding domains will specifically bind to a tumor-specific antigen, a tumor associated antigen, or a patient- and tumor-specific antigen. For example, contemplated antigens include CD19, CD20, GD2, HER-2, CD30, EGFR, FAP, CD33, CD123, PD-L1, IGF1R, CSPG4, or B7-H4. Further tumor-specific antigens are described, by way of non-limiting example, in US2013/0189268; WO 1999024566 A1; U.S. Pat. No. 7,098,008; and WO 2000020460, each of which is incorporated herein by reference in its entirety.

Therefore, contemplated CARs will generally have a structure of an extracellular binding domain that is (directly) coupled to a hinge domain, which is (directly) coupled to a transmembrane domain, which is (directly) coupled to a (e.g., FcεRIγ) signaling domain. In still further contemplated aspects, contemplated CARs may also include one or more signaling domains in addition to or replacing the FcεRIγ signaling domain, and especially contemplated signaling domains include CD3ζ signaling domains, 4-1BB signaling domains, and CD28 signaling domains. For example, contemplated CAR polypeptides may therefore include any one of the binding domains having SEQ ID NO:41 (EGFR scFv—amino acid sequence; encoded by a nucleic having SEQ ID NO:40, or a sequence having at least 90%, or at least 95% or at least 96%, or at least 97%, or at least 98%, or at least 99% identity to SEQ ID NO:40) and SEQ ID NO:43 (HER2/neu scFv—amino acid sequence; encoded by a nucleic having SEQ ID NO:42, or a sequence having at least 90%, or at least 95% or at least 96%, or at least 97%, or at least 98%, or at least 99% identity to SEQ ID NO:42) that is coupled to a hinge domain (e.g., CD8 hinge as in SEQ ID NO:3), which is in turn coupled to a transmembrane domain (e.g., CD28 TM as in SEQ ID NO:4), which is coupled to a signaling domain (e.g., FcεRIγ signaling domain as in SEQ ID NO:1, CD28 signaling domain as in SEQ ID NO:5, 4-1BB signaling domain as in SEQ ID NO:6, and/or CD3ζ signaling domain as in SEQ ID NO:7)

With respect to the construction of contemplated CARs it should be recognized that CARs can be engineered in numerous manners as described, for example, in WO 2014/039523; US 2014/0242701; US 2014/0274909; US 2013/0280285 and WO 2014/099671, each of which is incorporated herein by reference in its entirety.

Viewed from a different perspective, contemplated CARs target an antigen associated with a specific cancer type, and more particularly cancers that overexpress EGFR and/or HER2 such as lung cancer (e.g., small cell) and breast cancer (e.g., TBNC), thyroid cancer, esophageal cancer, gastric cancer, gastroesophageal cancer, head and neck cancer, etc.

In still further contemplated aspects, NK cells may be further genetically modified to express one or more cytokines, and especially an autocrine growth stimulating cytokine to so provide a selection marker where the cytokine and the CAR are encoded on the same recombinant nucleic acid and/or to render the recombinant cells independent of exogenous IL-2. Therefore, in some embodiments, NK-92 cells are modified to express at least one cytokine. In particular, the at least one cytokine is IL-2, IL-12, IL-15, IL-18, IL-21, or a variant thereof. In preferred embodiments, the cytokine is IL-2 or a variant thereof and especially preferred variants include endoplasmic retention signals (e.g., human IL-2 polypeptide as in SEQ ID NO:9, optionally with ER retention signal as in SEQ ID NO:10). For example, the IL-2 gene is cloned and expressed with a signal sequence that directs the IL-2 to the endoplasmic reticulum. This permits expression of IL-2 at levels sufficient for autocrine activation, but without releasing IL-2 extracellularly (e.g., *Exp Hematol.* 2005 February; 33(2):159-64.) Alternatively, expression of a cytokine (and especially IL-15) may also be such that the cytokine will be expressed in sufficient quantities to provide an autocrine growth signal to the recombinant cells, but also to allow at least some of the expressed IL-15 to be released from the cell, which will so provide an immune stimulatory signal. For example, such expression may be achieved using a human IL-15 sequence that includes both the signal peptide and an endoplasmic retention sequence. An exemplary DNA and protein sequence for an endoplasmic retained IL-15 is shown in SEQ ID NO:38 and SEQ ID NO:39, respectively.

Where desired, contemplated cells may also express a suicide gene. The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92 cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir. In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood.* 1998 Jul. 15; 92(2):672-82. In a further embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46. In yet another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Where the modified NK cells are further engineered to express IL-12, it is generally preferred that the IL-12 is expressed as a single chain heterodimer in which the p35 and p40 components are linked together by a flexible linker (in either orientation, p35-linker-p40 or p40-linker-p35). Moreover, it is generally preferred that the heterodimer will be secreted and as such may include a signal peptide for protein export. Therefore, suitable IL-12 sequences as contemplated herein may comprise a nucleic acid sequence with at least 80%, 85%, 90%, 91%, 92%, 93%, 94%, 95%, 96%, 97%, 98% or 99% identity to SEQ ID NO:26 (p35 n.t. sequence), or SEQ ID NO:28 (p40 n.t. sequence). The IL-12 contemplated herein may also comprise an amino acid sequence with at least 80%, 85%, 90%, 91%, 92%, 93%, 94%, 95%, 96%, 97%, 98% or 99% identity to SEQ ID NO:27 (p35 a.a. sequence, isoform 1 precursor), or SEQ ID NO:29 (p40 a.a. sequence, precursor). Thus, the IL-12 single chain p40 p35 sequence may comprise a polypeptide sequence with at least 80%, 85%, 90%, 91%, 92%, 93%, 94%, 95%, 96%, 97%, 98% or 99% identity to SEQ ID NO:31, or may comprise an polynucleotide sequence with at least 80%, 85%, 90%, 91%, 92%, 93%, 94%, 95%, 96%, 97%, 98% or 99% identity to SEQ ID NO:32. Most preferably, but not necessarily, the nucleic acid encoding the IL-12 single chain heterodimer will be part of a polycistronic nucleic acid sequence (e.g., present as a quadracistronic sequence with CAR, CD16, and erIL-2).

Where the modified NK cells are further engineered to express a TGF-beta trap, it is generally preferred that the TGF-beta trap is a single chain dimer of the extracellular domain of a TGFβRII molecule, and most preferably comprises a single chain dimer of the TGF-beta Receptor II ectodomain. Suitable TGF-beta traps are therefore encoded by a polynucleotide sequence with at least 80%, 85%, 90%, 91%, 92%, 93%, 94%, 95%, 96%, 97%, 98% or 99% identity to SEQ ID NO:34 (TGFBRII extracellular domain), or SEQ ID NO:36 (TGF beta trap sequence). The TGF-beta trap contemplated herein may also comprise an amino acid sequence with at least 80%, 85%, 90%, 91%, 92%, 93%, 94%, 95%, 96%, 97%, 98% or 99% identity to SEQ ID NO:35 (TGFBRII extracellular domain), or SEQ ID NO:37 (TGF-beta trap sequence). Other suitable TGF-beta traps include those described in *Mol. Canc. Ther.* 2012, Vol 11(7), 1477-1487. Most preferably, but not necessarily, the nucleic acid encoding the TGF-beta trap will be part of a polycistronic nucleic acid sequence (e.g., present as a quadracistronic sequence with CAR, CD16, and erIL-2).

Where the modified NK cells are further engineered to express a homing receptor it is noted that the term "homing receptor" refers to a receptor that activates a cellular pathway that results directly or indirectly in the cell migrating toward a target cell or tissue. For example, homing receptors expressed by leukocytes are used by leukocytes and lymphocytes to enter secondary lymphoid tissues via high endothelial venules. Homing receptors can also be used by cells to migrate toward the source of a chemical gradient, such as a chemokine gradient. Examples of homing receptors include G-protein coupled receptors such as chemokine receptors, including CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCXCKR, D6, and DARC; cytokine receptors; cell adhesion molecules such as selectins, including L-selectin (CD62L), integrins such as α4β7 integrin, LPAM-1, and LFA-1. Homing receptors generally bind to cognate ligands on the target tissues or cell. In some embodiments, homing receptors bind to addressins on the endothelium of venules, such as mucosal vascular addressing cell adhesion molecule 1 (MAdCAM-1).

In some exemplary embodiments, the chemokines and homing receptors contemplated herein may comprise a polypeptide sequence or a polynucleotide sequence having at least 80%, 85%, 90%, 91%, 92%, 93%, 94%, 95%, 96%, 97%, 98% or 99% identity to SEQ ID NO:13 (CCR7 n.t. sequence), or SEQ ID NO:14 (CCL19 n.t. sequence), or SEQ ID NO:15 (CCL21 n.t. sequence), or SEQ ID NO:16 (CXCR2 n.t. sequence), or SEQ ID NO:17 (CXCR2 a.a. sequence), or SEQ ID NO:18 (CXCL14 n.t. sequence), or SEQ ID NO:19 (CXCL4 a.a. sequence), or SEQ ID NO:20 (CD62L n.t. sequence), or SEQ ID NO:21 (CD62L a.a. sequence), or SEQ ID NO:22 (IL-8 n.t. sequence), or SEQ ID NO:23 (IL-8 a.a. sequence), or SEQ ID NO:24 (CXCL1 n.t. sequence), or SEQ ID NO:25 (CXCL1 a.a. sequence). Most preferably, but not necessarily, the nucleic acid encoding the homing receptor will be part of a polycistronic nucleic acid sequence (e.g., present as a quadracistronic sequence with CAR, CD16, and erIL-2).

Of course, it should be noted that all of the recombinant proteins can be expressed from individual recombinant sequences. However, it is generally preferred that where multiple recombinant sequences are expressed (e.g., CAR, CD16, cytokine, TGF-beta trap), coding regions may be arranged in a polycistronic unit with at least two or at least three or at least four coding regions encoding the recombinant proteins. Therefore, transgenes can be engineered into an expression vector by any mechanism known to those of skill in the art. Where multiple transgenes are to be inserted into a cell, transgenes may be engineered into the same expression vector or a different expression vector. In some embodiments, the cells are transfected with mRNA encoding the transgenic protein to be expressed. In some embodiments, the cells are transfected with DNA encoding the transgenic protein to be expressed. Transgenes, mRNA and DNA can be introduced into the NK-92 cells using any transfection method known in the art, including, by way of non-limiting example, infection, viral vectors, electroporation, lipofection, nucleofection, or "gene-gun."

In preferred embodiments, it should therefore be noted that the genetically modified NK cell (especially where the cell expresses a CAR and CD16 or variant thereof) will exhibit three distinct modes of cell killing: General cytotoxicity which is mediated by activating receptors (e.g., an NKG2D receptor), ADCC which is mediated by antibodies bound to a target cell, and CAR mediated cytotoxicity. Where desired, therapeutic effect in the tumor microenvironment may be further increased via expression and secretion of IL-12 (e.g., as a single chain heterodimer), via expression and presentation/secretion of a TGF-beta trap (e.g., as a single chain dimer of the TGF-beta Receptor II ectodomain) or via expression of a homing receptor (e.g., CCR7). As will be readily apparent, contemplated genetically modified cells can be used for treatment of various diseases, and especially of various cancers and viral infections where a diseased cell presents a disease-specific or disease-associated antigen. Consequently, the inventors contemplate methods of treating patients with modified NK or NK-92 cells as described herein. In one embodiment, the patient is suffering from cancer (e.g., a tumor) and the modified NK-92 cell or cell line expresses a CAR specific for an antigen expressed on the surface of a cell from the cancer or tumor. As noted above, in some embodiments, the cancer is lung cancer, a breast cancer, a thyroid cancer, an esophageal cancer, a gastric cancer, a gastroesophageal cancer, or a head and neck cancer.

Contemplated modified NK or NK-92 cells can be administered to an individual by absolute numbers of cells. For example, the individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per injection, or any ranges between any two of the numbers, end points inclusive. In other embodiments, modified NK-92 cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per kilogram of the individual, or any ranges between any two of the numbers, end points inclusive. In other embodiments, the total dose may be calculated by $m^2$ of body surface area, including about $1\times10^{11}$, $10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92 cells are administered to a patient.

Modified NK-92 cells, and optionally other anti-cancer agents can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the modified NK cells express a suicide gene, the patient is administered an agent to trigger modified NK cell death. In one embodiment, the agent is administered at a time point after administration of the modified NK cells that is sufficient for the NK cells to kill target cells.

In one embodiment, the modified NK cells are irradiated prior to administration to the patient. Irradiation of NK cells is described, for example, in U.S. Pat. No. 8,034,332, which is incorporated herein by reference in its entirety. In one embodiment, modified NK cells that have not been engineered to express a suicide gene are irradiated.

Furthermore, it should be appreciated that contemplated treatments will also include administration of other immune therapeutic entities, and especially preferred immune therapeutic entities include a viral cancer vaccine (e.g., adenoviral vector encoding cancer specific antigens), a bacterial cancer vaccine (e.g., non-pyrogenic E. coli expressing one or more cancer specific antigens), a yeast cancer vaccine, N-803 (also known as ALT-803, ALTOR Biosciences), an antibody (e.g., binding to a tumor associated antigen or patient specific tumor neoantigen), a stem cell transplant (e.g., allogeneic or autologous), and a tumor targeted cytokine (e.g., NHS-IL12, IL-12 coupled to a tumor targeting antibody or fragment thereof).

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before aspects of the present inventive subject matter are disclosed and described in more detail, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: HER2.CAR t-haNK Cells

Unless specified otherwise in the following examples, the inventors used NK-92 cells for all transfections of the cells with recombinant nucleic acids. Furthermore, and also unless noted otherwise, all recombinant nucleic acids were linearized DNA constructs encoding a tri- or quadracistronic configuration.

Figure 2:
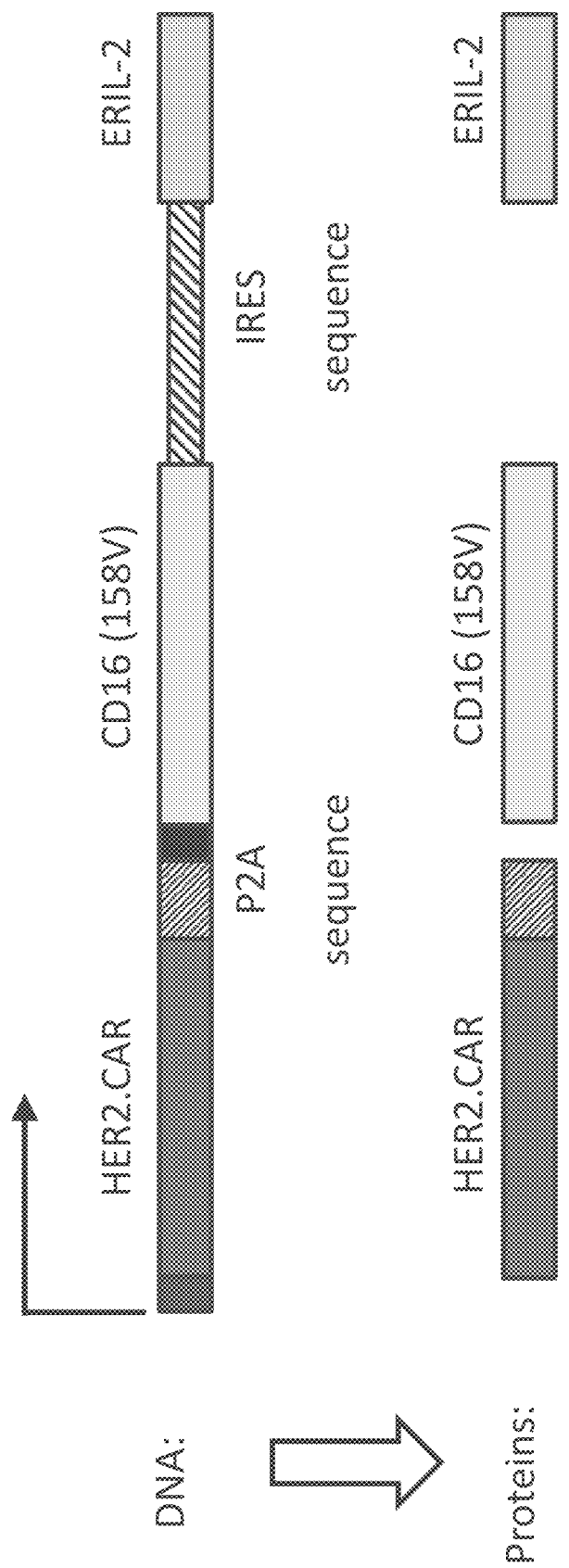
FIG. 2 is a schematic representation of an exemplary tricistronic recombinant nucleic acid encoding a HER2.CAR, followed by a P2A sequence, followed by a sequence encoding a high-affinity variant of CD16. The CD16 sequence is followed by an IRES sequence, which is followed in turn by a sequence encoding erIL-2.
Figure 3:
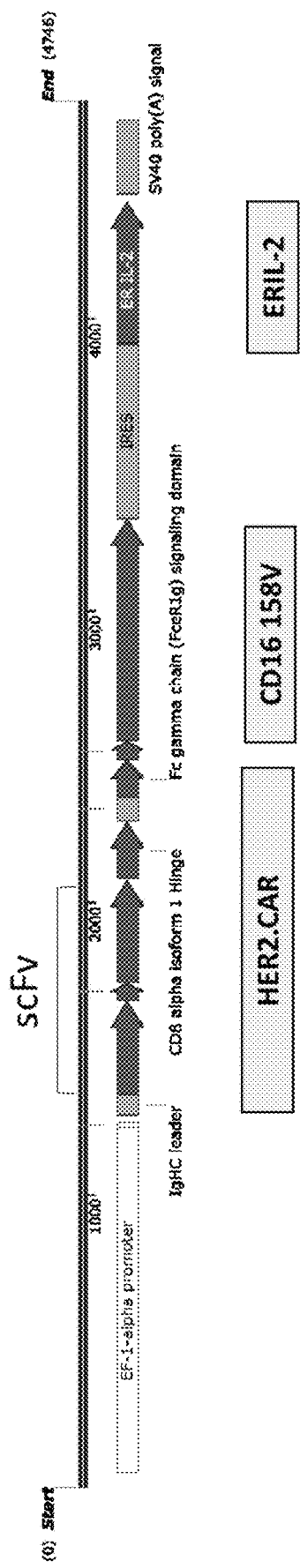
FIG. 3 is another schematic representation of an exemplary tricistronic recombinant nucleic acid encoding a HER2.CAR, a high-affinity variant of CD16, and erIL-2 used to generate recombinant NK cells.

To generate HER2.CAR t-haNK cells, a recombinant DNA molecule was assembled as is schematically depicted in FIG. 2 where the tricistronic configuration included a sequence encoding a HER2.CAR followed by a P2A sequence, which was followed by a sequence encoding CD16 (or $CD16^{158V}$), and which in turn was followed by an IRES sequence element upstream of a sequence encoding erIL-2. Unless otherwise noted, the HER2.CAR had a structure as exemplarily shown in FIG. 1 (however, with an Fc epsilon signaling sequence) and had a nucleic acid sequence of SEQ ID NO:30. Of course, it should be noted that other suitable sequences for the production of HER2.CAR may have a sequence identity of at least 90%, or at least 95%, or at least 96%, or at least 97%, or at least 98%, or at least 99% to SEQ ID NO:30. The primary transcript of the tricistronic nucleic acid then lead to the formation of HER2.CAR, $CD16^{158}$, and erIL-2 as the recombinant polypeptides. FIG. 3 exemplarily and schematically depicts a linearized recombinant nucleic acid used for transfection of the NK-92 cells.

All transfections generally followed standard protocol: NK-92 cells were grown in X-Vivo10 medium (Lonza, Basel, Switzerland) supplemented with 5% Human AB Serum (Valley Biomedical, Winchester, Va.) and 500 IU/mL IL-2 (Prospec, Rehovot, Israel). Cells were electroporated with tricistronic or quadracistronic DNA using the Neon™ electroporation device (Life Technologies, Carlsbad, Calif.), following the manufacturer's parameters for NK-92 cells (1250 V, 10 ms, 3 pulses) and using 5 μg of DNA per $10^6$ cells in a volume of 100 μl. Electroporated cells were transferred into medium (same as above) without exogenously added IL-2.

Selection for recombinant cells and clones was based on continued cell culture in the absence of exogenously added IL-2 as all recombinant cells included a recombinant autocrine growth promoting cytokine (e.g., IL-2, erIL-2, IL-15, or erIL-15).

Figure 4:
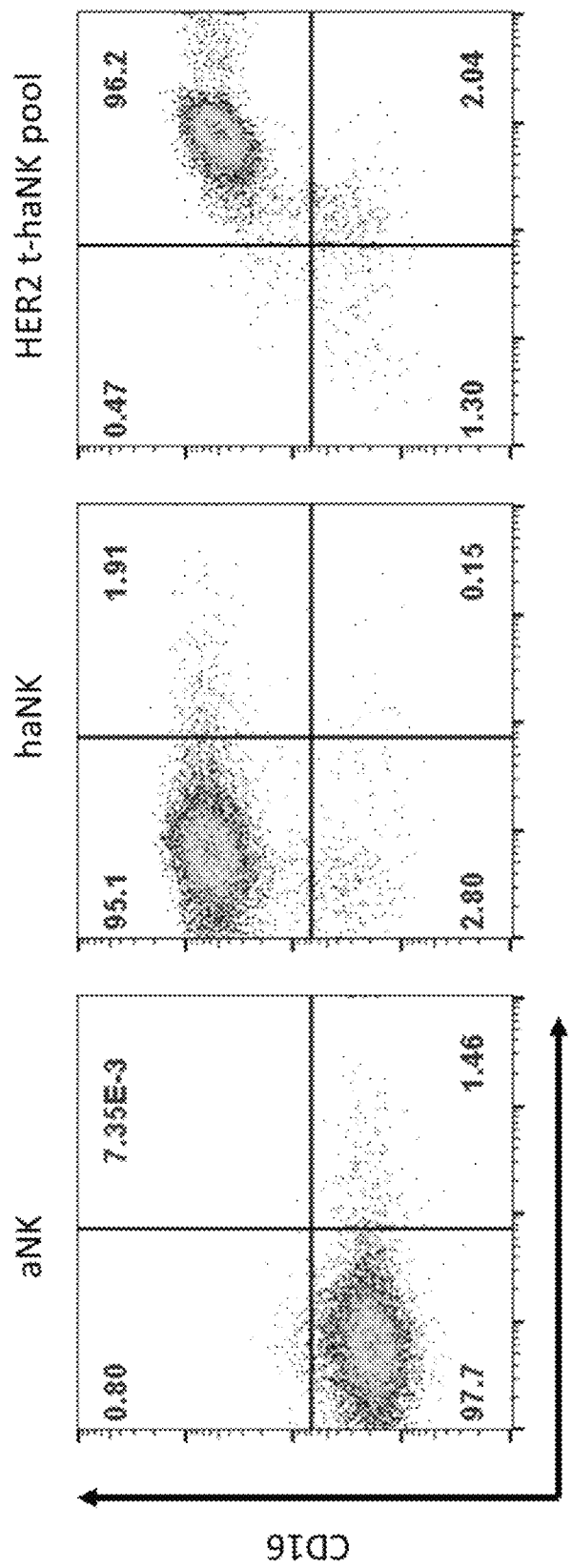
FIG. 4 depicts exemplary FACS results for NK cells transfected with the tricistronic recombinant nucleic acid demonstrating expression of CD16 and HER2.CAR from a polyclonal collection of cells.

The HER2.CAR and CD16 expression on the NK-92 cell surface was determined by flow cytometry using biotinylated soluble HER2 protein and APC-labeled streptavidin, and fluorescently labeled anti-CD16 antibody. Exemplary results for HER2.CAR and CD16 expression (polyclonal) are shown in FIG. 4 along with aNK (not expressing CD16) and haNK (expressing CD16) controls. As can be readily seen from FIG. 4, the polyclonal cell cultures had a significant and strong expression for both, HER2.CAR and $CD16^{158V}$. In this context, it should be noted that the HER2.CAR was expressed at notably higher levels where the HER2.CAR had a FcεRIγ signaling portion as compared to other signaling portions (data not shown).

Figure 5:
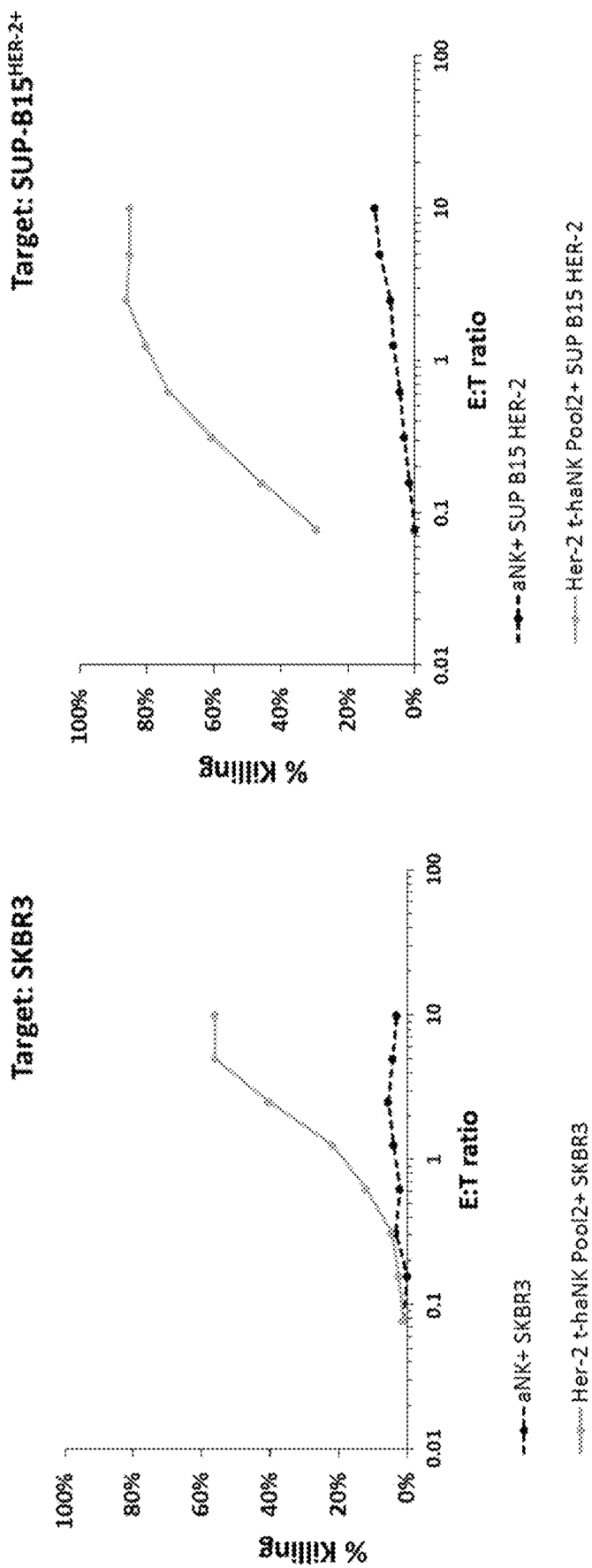
FIG. 5 depicts exemplary results for CAR-mediated cytotoxicity of NK cells transfected with the tricistronic recombinant nucleic acid of FIG. 3.

HER2.CAR t-haNK cells had strong and target specific CAR-mediated cytotoxicity as can be seen from the results depicted in FIG. 5. Here, SKBR3 cells and SUP-B15$^{HER-2+}$ cells were co-incubated with HER2.CAR t-haNK cells at varying effector to target cell ratios (e.g., between 0.075 and 10) in a flow-cytometry based in vitro cytotoxicity assay, and target specificity was compared to aNK cells as indicated. As can be seen, CAR-mediated cytotoxicity using a polyclonal HER2.CAR t-haNK cell population was >60% for SKBR3cells and approaching 90% for SUP-B15$^{HER-2+}$ cells.

Figure 6:
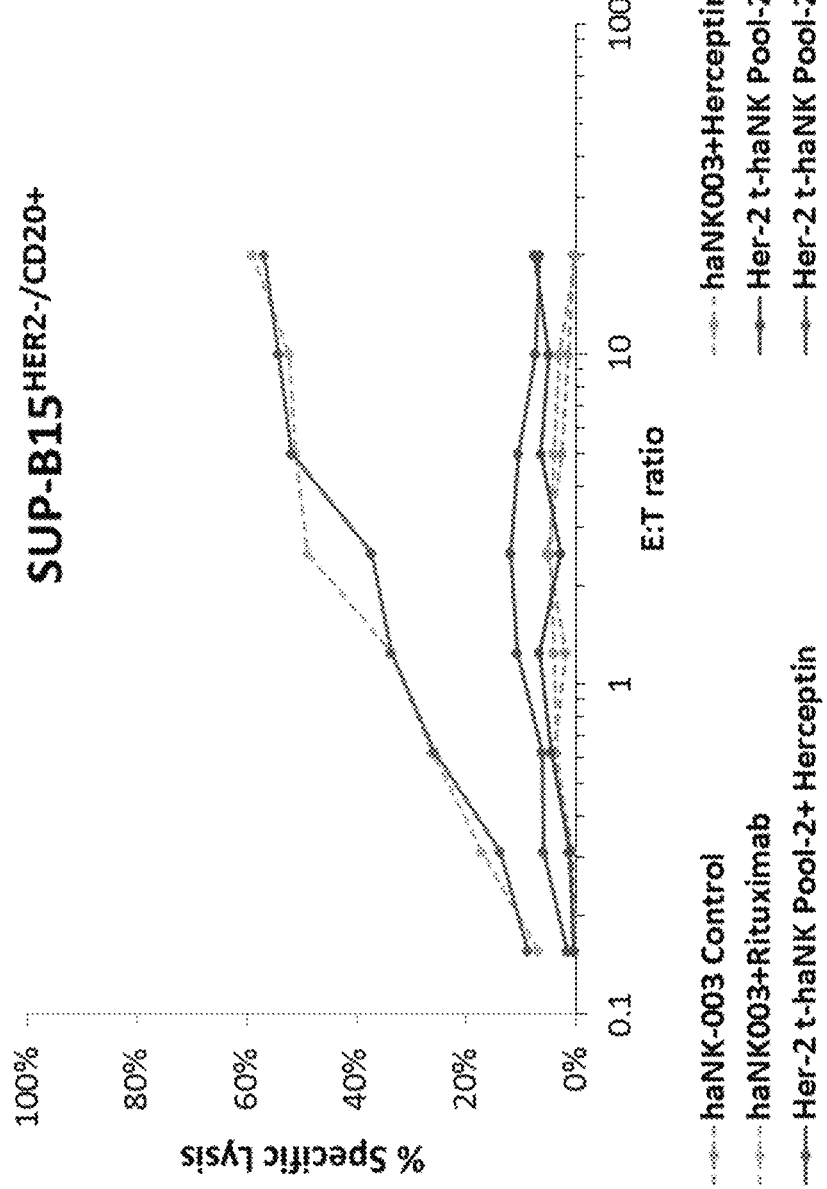
FIG. 6 depicts exemplary results for ADCC of NK cells transfected with the tricistronic recombinant nucleic acid of FIG. 3.

In a similar manner, ADCC was tested using SUP-B15$^{HER-2-/CD20+}$ cells and rituximab as target specific antibody and Herceptin as control antibody. Once again, the polyclonal HER2.CAR t-haNK cells had strong and target specific ADCC approaching 60% as can be seen from the exemplary results depicted in FIG. 6, with no substantial off-target toxicity.

Figure 7:
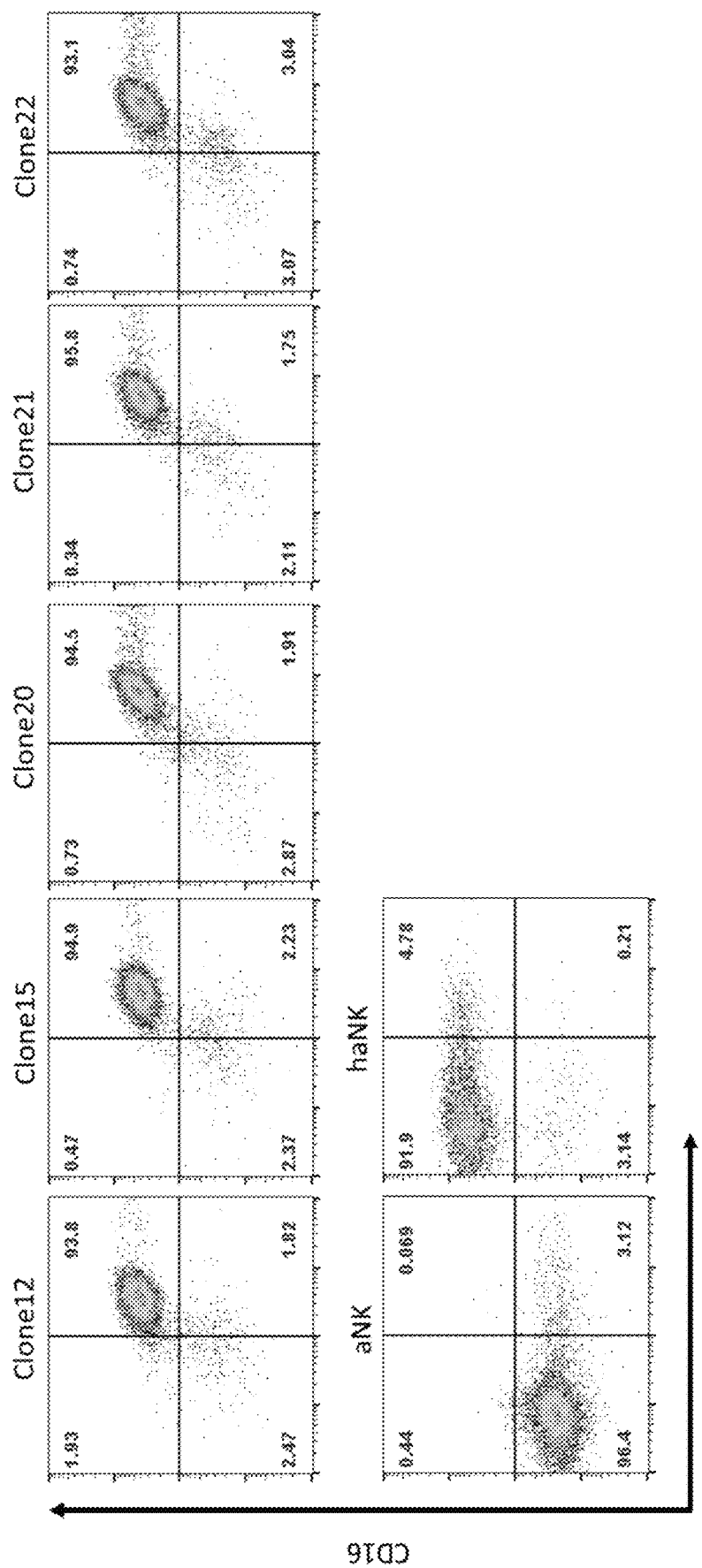
FIG. 7 depicts exemplary FACS results for NK cells transfected with the tricistronic recombinant nucleic acid demonstrating expression of CD16 and HER2.CAR from selected clonal cell lines.

A number of individual clones from the HER2.CAR t-haNK cell population were then prepared following dilution propagation, and expression analysis was once more performed via FACS using the same procedure as described above. aNK and haNK cells were used as controls. Once more, it was observed that all individual clones had a significant and strong expression of both HER2.CAR and $CD16^{158V}$ as can be seen from the exemplary results of FIG. 7.

Figure 8:
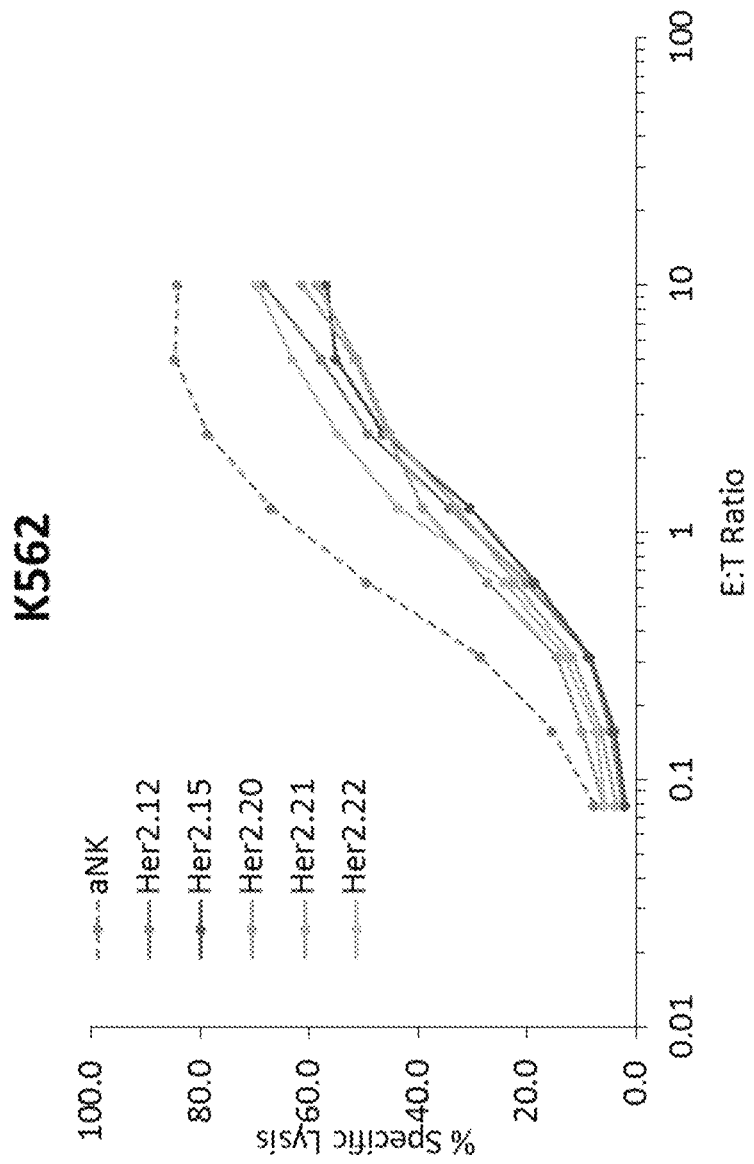
FIG. 8 depicts exemplary results for natural cytotoxicity of NK cells from selected clonal cell lines transfected with the tricistronic recombinant nucleic acid of FIG. 3.
Figure 9:
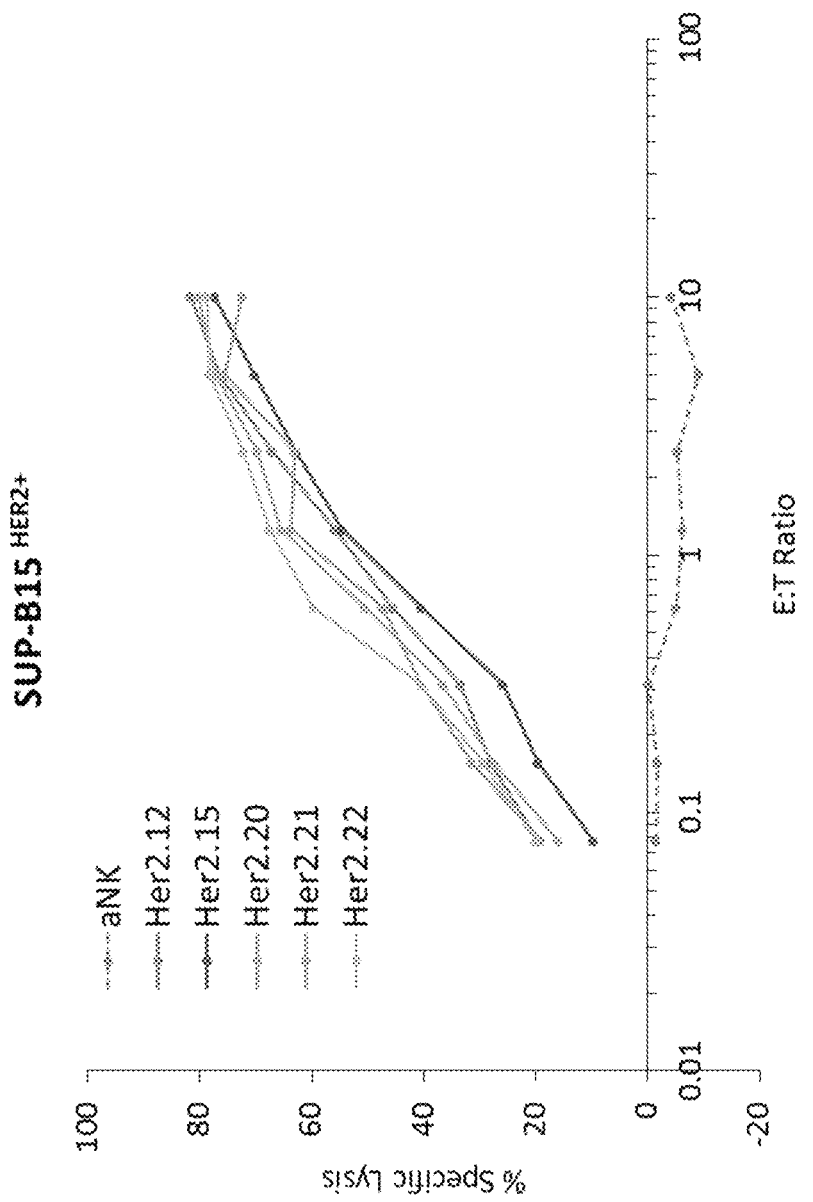
FIG. 9 depicts exemplary results for CAR-mediated cytotoxicity of NK cells from selected clonal cell lines transfected with the tricistronic recombinant nucleic acid of FIG. 3.
Figure 10:
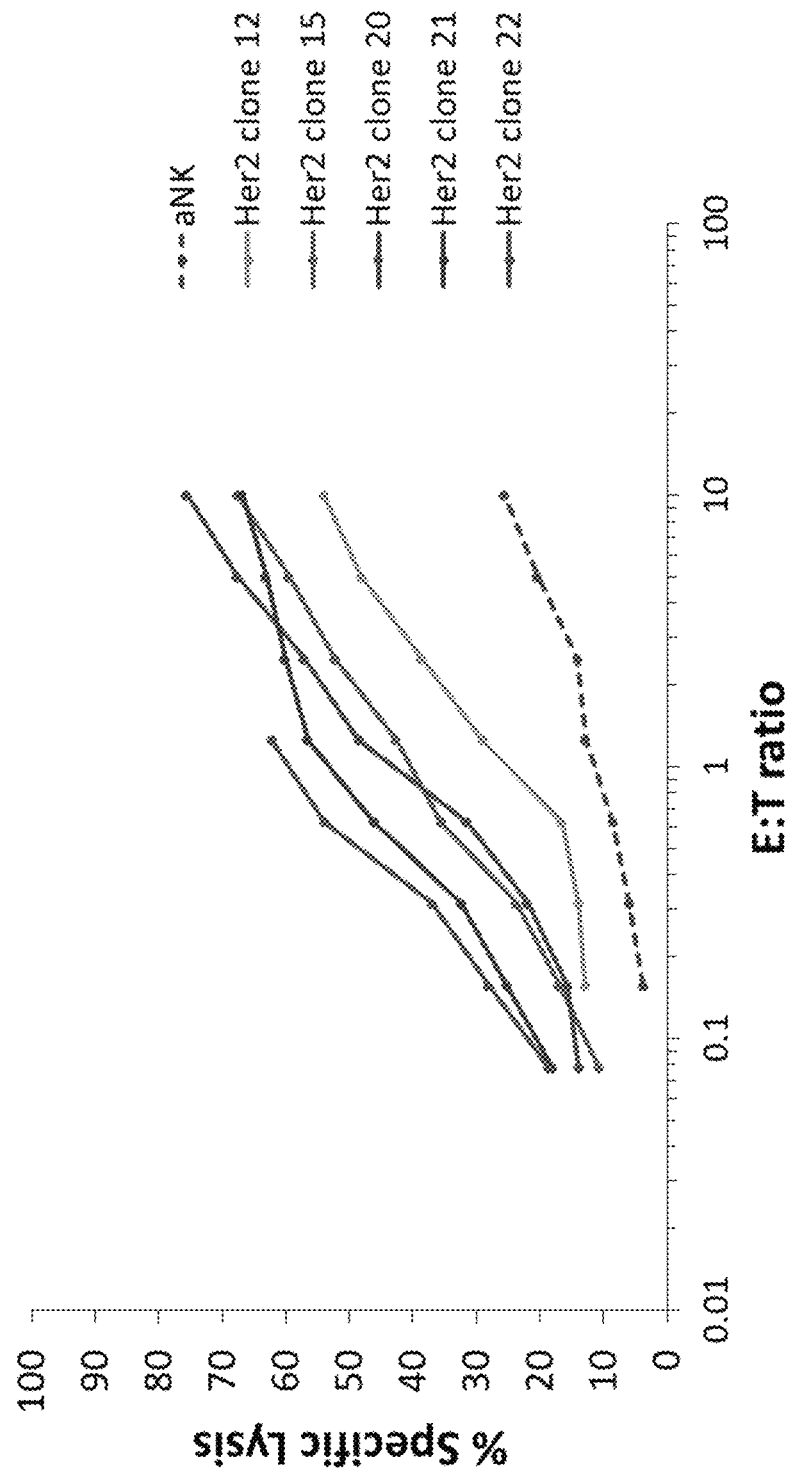
FIG. 10 depicts further exemplary results for CAR-mediated cytotoxicity of NK cells from selected clonal cell lines transfected with the tricistronic recombinant nucleic acid of FIG. 3.
Figure 11:
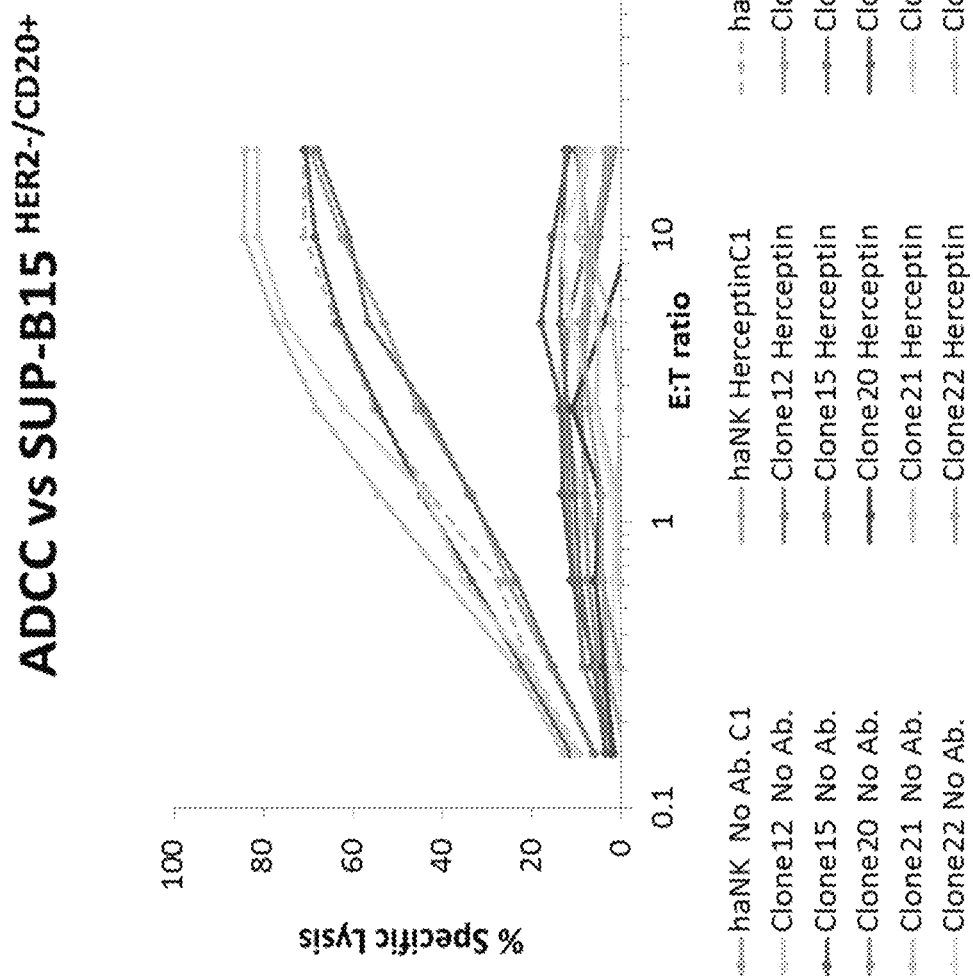
FIG. 11 depicts further exemplary results for ADCC of NK cells from selected clonal cell lines transfected with the tricistronic recombinant nucleic acid of FIG. 3.

Individual HER2.CAR t-haNK cell clones were tested for natural cytotoxicity using K562 cells and results were compared to non-transfected aNK cells as is shown in FIG. 8. Here, specific lysis at effector to target cell ratios as indicated was lower than control aNK lysis, however, only about 10-20% less. On the other hand, CAR-mediated cytotoxicity was once more substantial and target restricted using SUP-B15$^{HER-2+}$ cells and exemplary results for specific HER2.CAR t-haNK cell clones are shown in FIG. 9 over a wide range of effector to target ratios. Likewise, where SKBR3 cells were used as target cells, notable CAR-mediated cytotoxicity was again observed for all of the tested HER2.CAR t-haNK cell clones as is exemplarily shown in FIG. 10. Selected HER2.CAR t-haNK cell clones were also tested for ADCC against SUP-B15$^{HER-2-/CD20+}$ cells using rituximab as target specific antibody and Herceptin as control antibody. As can be taken from FIG. 11, all HER2.CAR t-haNK cell clones had once more significant, strong, and target specific ADCC against control.

Figure 12:
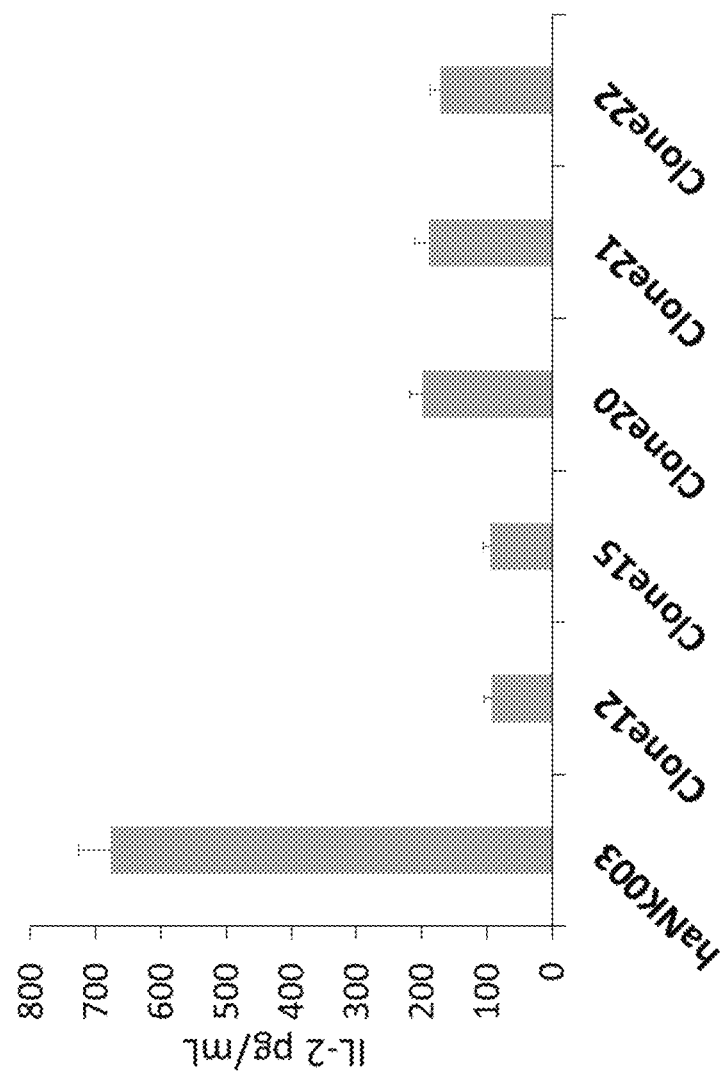
FIG. 12 depicts exemplary results for erIL-2 release from NK cells from selected clonal cell lines transfected with the tricistronic recombinant nucleic acid of FIG. 3.

While all HER2.CAR t-haNK polyclonal cultures and cell clones propagated well in the absence of exogenous IL-2, expression of er-IL2 was also tested along with the quantity of erIL-2 released in the culture medium. Exemplary results are shown in FIG. 12 depicting a minor release of erIL-2 into the culture medium. Notably, the extracellular erIL-2 release was significantly less than that of a closely related haNK003 cell line as is shown in FIG. 12. Such reduced release may further advantageously reduce potential systemic effects otherwise attributable to IL-2 (e.g., vascular permeability, systemic vascular leak, etc.).

Figure 13:
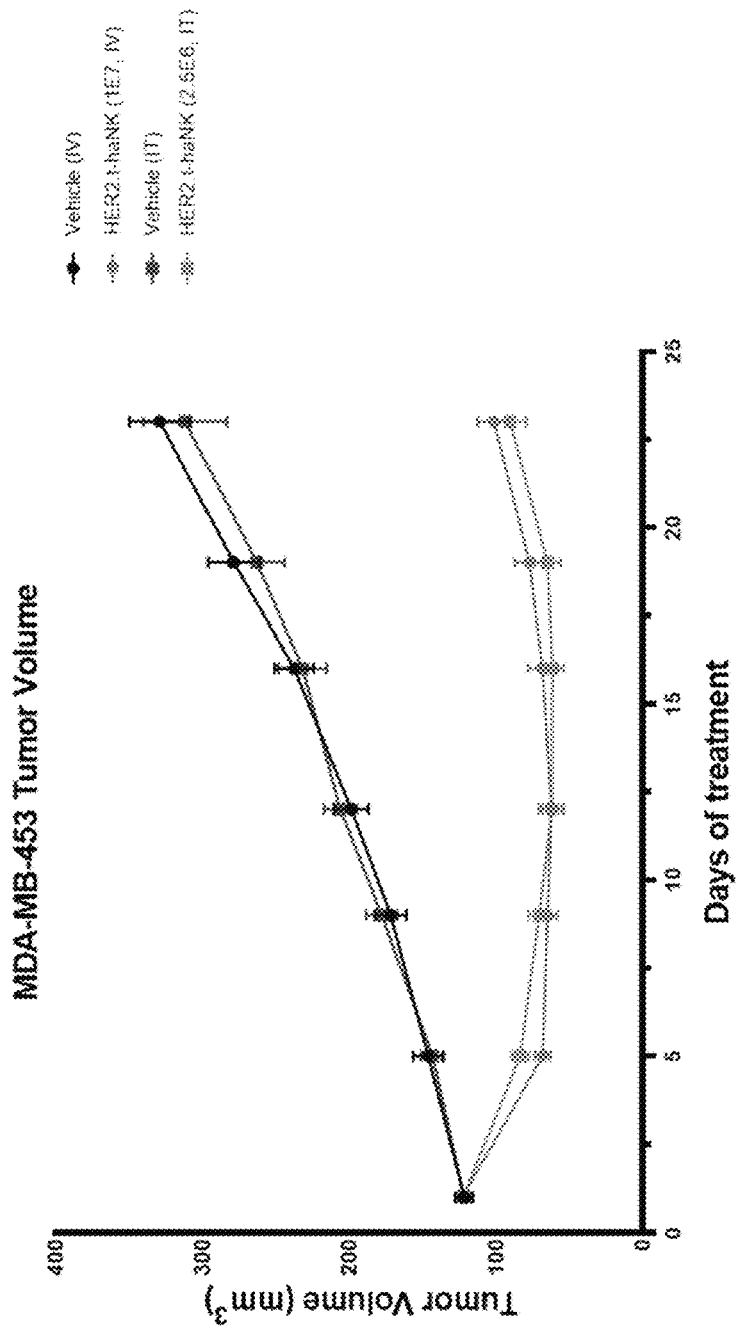
FIG. 13 depicts exemplary in vivo results for MDA-MB-453 tumor volume changes using NK cells transfected with the tricistronic recombinant nucleic acid of FIG. 3.

To test in vivo efficacy of the HER2.CAR t-haNK cells, NSG mice (NOD.Cg-Prkdc$^{scid}$ Il2rg$^{tm1Wjl}$/SzJ) were implanted with MDA-MB-453 tumor cells subcutaneously, and tumor volume was measured. When tumors reached an average ~120 mm$^3$, HER2.CAR t-haNK cells were administered intratumorally or intravenously twice a week for the duration of the study. Following administration of HER2.CAR t-haNK cells, tumor volume was sustainably reduced compared to vehicle control treatment as is demonstrated by the exemplary results in FIG. 13. It should be appreciated that intratumoral administration required significantly less HER2.CAR t-haNK cells for the same reduction in tumor volume than systemic intravenous administration.

Figure 14:
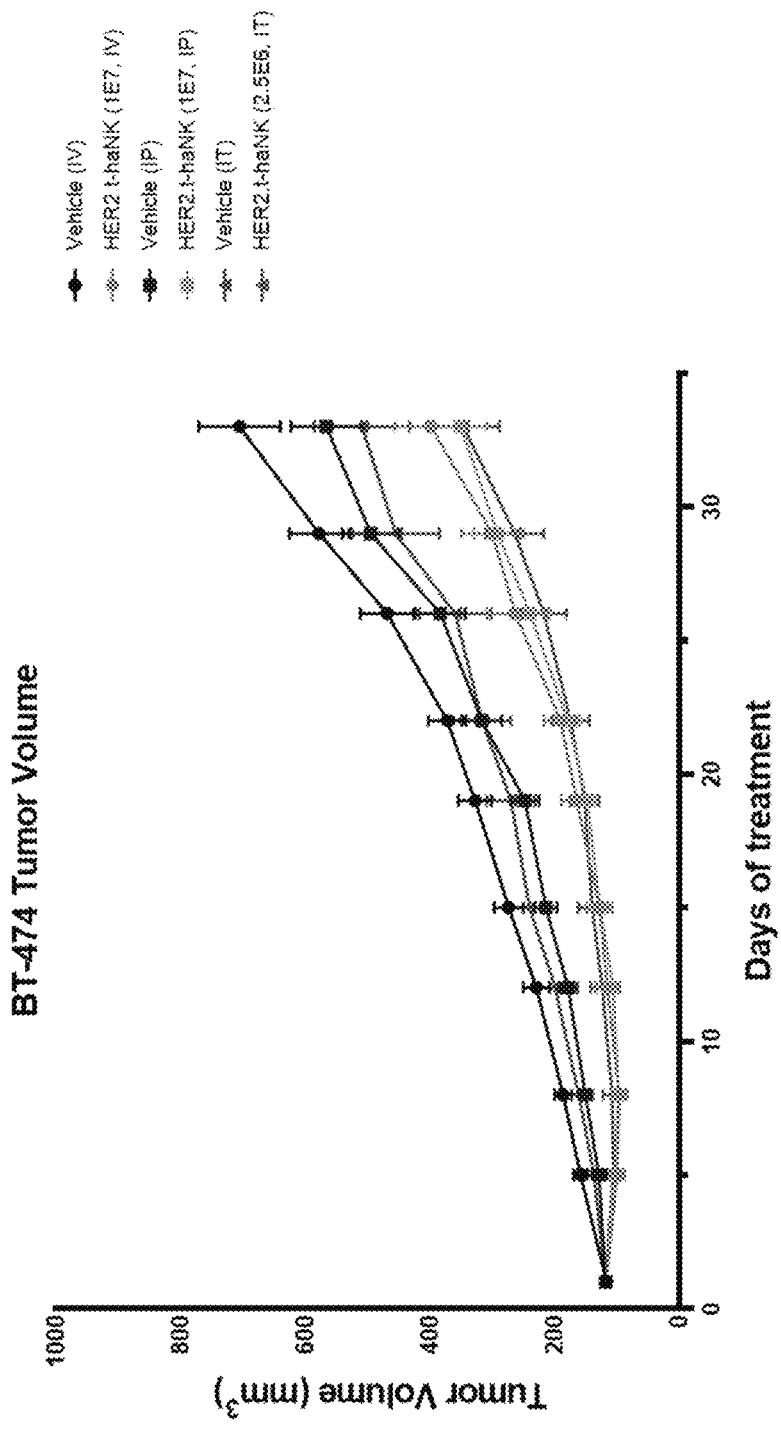
FIG. 14 depicts exemplary in vivo results for BT-474 tumor volume changes using NK cells transfected with the tricistronic recombinant nucleic acid of FIG. 3.

Similarly, in vivo efficacy of the HER2.CAR t-haNK cells was tested in NSG mice that were implanted with BT-474 tumor cells subcutaneously, and the tumor volume was measured over time. When tumors reached an average ~120 mm$^3$, HER2.CAR t-haNK cells were administered intratumorally or intravenously twice a week for the duration of the study. Following administration of HER2.CAR t-haNK cells, the increase in tumor volume was substantially reduced over the time period tested as is shown by the exemplary results in FIG. 14. Once more, it should be appreciated that intratumoral administration required significantly less HER2.CAR t-haNK cells for the same reduction in tumor growth than systemic intravenous administration.

Example 2: EGFR.CAR t-haNK Cells

Figure 15:
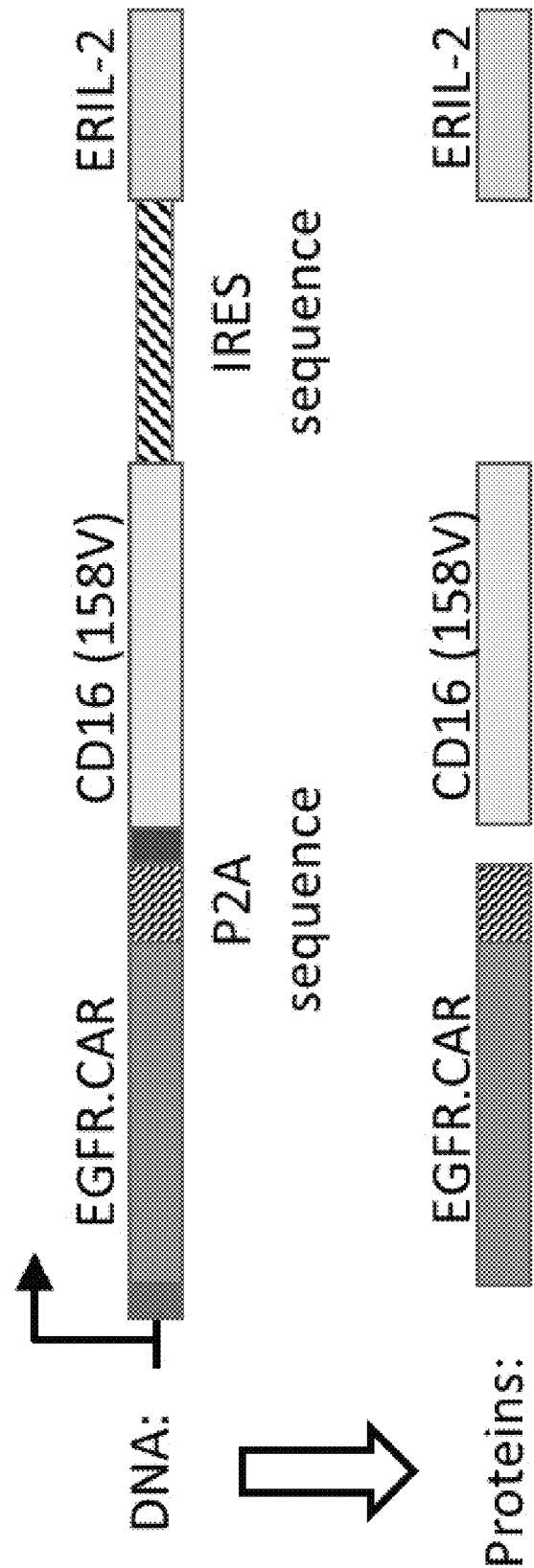
FIG. 15 is a schematic representation of an exemplary tricistronic recombinant nucleic acid encoding a EGFR2.CAR, followed by a P2A sequence, followed by a sequence encoding a high-affinity variant of CD16. The CD16 sequence is followed by an IRES sequence, which is followed in turn by a sequence encoding erIL-2.
Figure 16:
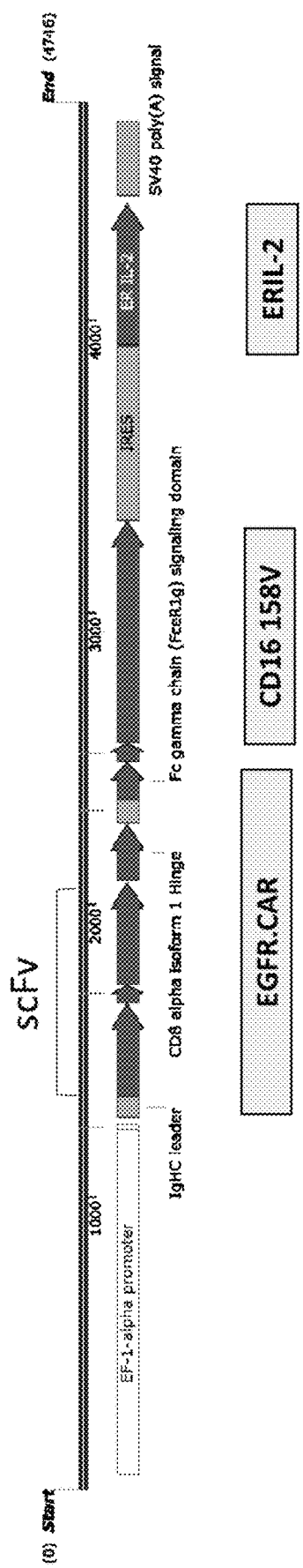
FIG. 16 is another schematic representation of an exemplary tricistronic recombinant nucleic acid encoding a EGFR2.CAR, a high-affinity variant of CD16, and erIL-2 used to generate recombinant NK cells.

To generate EGFR.CAR t-haNK cells, a recombinant DNA molecule was assembled as is schematically depicted in FIG. 15 where the tricistronic configuration included a sequence encoding a EGFR.CAR followed by a P2A sequence, which was followed by a sequence encoding CD16 (or $CD16^{158V}$), and which in turn was followed by an IRES sequence element upstream of a sequence encoding erIL-2. Unless otherwise noted, the EGFR.CAR had a structure as exemplarily shown in FIG. 1 (however, with an Fc epsilon signaling sequence) and had a nucleic acid sequence of SEQ ID NO:33. Of course, it should be noted that other suitable sequences for the production of EGFR-.CAR may have a sequence identity of at least 90%, or at least 95%, or at least 96%, or at least 97%, or at least 98%, or at least 99% to SEQ ID NO:33. The primary transcript of the tricistronic nucleic acid then lead to the formation of EGFR.CAR, $CD16^{158V}$, and erIL-2 as the recombinant polypeptides. FIG. 16 exemplarily and schematically depicts a linearized recombinant nucleic acid used for transfection of the NK-92 cells.

Figure 17:
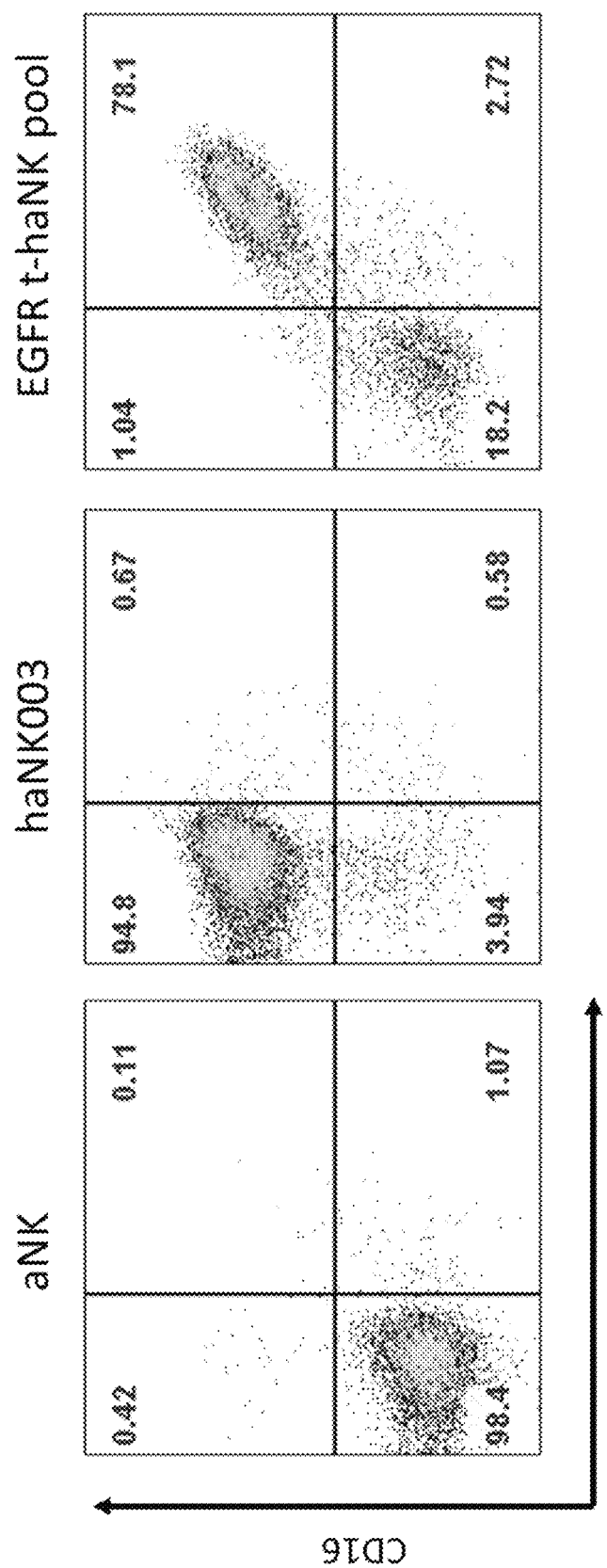
FIG. 17 depicts exemplary FACS results for NK cells transfected with the tricistronic recombinant nucleic acid demonstrating expression of CD16 and EGFR2.CAR from a polyclonal collection of cells.

The EGFR.CAR and CD16 expression on the NK-92 cell surface was determined by flow cytometry using biotinylated anti-scFv antibody and APC-labeled streptavidin, and fluorescently labeled anti-CD16 antibody. Exemplary results for EGFR.CAR and CD16 expression (polyclonal) are shown in FIG. 17 along with aNK (not expressing CD16) and haNK (expressing CD16) controls. As can be readily seen from FIG. 17, the polyclonal cell cultures had a significant and strong expression for both, EGFR.CAR and $CD16^{158V}$. In this context, it should once more be noted that the EGFR.CAR was expressed at notably higher levels where the HER2.CAR had a FcεRIγ signaling portion as compared to other signaling portions (data not shown).

Figure 18:
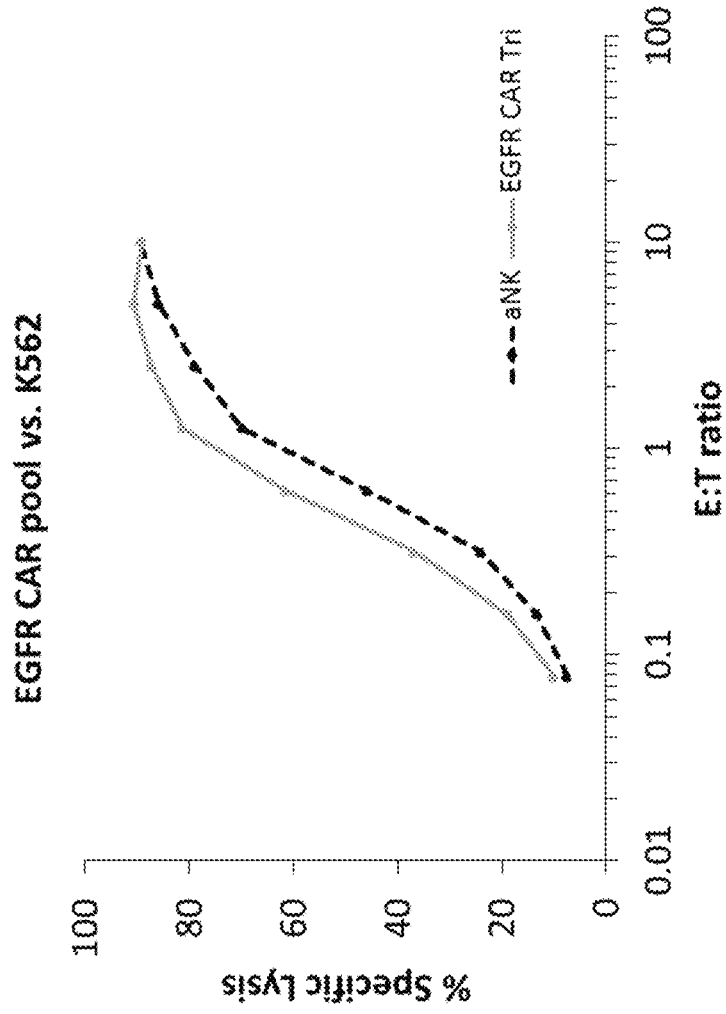
FIG. 18 depicts exemplary results from a polyclonal collection of cells for natural cytotoxicity of NK cells transfected with the tricistronic recombinant nucleic acid of FIG. 16.
Figure 19:
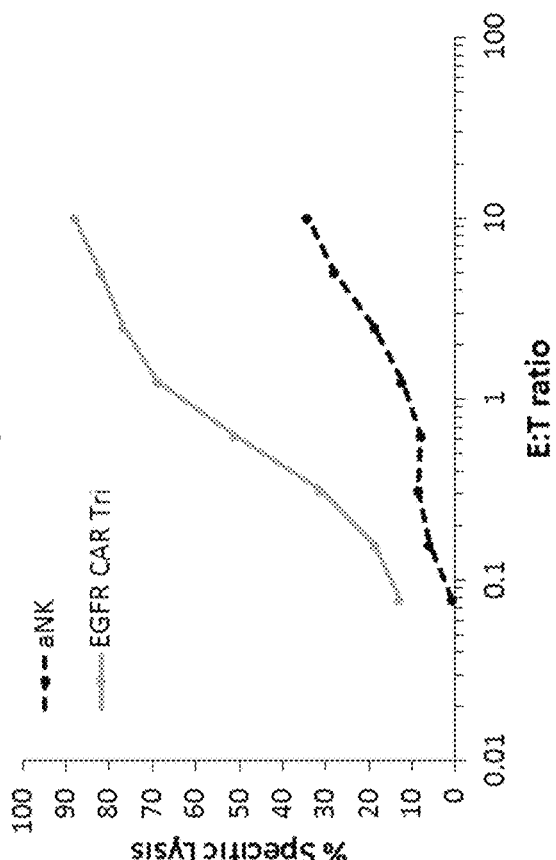
FIG. 19 depicts exemplary results from a polyclonal collection of cells for CAR-mediated cytotoxicity of NK cells transfected with the tricistronic recombinant nucleic acid of FIG. 16.
Figure 19:
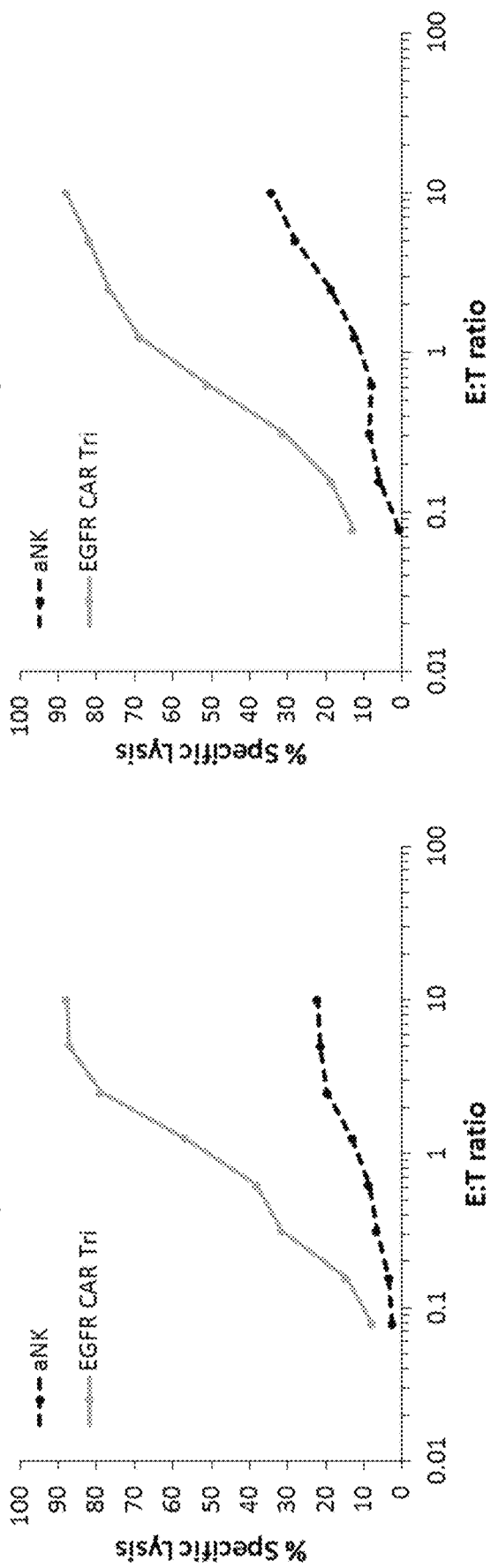
Figure 20:
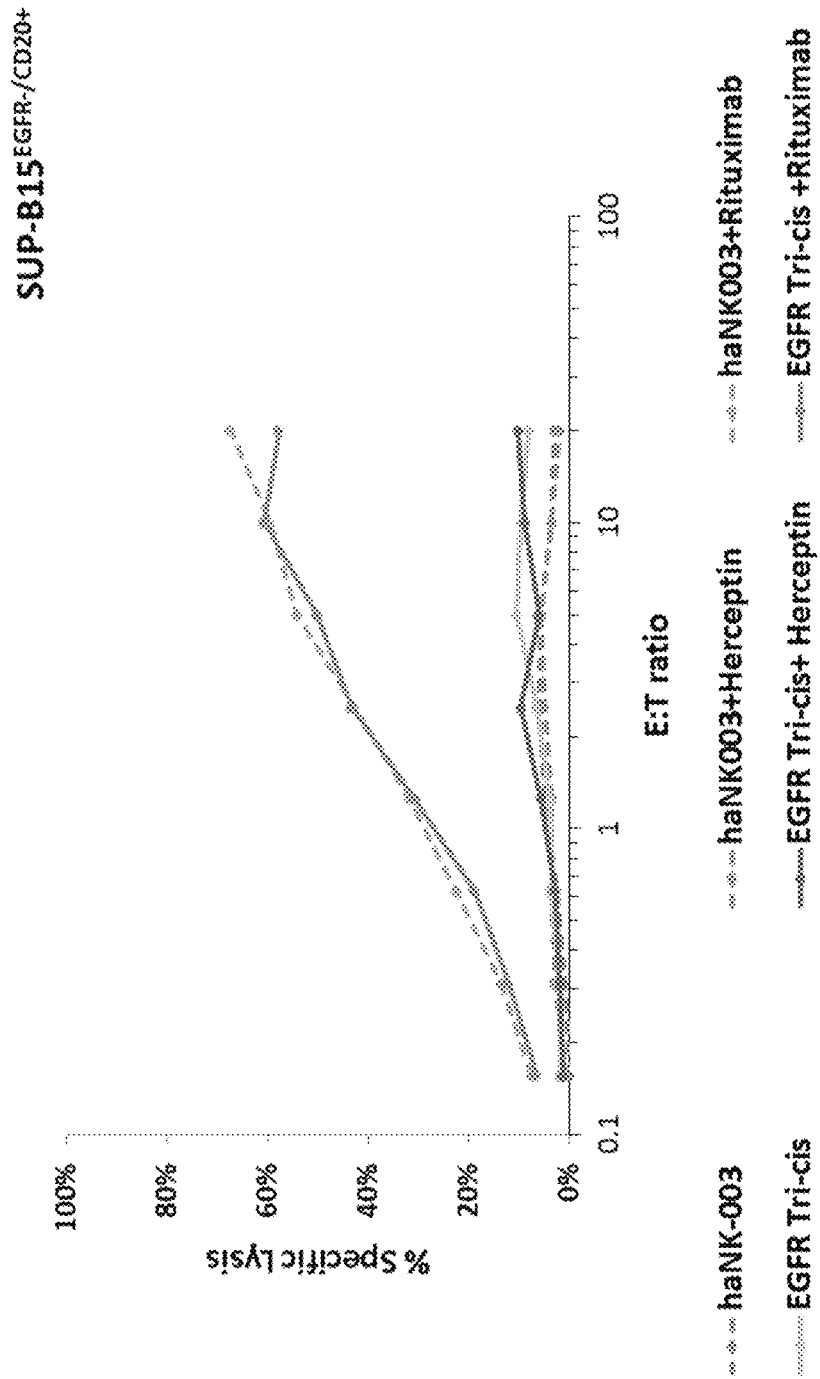
FIG. 20 depicts exemplary results from a polyclonal collection of cells for ADCC of NK cells transfected with the tricistronic recombinant nucleic acid of FIG. 16.

Natural cytotoxicity was determined for polyclonal cell culture of the EGFR.CAR t-haNK cells, and FIG. 18 depicts an exemplary set of results. Here, the natural cytotoxicity against K562 cells indeed exceeded the cytotoxicity of aNK control cells. Similarly, CAR-mediated cytotoxicity was determined for polyclonal cell culture of the EGFR.CAR t-haNK cells against HCT116 target cells and against A549 cells, both of which expressed EGFR. As can be seen from the graphs in FIG. 19, CAR-mediated cytotoxicity was significant and specific. In still further experiments, the inventors tested EGFR.CAR t-haNK polyclonal cells for ADCC against $SUP-B15^{EGFR-/CD20+}$ cells using rituximab as target specific antibody and Herceptin as control antibody. As can be taken from FIG. 20, all EGFR.CAR t-haNK cells had once more significant, strong, and target specific ADCC versus control.

Figure 21:
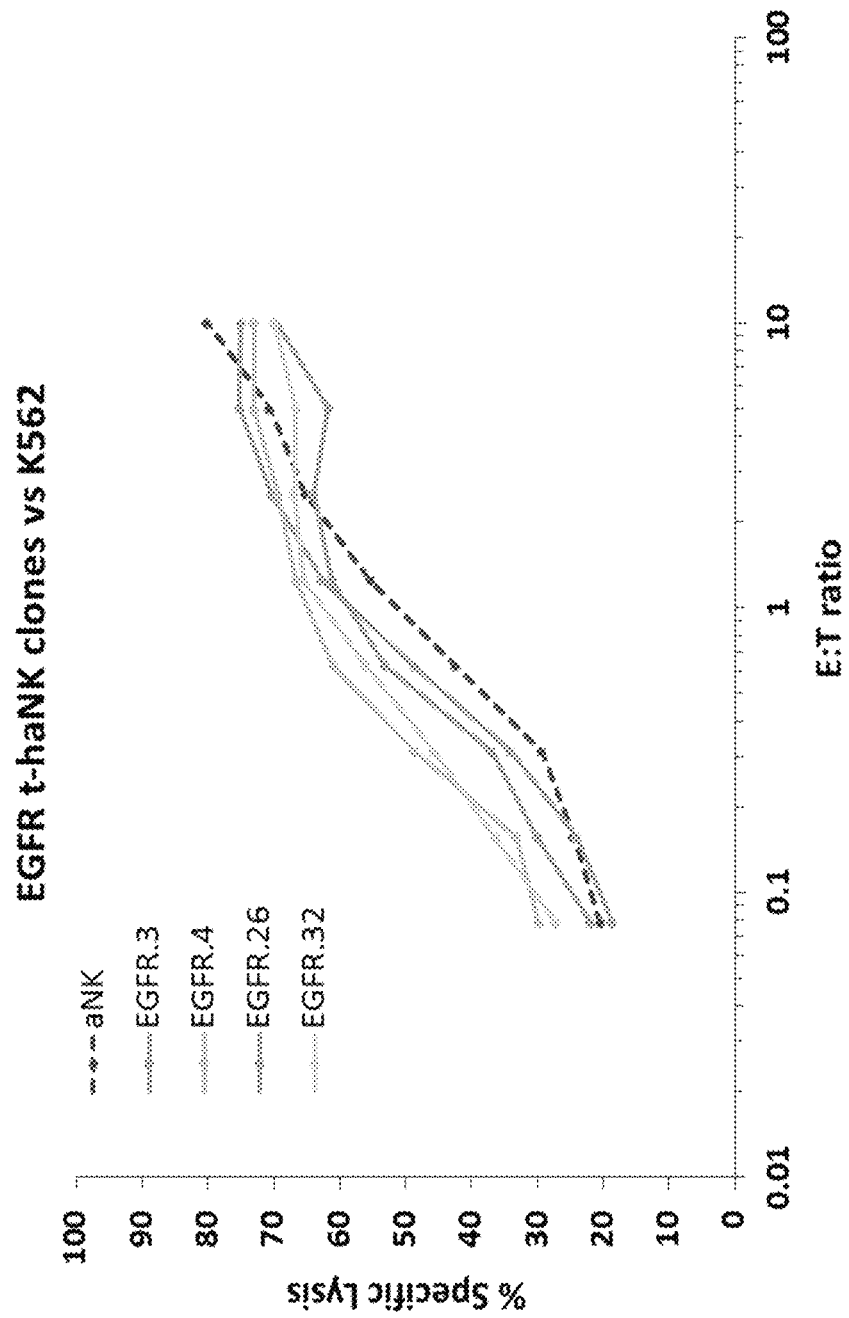
FIG. 21 depicts exemplary results from selected cell lines for natural cytotoxicity of NK cells transfected with the tricistronic recombinant nucleic acid of FIG. 16.
Figure 22:
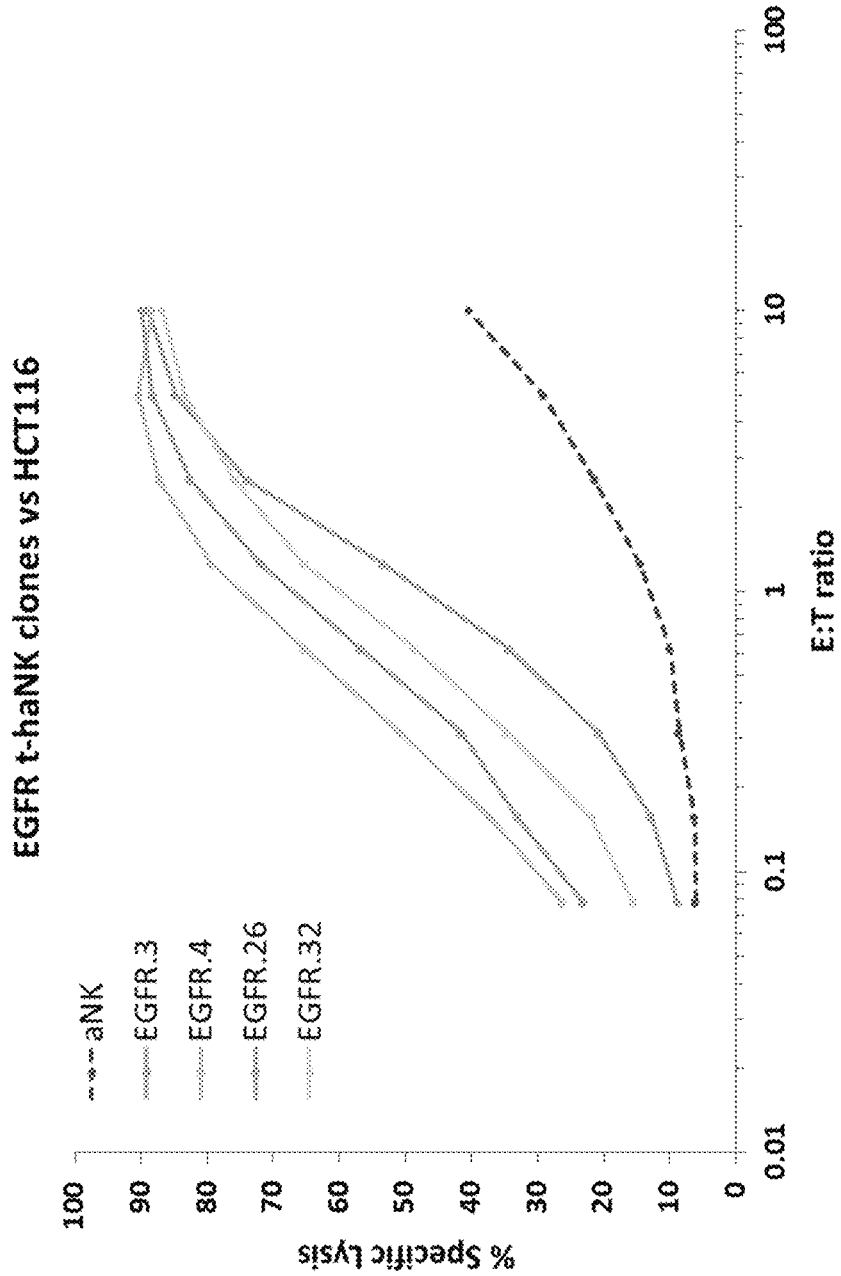
FIG. 22 depicts exemplary results from selected cell lines for CAR-mediated cytotoxicity of NK cells transfected with the tricistronic recombinant nucleic acid of FIG. 16.
Figure 23:
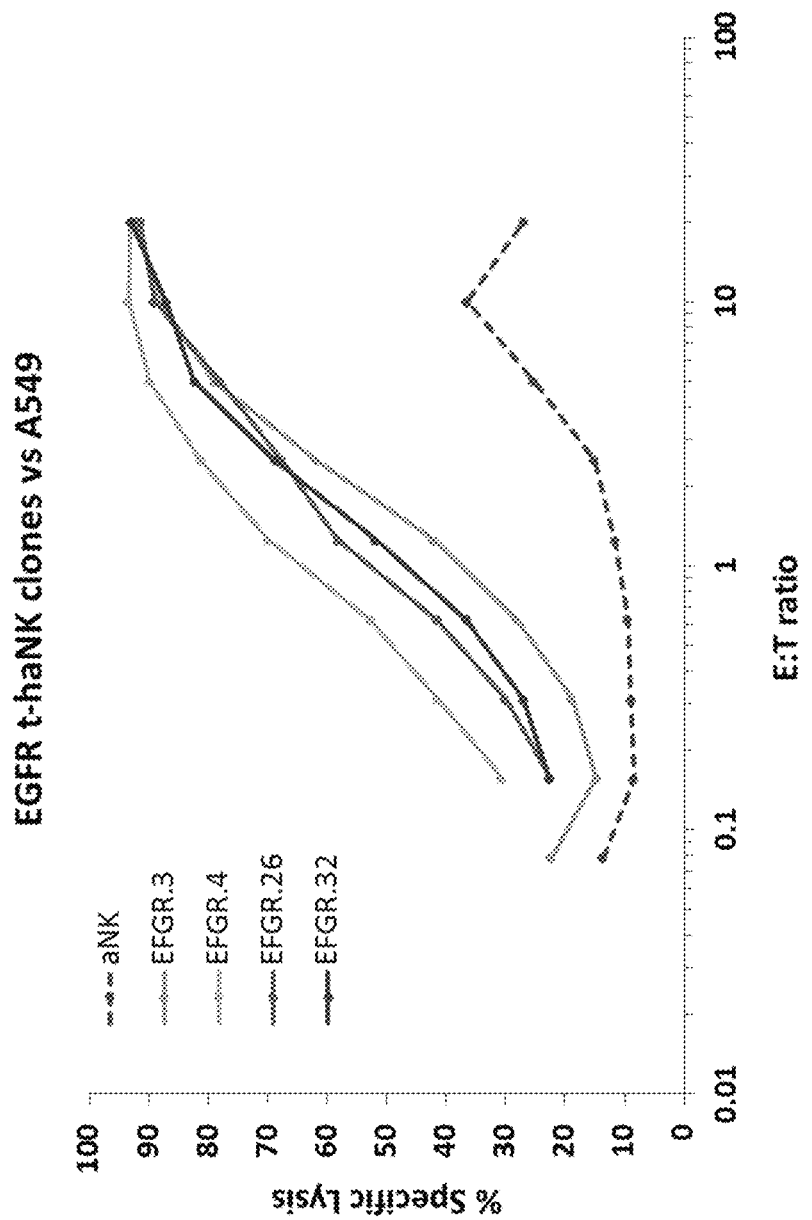
FIG. 23 depicts further exemplary results from selected cell lines for CAR-mediated cytotoxicity of NK cells transfected with the tricistronic recombinant nucleic acid of FIG. 16

After dilution propagation, selected EGFR.CAR t-haNK cell clones were tested for natural cytotoxicity against 562 cells. Notably, all selected EGFR.CAR t-haNK cell clones had substantially identical natural cytotoxicity which was comparable to the aNK control as can be taken from FIG. 21. Selected EGFR.CAR t-haNK cell clones were then tested for CAR-mediated cytotoxicity against HCT116 tumor cells, and exemplary results are shown in the graphs of FIG. 22. Once more all EGFR.CAR t-haNK cell clones had very significant CAR-mediated cytotoxicity against HCT116 tumor cells approaching 90% specific lysis. Similar results were obtained using A549 tumor cells as target cells as is shown in FIG. 23.

Figure 24:
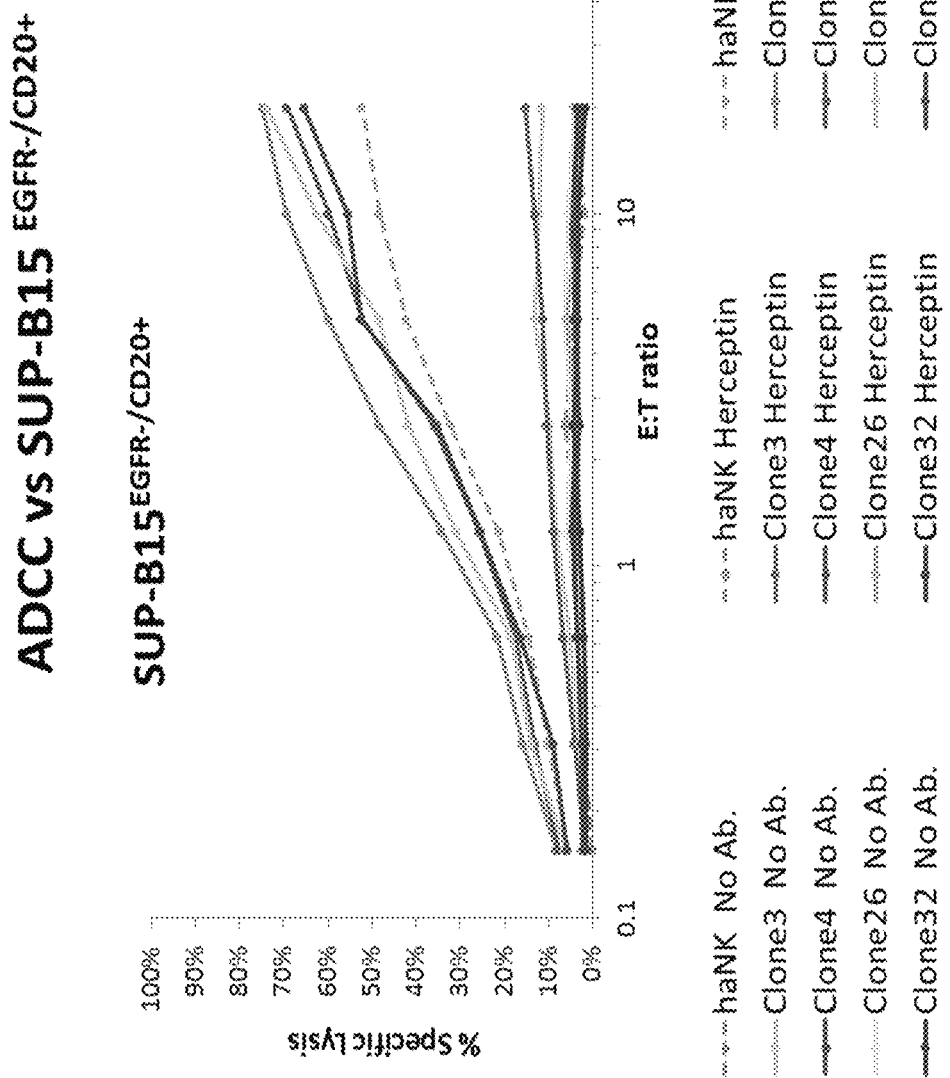
FIG. 24 depicts further exemplary results for ADCC of NK cells from selected clonal cell lines transfected with the tricistronic recombinant nucleic acid of FIG. 16.

In still further experiments, the inventors determined ADCC for selected EGFR.CAR t-haNK cell clones using $SUP-B15^{EGFR-/CD20+}$ cells as target cells, rituximab as target specific antibody, and Herceptin as control antibody. As already observed with the polyclonal cell culture and as can be seen from FIG. 24, selected EGFR.CAR t-haNK cell clones exhibited effective ADCC in the presence of cognate antibodies.

Figure 25:
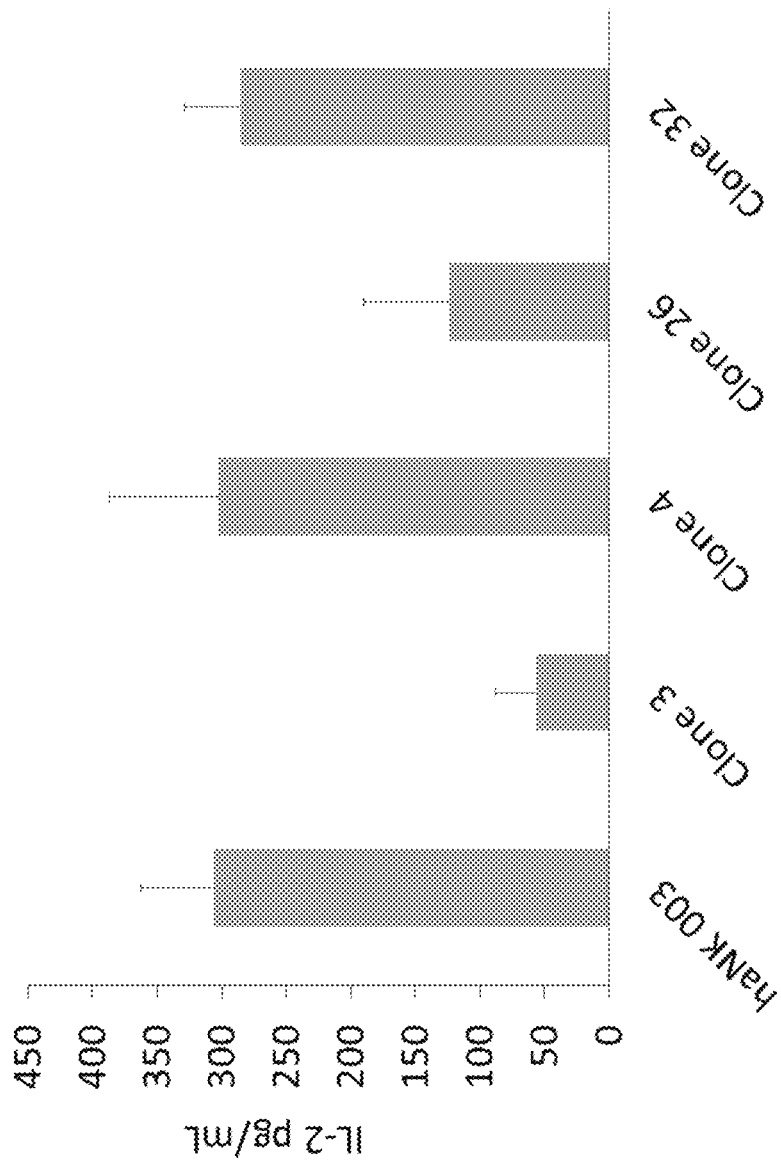
FIG. 25 depicts exemplary results for erIL-2 release from NK cells from selected clonal cell lines transfected with the tricistronic recombinant nucleic acid of FIG. 16.

While all EGFR.CAR t-haNK polyclonal cultures and cell clones propagated well in the absence of exogenous IL-2, expression of er-IL2 was also tested along with the quantity of erIL-2 released in the culture medium. Exemplary results are shown in FIG. 25 depicting for some clones a minor release of erIL-2 into the culture medium while other clones had an erIL-2 release comparable to control. As noted above, reduced erIL-2 release may further advantageously reduce potential systemic effects otherwise attributable to IL-2 (e.g., vascular permeability, systemic vascular leak, etc.).

Example 3: Quadracistronic Constructs

Figure 26:
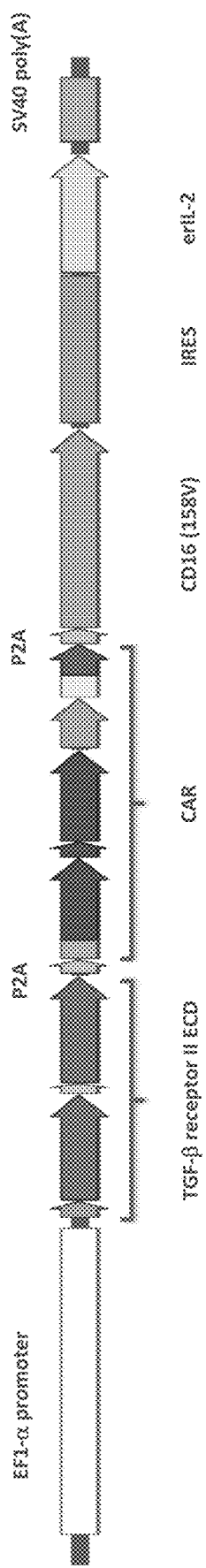
FIG. 26 is a schematic representation of an exemplary quadracistronic recombinant nucleic acid encoding a TGF-beta trap, a CAR, a high-affinity variant of CD16, and erIL-2 used to generate recombinant NK cells.
Figure 27:
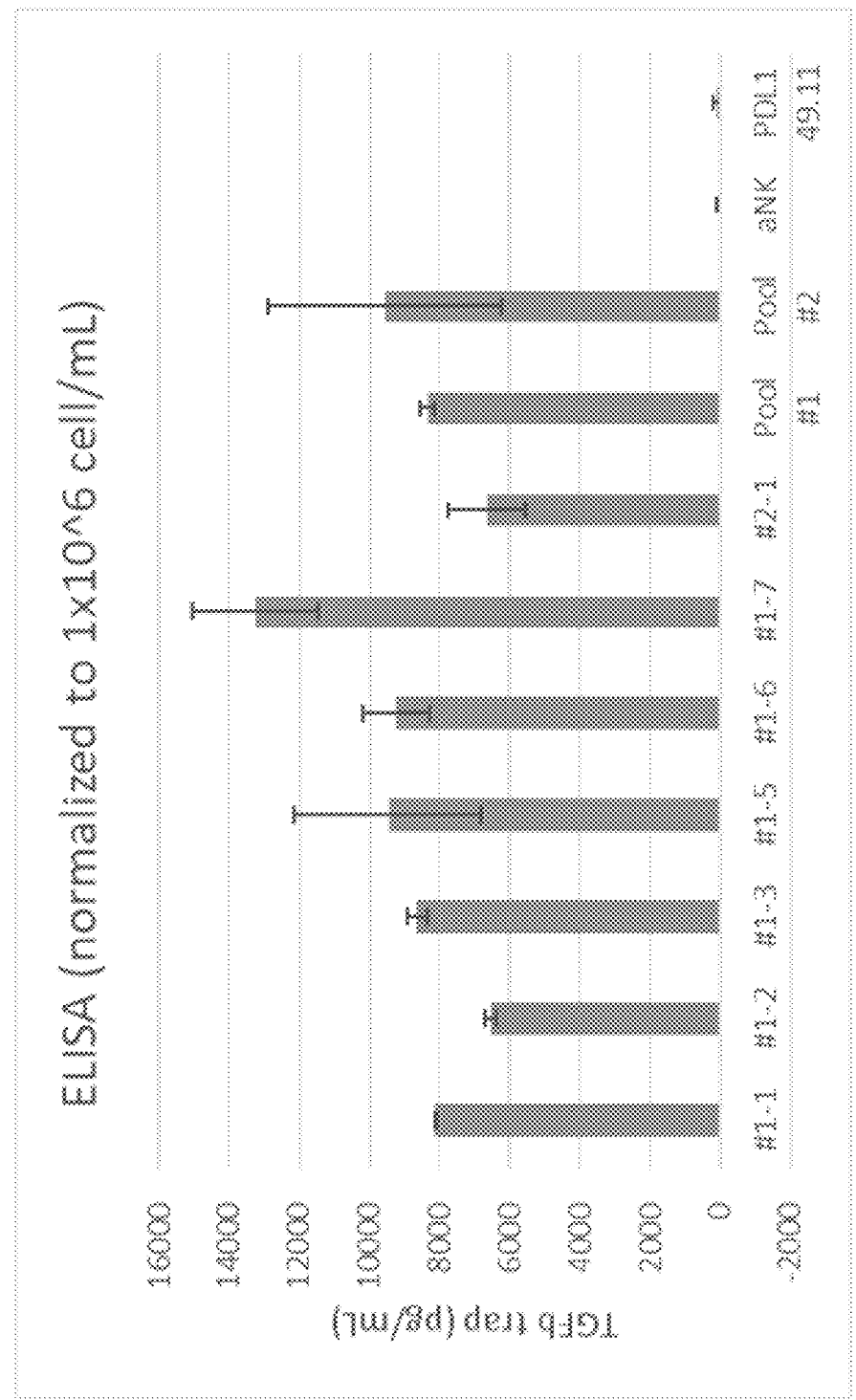
FIG. 27 depicts exemplary results for expression of the TGF-beta trap in NK cells transfected with the quadracistronic recombinant nucleic acid of FIG. 26.

While the above examples were performed with tricistronic constructs it should be appreciated that the same constructs can also be implemented in a quadracistronic construct to express IL-12, a TGF-beta trap, or a homing receptor to so reduce immune suppression in the tumor microenvironment and enrich the tumor microenvironment with thusly modified NK cells. One exemplary quadracistronic construct is schematically illustrated in FIG. 26 where a nucleic acid sequence encoding a TGF-beta trap is upstream of the tricistronic construct as discussed above. As can be seen from FIG. 26, a P2A sequence is located between the TGF-beta trap and the CAR to ensure coordinated expression while producing distinct proteins. Expression of the TGF-beta trap was then tested in an ELISA to ascertain that the quadracistronic construct indeed produced a functional TGF-beta trap, and FIG. 27 depicts exemplary results versus control. Notably, expression levels of the TGF-beta trap were significant throughout all recombinant clones with quadracistronic construct.

Figure 28:
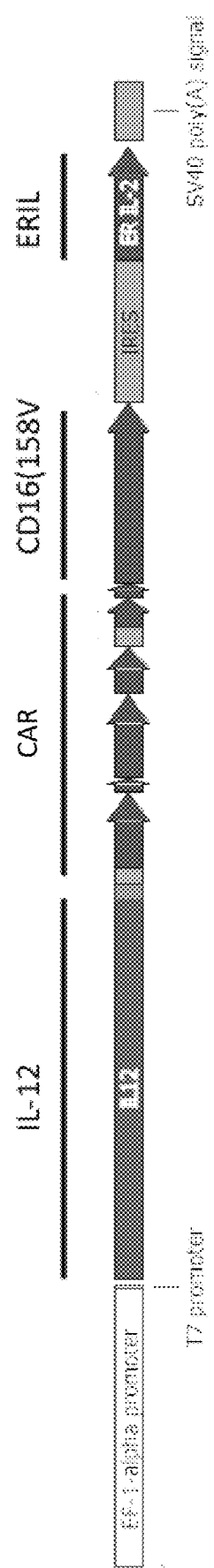
FIG. 28 is a schematic representation of an exemplary quadracistronic recombinant nucleic acid encoding an IL-12 heterodimer, a CAR, a high-affinity variant of CD16, and erIL-2 used to generate recombinant NK cells.
Figure 29:
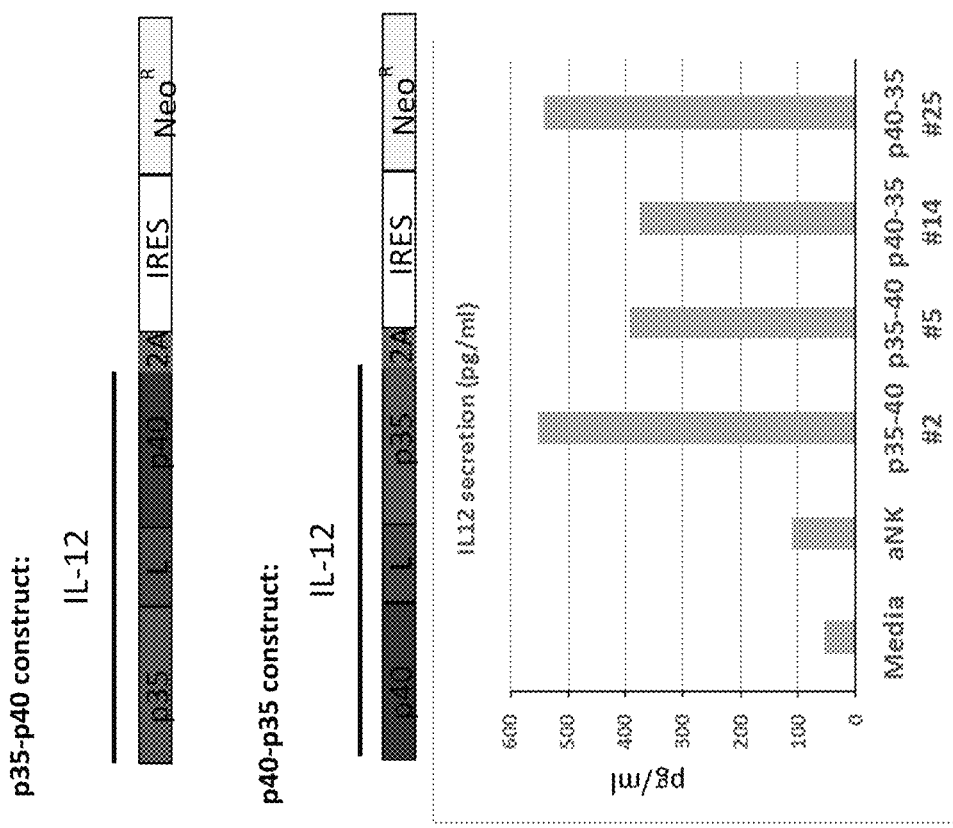
FIG. 29 is a schematic representation of IL-12 heterodimers and respective expression levels of the IL-12 heterodimers in NK cells transfected with the quadracistronic recombinant nucleic acid of FIG. 28.
Figure 30:
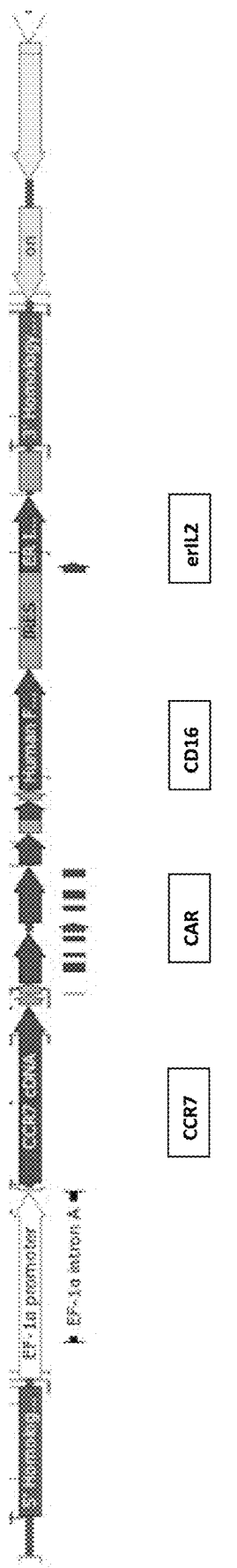
FIG. 30 is a schematic representation of an exemplary quadracistronic recombinant nucleic acid encoding CCR7, a CAR, a high-affinity variant of CD16, and erIL-2 used to generate recombinant NK cells.

Similarly, quadracistronic constructs were prepared using a secreted IL-12 single chain heterodimer as is schematically depicted in FIG. 28. Once more, a P2A sequence was placed between the IL-12 single chain heterodimer sequence and the CAR sequence. FIG. 29 shows exemplary embodiments of the single chain heterodimer with alternate order of p35 and p40 subunits (which were both separated by a linker sequence). As can be seen from the expression levels tested, both single chain heterodimers expressed equally well in the cells tested relative to control. In a still further embodiment, a quadracistronic construct was prepared using CCR7 as a homing receptor and an exemplary quadricictronic arrangement is depicted in FIG. 30.

Of course, it should be recognized that for all nucleic acid sequences provided herein the corresponding encoded proteins are also expressly contemplated herein. Likewise, for all amino acid sequences, corresponding nucleic acids sequences are also contemplated herein (with any codon usage).

All patent applications, publications, references, and sequence accession numbers cited in the present specification are hereby incorporated by reference in their entirety.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

It is understood that all numerical values described herein (e.g., pH, temperature, time, concentration, amounts, and molecular weight, including ranges) include normal variation in measurements encountered by one of ordinary skill in the art. Thus, numerical values described herein include variation of +/−0.1 to 10%, for example, +/−0.1%, 0.5%, 1%, 2%, 3%, 4%, 5%, 6%, 7%, 8%, 9%, or 10%. It is to be understood, although not always explicitly stated, that all numerical designations may be preceded by the term "about." Thus, the term about includes variation of +/−0.1 to 10%, for example, +/−0.1%, 0.5%, 1%, 2%, 3%, 4%, 5%, 6%, 7%, 8%, 9%, or 10% of the numerical value. It is also to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein include the end points of the range, and include all values between the end points of the range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3ζ surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest (hereafter, "NK-92™ cells"). The immortal NK cell line was originally obtained from a patient having non-Hodgkin's lymphoma. Unless indicated otherwise, the term "NK-92™" is intended to refer to the original NK-92 cell lines as well as NK-92 cell lines that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™ NK-92™-CD16, NK-92™-CD16-γ, NK-92™-CD16-ζ, NK-92™-CD16(F176V), NK-92™MI, and NK-92™CI. NK-92 cells are known to persons of ordinary skill in the art, to whom such cells are readily available from NantKwest, Inc.

The term "aNK" refers to an unmodified natural killer cells derived from the highly potent unique cell line described in Gong et al. (1994), rights to which are owned by NantKwest (hereafter, "aNK™ cells"). The term "haNK" refers to natural killer cells derived from the highly potent unique cell line described in Gong et al. (1994), rights to which are owned by NantKwest, modified to express CD16 on the cell surface (hereafter, "CD16+NK-92™ cells" or "haNK® cells"). In some embodiments, the CD16+NK-92™ cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92™ cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+ NK-92™ cells" or "t-haNK™ cells"). In some embodiments, the t-haNK™ cells express a high affinity CD16 receptor on the cell surface.

A "modified NK-92 cell" refers to an NK-92 cell that expresses an exogenous gene or protein, such as an Fc receptor, a CAR, a cytokine (such as IL-2 or IL-15), and/or a suicide gene. In some embodiments, the modified NK-92 cell comprises a vector that encodes for a transgene, such as an Fc receptor, a CAR, a cytokine (such as IL-2 or IL-15), and/or a suicide gene. In one embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be prevented from proliferating by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A is a low affinity Fc receptor bind to IgG antibodies and activate ADCC. FCγRIII-A are typically found on NK cells. NK-92 cells do not express FCγRIII-A. Fc-epsilon receptors (FcεR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The term "virus-specific antigen" as used herein refers to antigens that are present on a virus-infected cell but not detectable on a normal cell derived from the same tissue or lineage as the virus-infected cell. In one embodiment, a virus-specific antigen is a viral protein expressed on the surface of an infected cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous amino acid sequence has no more than 15, nor more than 10, nor more than 5 or no more than 3 conservative amino acid substitutions. In some embodiments, a nucleotide or amino acid sequence has at least 60%, at least 65%, at least 70%, at least 80%, or at least 85% or greater percent identity to a sequence described herein. In some embodiments, a nucleotide or amino acid sequence has at least 90%, 91%, 92%, 93%, 94%, 95%, 96%, 97%, 98% or 99% identity to a sequence described herein. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). Algorithms suitable for determining percent sequence identity include the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (see the internet at ncbi.nlm.nih.gov). The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4.

In some embodiments, a nucleic acid sequence is codon optimized for expression in a particular species, for example, a mouse sequence can be codon optimized for expression in humans (expression of the protein encoded by the codon-optimized nucleic acid sequence). Thus, in some embodiments, a codon-optimized nucleic acid sequence has at least 60%, at least 65%, at least 70%, at least 80%, or at least 85% or greater percent identity to a nucleic acid sequence described herein. In some embodiments, a codon-optimized nucleic acid sequence acid sequence has at least 90%, 91%, 92%, 93%, 94%, 95%, 96%, 97%, 98% or 99% identity to a sequence described herein.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL)—in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation.

A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92 cells to recognize and kill a tumor cell (i.e., target cell). The term "targeted" in this context refers, for example, to the ability of a CAR expressed by the NK-92 cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

What is claimed is:

1. A genetically modified NK cell transfected with one or more recombinant nucleic acids encoding and expressing
   (i) a membrane bound recombinant chimeric antigen receptor (CAR) that comprises in a single polypeptide chain an extracellular binding domain having SEQ ID NO:41, a hinge domain, a transmembrane domain, and a FcεRIγ signaling domain having the polypeptide sequence of SEQ ID NO:1, wherein the extracellular binding domain specifically binds to EGFR;
   (ii) a recombinant CD16;
   (iii) an autocrine growth stimulating cytokine.

2. The genetically modified NK cell of claim 1 wherein the NK cell is an NK-92 cell.

3. The genetically modified NK cell of claim 1 wherein the recombinant CD16 is a CD16$^{158V}$ mutant.

4. The genetically modified NK cell of claim 1 wherein the autocrine growth stimulating cytokine is IL-2 or IL-15.

5. The genetically modified NK cell of claim 4 wherein the autocrine IL-2 or IL-15 further comprises an endoplasmic retention sequence.

6. The genetically modified NK cell of claim 1 wherein the one or more recombinant nucleic acids further encodes and the cell expresses one of IL-12, a TGF-beta trap, or a homing receptor.

7. The genetically modified NK cell of claim 6 wherein the IL-12 is a single chain IL-12 heterodimer.

8. The genetically modified NK cell of claim 6 wherein the TGF-beta trap comprises a single chain dimer of the TGF-beta Receptor II ectodomain.

9. The genetically modified NK cell of claim 8 wherein the TGF-beta trap is a secreted form of a single chain dimer of the TGF-beta Receptor II ectodomain.

10. The genetically modified NK cell of claim 6 wherein the homing receptor is a cell adhesion molecule, a selectin, an integrin, a C-C chemokine receptor, or C-X-C chemokine receptor.

11. The genetically modified NK cell of claim 10 wherein the homing receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3 CR1, XCR1, CCXCKR, D6, DARC, and a receptor for CXCL14.

12. A genetically modified NK cell, comprising:
    a recombinant nucleic acid encoding
    (i) a membrane bound recombinant chimeric antigen receptor (CAR) that comprises in a single polypeptide chain an extracellular binding domain having SEQ ID NO:41, a hinge domain, a transmembrane domain, and a FcεRIγ signaling domain having the polypeptide sequence of SEQ ID NO:1, wherein the extracellular binding domain specifically binds to EGFR;
    (ii) a recombinant CD16;
    (iii) an autocrine growth stimulating cytokine.

13. The genetically modified NK cell of claim 12 wherein the recombinant nucleic acid is a polycistronic DNA.

14. The genetically modified NK cell of claim 12 wherein the NK cell is an NK-92 cell.

15. The genetically modified NK cell of claim 12 wherein the recombinant CD16 is a CD16$^{158V}$ mutant.

16. The genetically modified NK cell of claim 12 wherein the autocrine growth stimulating cytokine is IL-2 or IL-15.

17. The genetically modified NK cell of claim 16 wherein the autocrine IL-2 or IL-15 further comprises an endoplasmic retention sequence.

18. The genetically modified NK cell of claim 12 wherein the recombinant nucleic further encodes one of IL-12, a TGF-beta trap, or a homing receptor.

19. The genetically modified NK cell of claim 18 wherein the IL-12 is a single chain IL-12 heterodimer.

20. The genetically modified NK cell of claim 18 wherein the TGF-beta trap comprises a single chain dimer of the TGF-beta Receptor II ectodomain.

21. The genetically modified NK cell of claim 20 wherein the TGF-beta trap is a secreted form of a single chain dimer of the TGF-beta Receptor II ectodomain.

22. The genetically modified NK cell of claim 18 wherein the homing receptor is a cell adhesion molecule, a selectin, an integrin, a C-C chemokine receptor, or C-X-C chemokine receptor.

23. The genetically modified NK cell of claim 22 wherein the homing receptor is selected from the group consisting of CCR1, CCR2, CCR3, CCR4, CCR5, CCR6, CCR7, CCR8, CCR9, CCR10, CXCR1, CXCR2, CXCR3, CXCR4, CXCRS, CXCR6, CXCR7, CX3 CR1, XCR1, CCXCKR, D6, DARC, and a receptor for CXCL14.

24. A method of treating cancer in a patient in need thereof, comprising administering to the patient a therapeutically effective amount of the genetically modified NK cells of claim 1 thereby treating the cancer.

25. The method of claim 24 further comprising a step of administering at least one additional therapeutic entity selected from the group consisting of a viral cancer vaccine, a bacterial cancer vaccine, a yeast cancer vaccine, N-803, an antibody, a stem cell transplant, and a tumor targeted cytokine.

26. The method of claim 24, wherein the cancer is a lung cancer, a breast cancer, a thyroid cancer, an esophageal cancer, a gastric cancer, a gastroesophageal cancer, or a head and neck cancer.

27. The method of claim 24, wherein about $1\times10^8$ to about $1\times10^{11}$ cells per m$^2$ of body surface area of the patient are administered to the patient.

* * * * *